US008341557B2

(12) United States Patent
Pisula et al.

(10) Patent No.: US 8,341,557 B2
(45) Date of Patent: Dec. 25, 2012

(54) PORTABLE TOUCH SCREEN DEVICE, METHOD, AND GRAPHICAL USER INTERFACE FOR PROVIDING WORKOUT SUPPORT

(75) Inventors: Charles J. Pisula, San Jose, CA (US); Lucas C. Newman, Mountain View, CA (US); Freddy Allen Anzures, San Francisco, CA (US); Nitin K. Ganatra, San Jose, CA (US)

(73) Assignee: Apple Inc., Cupertino, CA (US)

( * ) Notice: Subject to any disclaimer, the term of this patent is extended or adjusted under 35 U.S.C. 154(b) by 1103 days.

(21) Appl. No.: 12/205,847

(22) Filed: Sep. 5, 2008

(65) Prior Publication Data

US 2010/0060586 A1 Mar. 11, 2010

(51) Int. Cl.
- *G06F 3/033* (2006.01)
- *G06F 3/01* (2006.01)
- *G06F 3/048* (2006.01)
- *G06F 3/14* (2006.01)
- *G06F 3/00* (2006.01)
- *G06F 3/02* (2006.01)
- *G06F 3/041* (2006.01)
- *G06G 5/00* (2006.01)
- *A63B 71/00* (2006.01)

(52) U.S. Cl. ........ 715/863; 715/702; 715/772; 715/833; 715/864; 715/866; 345/169; 345/173; 482/8; 482/9; 482/901; 482/902

(58) Field of Classification Search .................. 482/8, 9, 482/901, 902; 345/169, 173; 715/702, 772, 715/833, 863, 864, 866

See application file for complete search history.

(56) References Cited

U.S. PATENT DOCUMENTS

| 6,013,008 | A | * | 1/2000 | Fukushima | 482/8 |
| 6,639,584 | B1 | * | 10/2003 | Li | 345/173 |
| 6,837,827 | B1 | * | 1/2005 | Lee et al. | 482/8 |
| 6,866,613 | B1 | * | 3/2005 | Brown et al. | 482/8 |
| 7,046,230 | B2 | | 5/2006 | Zadesky et al. | |
| 7,251,454 | B2 | * | 7/2007 | White | 455/41.2 |
| 7,480,870 | B2 | | 1/2009 | Anzures et al. | 715/772 |
| 7,495,659 | B2 | | 2/2009 | Marriott et al. | |
| 7,499,040 | B2 | | 3/2009 | Zadesky et al. | |
| 7,656,393 | B2 | | 2/2010 | King et al. | |

(Continued)

OTHER PUBLICATIONS

Iphone User's Guide, 2007.*

(Continued)

*Primary Examiner* — Kieu Vu
*Assistant Examiner* — Eric J Bycer
(74) *Attorney, Agent, or Firm* — Morgan, Lewis & Bockius LLP

(57) ABSTRACT

In some embodiments, a computer-implemented method is performed at a portable electronic device with a touch screen display while the portable electronic device is in a user-interface locked mode of a workout monitoring application with the touch screen display turned off. The method includes: monitoring a workout by a user with the workout monitoring application; detecting an interaction by the user with a first physical button on the portable electronic device; and determining whether the detected interaction by the user with the first physical button corresponds to a first predefined action. The method further includes, in response to determining that the interaction by the user with the first physical button corresponds to the first predefined action; turning on the touch screen display; providing an audio status report of the workout by the user; displaying a workout pause icon; and displaying an unlock image.

55 Claims, 52 Drawing Sheets

U.S. PATENT DOCUMENTS

| | | | |
|---|---|---|---|
| 7,657,849 | B2 | 2/2010 | Chaudhri et al. |
| 7,662,065 | B1* | 2/2010 | Kahn et al. ............... 482/9 |
| 7,663,607 | B2 | 2/2010 | Hotelling et al. |
| 7,800,592 | B2 | 9/2010 | Kerr et al. |
| 7,808,479 | B1 | 10/2010 | Hotelling et al. |
| 8,082,523 | B2 | 12/2011 | Forstall et al. |
| 2005/0216867 | A1* | 9/2005 | Marvit et al. ............ 715/863 |
| 2005/0228691 | A1 | 10/2005 | Paparo ..................... 705/2 |
| 2006/0026521 | A1 | 2/2006 | Hotelling et al. |
| 2006/0026535 | A1 | 2/2006 | Hotelling et al. |
| 2006/0181517 | A1 | 8/2006 | Zadesky et al. |
| 2006/0197753 | A1 | 9/2006 | Hotelling |
| 2007/0021269 | A1* | 1/2007 | Shum ....................... 482/8 |
| 2007/0150842 | A1 | 6/2007 | Chaudhri et al. ........ 715/863 |
| 2007/0270721 | A1 | 11/2007 | Ananny et al. ........... 600/595 |
| 2007/0271065 | A1 | 11/2007 | Gupta et al. ............. 702/160 |
| 2007/0271387 | A1 | 11/2007 | Lydon et al. ............ 709/230 |
| 2008/0088602 | A1 | 4/2008 | Hotelling |
| 2008/0096726 | A1* | 4/2008 | Riley et al. ............... 482/8 |
| 2008/0122796 | A1 | 5/2008 | Jobs et al. |
| 2008/0168379 | A1 | 7/2008 | Forstall et al. |
| 2009/0088204 | A1 | 4/2009 | Culbert et al. .......... 455/556.1 |
| 2009/0100384 | A1 | 4/2009 | Louch ..................... 715/863 |
| 2009/0233771 | A1* | 9/2009 | Quatrochi et al. ........ 482/9 |
| 2009/0262088 | A1* | 10/2009 | Moll-Carrillo et al. ....... 345/173 |
| 2009/0295753 | A1 | 12/2009 | King et al. |
| 2010/0031202 | A1* | 2/2010 | Morris et al. ............ 715/863 |
| 2010/0058251 | A1 | 3/2010 | Rottler et al. |

OTHER PUBLICATIONS

"My CalStep," from www.surprisesoftware.com/mycalstep, retireved from the Wayback Machine, May 9, 2007.*

"dwProgressBar 2" from davidwalsh.name/dwprogressbar-2-stepping-events-mootools-progress-bar, retrieved from the Wayback Machine, Aug. 31, 2008.*

Apple.com, "Tune Your Run," http://www.apple.com/ipod/nike/, Retrieved Aug. 22, 2008.

Gadget Spire, "Nike + Apple = Nike Iphone," posted on Apr. 11, 2008, http://gadgetspire.com/nike-apple-nike-iphone.

Garmin International, "Garmin Nüvifone Takes Personal Navigation and Communication to the Next Level," 3 pages, printed Mar. 17, 2008, http://www8.garmin.com/pressroom/mobile/013008.html.

Garmin, "Nüvifone—Media Gallery," 2 pages, printed Feb. 4, 2008, http://www8.garmin.com/buzz/nuvifone/media_gallery.jsp.

Runkeeper.com, "RunKeeper Getting Started Tutorial," http://www.runkeeper.com/doc/iphone/GetStartedTutorial.html, Retrieved Aug. 22, 2008

Runkeeper.com, "RunKeeper," http://www.runkeeper.com, Retrieved Aug. 22, 2008.

Skidmore, S., "New Phone Coaches, Monitors Heart Rate," Associated Press, Mar. 6, 2008, http://news.yahoo.corn/s/ap/20080306/ap_on_hi_te/adidas_samsung_2&printer=1.

Wikipedia, "Nike+iPod," http://en.wikipedia.org/wiki/Nike%2BiPod, Retrieved Aug. 25, 2008.

Apple, "Nike+iPod User's Guide," © 2006 Apple Computer, Inc., 18 pages, http://manuals.info.apple.com/en/Nike_+_iPod_User_Guide.pdf.

Tidwell J., "Designing Interfaces," Nov. 2006, O'Reilly Media, Inc., 348 pages.

Westerman, W., "Hand Tracking Finger identification and Chordic Manipulation on a Multi-touch Surface," Doctoral Dissertation, submitted Spring 1999, 363 pages.

* cited by examiner

5000

```
While a portable electronic device with a touch screen display
is in a user-interface locked mode of a workout monitoring
application with the touch screen display turned off:
```

Monitor a workout by a user with the workout monitoring application — 5002

Receive data from a sensor that is separate from the portable electronic device — 5004

Play an audio file from a playlist with a plurality of audio files — 5006

Detect an interaction by the user with a first physical button on the portable electronic device — 5008

Determine whether the detected interaction by the user with the first physical button corresponds to a first predefined action — 5010

The first predefined action is a single activation of the first physical button in a predefined time period — 5012

In response to determining that the interaction by the user with the first physical button corresponds to the first predefined action: turn on the touch screen display; display a workout pause icon on the touch screen display; and display an unlock image on the touch screen display — 5014 provide an audio status report of the workout by the user — 5015

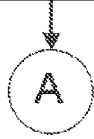

Figure 5A

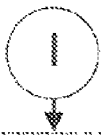

While the portable electronic device is in a user-interface unlock state and while monitoring the workout by the user with the workout monitoring application:

In response to detecting a finger gesture on the application icon in the menu of application icons other than the icon for the workout monitoring application, display a user interface for a corresponding application on the touch screen display while continuing to maintain monitoring of the workout by the user, wherein the user interface for the corresponding application includes a return-to-workout-monitoring-application icon that is not displayed in the user interface for the corresponding application when there is no ongoing monitoring of the workout by the user — 5088

Detect a finger gesture on the return-to-workout-monitoring-application icon — 5090

In response to detecting the finger gesture on the return-to-workout-monitoring-application icon, replace display of the user interface for the corresponding application with a respective user interface for the workout monitoring application while continuing to monitor the workout by the user — 5092

Transition the portable electronic device to a user-interface locked mode of the workout monitoring application upon expiration of a pre-determined time period without detecting user input to the device — 5094

```
┌─────────────────────────────────────────────────────────┐
│ Monitor a workout by a user with a workout monitoring   │── 6002
│ application, wherein the workout has a predetermined    │
│ workout goal for the user                               │
│  ┌───────────────────────────────────────────────────┐  │
│  │ The predetermined workout goal for the user is a  │  │── 6004
│  │ predetermined time for the workout, a predetermined│ │
│  │ distance to be traveled in the workout, or a      │  │
│  │ predetermined number of calories to be burned in  │  │
│  │ the workout                                       │  │
│  └───────────────────────────────────────────────────┘  │
└─────────────────────────────────────────────────────────┘
                            │
                            ▼
┌─────────────────────────────────────────────────────────┐
│ Display a workout progress bar on the touch screen      │
│ display, wherein the workout progress bar indicates a   │── 6006
│ portion of the predetermined workout goal fulfilled by  │
│ the user                                                │
└─────────────────────────────────────────────────────────┘
                            │
                            ▼
┌─────────────────────────────────────────────────────────┐
│ Update the workout progress bar to display the portion  │
│ of the predetermined workout goal fulfilled by the user │── 6008
│ until the predetermined workout goal is met             │
└─────────────────────────────────────────────────────────┘
                            │
                            ▼
┌─────────────────────────────────────────────────────────┐
│ Detect fulfillment of the predetermined workout goal    │── 6010
└─────────────────────────────────────────────────────────┘
                            │
                            ▼
┌─────────────────────────────────────────────────────────┐
│ In response to detecting fulfillment of the predetermined│── 6012
│ workout goal, display an indicator that the predetermined│
│ workout goal has been reached                           │
│  ┌───────────────────────────────────────────────────┐  │
│  │ Overlay the indicator on the workout progress bar │  │── 6014
│  └───────────────────────────────────────────────────┘  │
│  ┌───────────────────────────────────────────────────┐  │
│  │ Overlay the indicator on a post-workout-goal      │  │── 6016
│  │ activity bar                                      │  │
│  └───────────────────────────────────────────────────┘  │
│  ┌───────────────────────────────────────────────────┐  │
│  │ The indicator is a checkmark                      │  │── 6018
│  └───────────────────────────────────────────────────┘  │
└─────────────────────────────────────────────────────────┘
                            │
                            ▼
                          ( A )
```

While a portable electronic device with a touch screen display is in a user-interface locked mode of a workout monitoring application with the touch screen display turned on:

Detect a finger gesture on a powersong initiation icon displayed on the touch screen display ~ 7002

In response to detecting the finger gesture on the powersong initiation icon, initiate playing of an audio file previously selected by the user as the user's powersong ~ 7004

While a portable electronic device with a touch screen display is in a user-interface locked mode of a workout monitoring application with the touch screen display turned on:

- Monitor a workout by a user with the workout monitoring application — 8002
- Play an audio file from a playlist with a plurality of audio files — 8004
- Detect a finger swipe gesture on the touch screen display — 8006
- Determine whether the detected finger swipe gesture is in a first predefined direction or a second predefined direction on the touch screen display, the second predefined direction being opposite the first predefined direction — 8008
- In response to determining that the finger swipe gesture is in the first predefined direction, terminate play of the audio file and initiate play of a next audio file from the playlist — 8010
- In response to determining that the finger swipe gesture is in the second predefined direction, terminate playing of the audio file and initiate play of a previous audio file from the playlist — 8012

While a portable electronic device with a touch screen display is in a user-interface locked mode of a workout monitoring application with the touch screen display turned on:

Monitor a workout by a user with the workout monitoring application — 9002

Play an audio file from a playlist with a plurality of audio files — 9004

Detect a finger swipe gesture on the touch screen display — 9006

In response to detecting the finger swipe gesture:
terminate play of the audio file and initiate play of a next audio file from the playlist if the detected finger gesture is in a first horizontal direction across the touch screen display;
terminate play of the audio file and initiate play of the next audio file from the playlist if the detected finger gesture is in a first vertical direction across the touch screen display;
terminate play of the audio file and initiate play of a previous audio file from the playlist if the detected finger gesture is in a second horizontal direction across the touch screen display, the second horizontal direction being opposite the first horizontal direction; and
terminate play of the audio file and initiate play of the previous audio file from the playlist if the detected finger gesture is in a second vertical direction across the touch screen display, the second vertical direction being opposite the first vertical direction. — 9008

While a portable electronic device with a touch screen display is in a user-interface locked mode of an application with the touch screen display turned on:

Display a locked-mode user interface for the application on the touch screen display — 1002

The displayed locked-mode user interface for the application comprises an unlock screen for the application — 1004

The displayed locked-mode user interface for the application comprises an unlock image — 1006

The application is an application that provides audio output — 1008

The application is a workout support application — 1010

The application is a music player application — 1012

Detect a finger gesture on the touch screen display — 1014

In response to detecting the finger gesture on the touch screen display, perform a control operation in the application while maintaining display of the same locked-mode user interface for the application — 1016

Figure 10

PORTABLE TOUCH SCREEN DEVICE, METHOD, AND GRAPHICAL USER INTERFACE FOR PROVIDING WORKOUT SUPPORT

RELATED APPLICATIONS

This application is related to the following applications: (1) U.S. patent application Ser. No. 10/188,182, "Touch Pad For Handheld Device," filed Jul. 1, 2002; (2) U.S. patent application Ser. No. 10/722,948, "Touch Pad For Handheld Device," filed Nov. 25, 2003; (3) U.S. patent application Ser. No. 10/643,256, "Movable Touch Pad With Added Functionality," filed Aug. 18, 2003; (4) U.S. patent application Ser. No. 10/654,108, "Ambidextrous Mouse," filed Sep. 2, 2003; (5) U.S. patent application Ser. No. 10/840,862, "Multipoint Touchscreen," filed May 6, 2004; (6) U.S. patent application Ser. No. 10/903,964, "Gestures For Touch Sensitive Input Devices," filed Jul. 30, 2004; (7) U.S. patent application Ser. No. 11/038,590, "Mode-Based Graphical User Interfaces For Touch Sensitive Input Devices" filed Jan. 18, 2005; (8) U.S. patent application Ser. No. 11/057,050, "Display Actuator," filed Feb. 11, 2005; (9) U.S. patent application Ser. No. 11/367,749, "Multi-Functional Hand-Held Device," filed Mar. 3, 2006; (10) U.S. patent application Ser. No. 11/850,635, "Touch Screen Device, Method, and Graphical User interface for Determining Commands by Applying Heuristics," filed Sep. 5, 2007; (11) U.S. patent application Ser. No. 11/585,721, "Calibration Techniques for Activity Sensing Devices," filed Oct. 23, 2006; (12) U.S. patent application Ser. No. 11/439,523, "Portable Media Device with Workout Support," filed May 22, 2006; (13) U.S. patent application Ser. No. 11/439,521, "Communication Protocol for Use with Portable Electronic Devices," filed May 22, 2006; (14) U.S. patent application Ser. No. 11/322,549, "Unlocking a Device by Performing Gestures on an Unlock Image," filed Dec. 23, 2005; (15) U.S. patent application Ser. No. 11/969,908, "Portable Electronic Device Supporting Application Switching," filed Jan. 6, 2008; and (16) U.S. patent application Ser. No. 11/770,727, "Portable Electronic Device with Alert Silencing," filed Jun. 28, 2007. All of these applications are incorporated by reference herein in their entirety.

TECHNICAL FIELD

The disclosed embodiments relate generally to portable electronic devices that support user exercise routines, and more particularly, to portable electronic devices with touch screen displays that support user exercise routines.

BACKGROUND

As portable electronic devices become more compact, and the number of functions performed by a given device increase, it has become a significant challenge to design a user interface that allows users to easily interact with a multifunction device. This challenge is particularly significant for handheld portable devices with touch-sensitive displays, which have much smaller screens than desktop or laptop computers. This situation is unfortunate because the user interface is the gateway through which users receive not only content, but also responses to user actions or behaviors, including user attempts to access a device's features, tools, and functions.

Portable media players, such as MP3 players, are often used for playing music while exercising. Media players have been integrated into mobile telephones and/or personal information managers (or digital personal assistants). These media players may be part of multifunction devices with touch-sensitive displays, like the iPhone® and iPod Touch® from Apple Computer, Inc. of Cupertino, Calif.

Recently, portable electronic devices have been enhanced to support wireless communications, such as with Bluetooth® communication protocols. To help people with their sports/workout regimens, some portable electronic devices can communicate with a wireless speed and distance sensor in the user's shoe. The wireless speed and distance sensor operates as a pedometer and can wirelessly transmit data to the portable electronic device. Such systems permit interaction between a portable electronic device and a pedometer, which are conventionally separate devices.

While exercising, users will often attach portable electronic devices with workout support applications to locations on their bodies where it is difficult to see the controls and the display. For example, a runner may use an armband to mount a device on her upper arm so she need not carry the device in her hand. But manipulating on-screen controls is difficult when a device is mounted to one's upper arm.

Accordingly, there is a need for portable electronic devices with touch screen displays that have more transparent and intuitive user interfaces for providing sports/workout support. Such interfaces increase the effectiveness, efficiency and user satisfaction with such portable devices.

In addition, there is a need for portable electronic devices with touch screen displays that provide control of an application (e.g., a workout support application or other application that provides audio) with finger gestures while the application is in a user-interface locked mode of operation.

SUMMARY

The above deficiencies and other problems associated with user interfaces for providing sports/workout support on portable devices are reduced or eliminated by the disclosed portable multifunction device. In some embodiments, the device has a touch-sensitive display (also known as a "touch screen") with a graphical user interface (GUI), one or more processors, memory and one or more modules, programs or sets of instructions stored in the memory for performing multiple functions. In some embodiments, the user interacts with the GUI primarily through finger contacts and gestures on the touch-sensitive display. In some embodiments, in addition to providing sports/workout support, the functions may include telephoning, video conferencing, e-mailing, instant messaging, blogging, digital photographing, digital videoing, web browsing, digital music playing, and/or digital video playing. Instructions for performing these functions may be included in a computer program product configured for execution by one or more processors.

In accordance with some embodiments, a computer-implemented method is performed at a portable electronic device with a touch screen display while the portable electronic device is in a user-interface locked mode of a workout monitoring application with the touch screen display turned off. The computer-implemented method includes: monitoring a workout by a user with the workout monitoring application; detecting an interaction by the user with a first physical button on the portable electronic device; and determining whether the detected interaction by the user with the first physical button corresponds to a first predefined action. The computer-implemented method further includes, in response to determining that the interaction by the user with the first physical button corresponds to the first predefined action: turning on the touch screen display; providing an audio status report of the workout by the user; displaying a workout pause icon on the touch screen display; and displaying an unlock image on the touch screen display. The unlock image is a graphical user interface object with which the user interacts in order to change the workout monitoring application to a user-interface unlocked mode.

In accordance with some embodiments, a portable electronic device includes: a touch screen display; one or more processors; memory; and one or more programs. The one or more programs are stored in the memory and configured to be executed by the one or more processors. The one or more programs include instructions for, while the portable electronic device is in a user-interface locked mode of a workout monitoring application with the touch screen display turned off: monitoring a workout by a user with the workout monitoring application; detecting an interaction by the user with a first physical button on the portable electronic device; and determining whether the detected interaction by the user with the first physical button corresponds to a first predefined action. The one or more programs further include instructions for, in response to determining that the interaction by the user with the first physical button corresponds to the first predefined action: turning on the touch screen display; providing an audio status report of the workout by the user; displaying a workout pause icon on the touch screen display; and displaying an unlock image on the touch screen display. The unlock image is a graphical user interface object with which the user interacts in order to change the workout monitoring application to a user-interface unlocked mode.

In accordance with some embodiments, a computer readable storage medium has stored therein instructions, which when executed by a portable electronic device with a touch screen display while the portable electronic device is in a user-interface locked mode of a workout monitoring application with the touch screen display turned off, cause the portable electronic device to: monitor a workout by a user with the workout monitoring application; detect an interaction by the user with a first physical button on the portable electronic device; and determine whether the detected interaction by the user with the first physical button corresponds to a first predefined action. The instructions further cause the device to, in response to determining that the interaction by the user with the first physical button corresponds to the first predefined action: turn on the touch screen display; provide an audio status report of the workout by the user; display a workout pause icon on the touch screen display; and display an unlock image on the touch screen display. The unlock image is a graphical user interface object with which the user interacts in order to change the workout monitoring application to a user-interface unlocked mode.

In accordance with some embodiments, a graphical user interface on a portable electronic device with a touch screen display includes a workout pause icon on the touch screen display and an unlock image on the touch screen display. The unlock image is a graphical user interface object with which the user interacts in order to change a workout monitoring application to a user-interface unlocked mode. While the portable electronic device is in a user-interface locked mode of a workout monitoring application with the touch screen display turned off: a workout by a user is monitored with the workout monitoring application; an interaction by the user with a first physical button on the portable electronic device is detected; and whether the detected interaction by the user with the first physical button corresponds to a first predefined action is determined. In response to determining that the interaction by the user with the first physical button corresponds to the first predefined action: the touch screen display is turned on; an audio status report of the workout by the user is provided; the workout pause icon is displayed on the touch screen display; and the unlock image is displayed on the touch screen display.

In accordance with some embodiments, a portable electronic device includes a touch screen display. While the portable electronic device is in a user-interface locked mode of a workout monitoring application with the touch screen display turned off, the device includes: means for monitoring a workout by a user with the workout monitoring application; means for detecting an interaction by the user with a first physical button on the portable electronic device; and means for determining whether the detected interaction by the user with the first physical button corresponds to a first predefined action. The device also includes, in response to determining that the interaction by the user with the first physical button corresponds to the first predefined action: means for turning on the touch screen display; means for providing an audio status report of the workout by the user; means for displaying a workout pause icon on the touch screen display; and means for displaying an unlock image on the touch screen display. The unlock image is a graphical user interface object with which the user interacts in order to change the workout monitoring application to a user-interface unlocked mode.

In accordance with some embodiments, a computer-implemented method is performed at a portable electronic device with a touch screen display. The computer-implemented method includes; monitoring a workout by a user with a workout monitoring application, wherein the workout has a predetermined workout goal for the user; displaying a workout progress bar on the touch screen display, wherein the workout progress bar indicates a portion of the predetermined workout goal fulfilled by the user; updating the workout progress bar to display the portion of the predetermined workout goal fulfilled by the user until the predetermined workout goal is met; displaying a post-workout-goal activity bar on the touch screen display, wherein the post-workout-goal activity bar indicates activity by the user beyond the predetermined workout goal; and updating the post-workout-goal activity bar while the user continues to workout after reaching the predetermined workout goal.

In accordance with some embodiments, a portable electronic device includes: a touch screen display; one or more processors; memory; and one or more programs. The one or more programs are stored in the memory and configured to be executed by the one or more processors. The one or more programs include instructions for: monitoring a workout by a user with a workout monitoring application, wherein the workout, has a predetermined workout goal for the user; displaying a workout progress bar on the touch screen display, wherein the workout progress bar indicates a portion of the predetermined workout goal fulfilled by the user; updating the workout progress bar to display the portion of the predetermined workout goal fulfilled by the user until the predetermined workout goal is met; displaying a post-workout-goal activity bar on the touch screen display, wherein the post-workout-goal activity bar indicates activity by the user beyond the predetermined workout goal; and updating the post-workout-goal activity bar while the user continues to workout after reaching the predetermined workout goal.

In accordance with some embodiments, a computer readable storage medium has stored therein instructions, which when executed by a portable electronic device with a touch screen display, cause the portable electronic device to: monitor a workout by a user with a workout monitoring application, wherein the workout has a predetermined workout goal for the user; display a workout progress bar on the touch screen display, wherein the workout progress bar indicates a portion of the predetermined workout goal fulfilled by the user; update the workout progress bar to display the portion of the predetermined workout goal fulfilled by the user until the predetermined workout goal is met; display a post-workout-goal activity bar on the touch screen display, wherein the post-workout-goal activity bar indicates activity by the user beyond the predetermined workout goal; and update the post-workout-goal activity bar while the user continues to workout after reaching the predetermined workout goal.

In accordance with some embodiments, a graphical user interface on a portable electronic device with a touch screen display includes: a workout progress bar on the touch screen display that indicates a portion of a predetermined workout goal fulfilled by the user, and a post-workout-goal activity bar that indicates activity by the user beyond the predetermined workout goal. A workout by a user is monitored with a workout monitoring application. The workout progress bar is updated to display the portion of the predetermined workout goal fulfilled by the user until the predetermined workout goal is met. The post-workout-goal activity bar is updated while the user continues to workout after reaching the predetermined workout goal.

In accordance with some embodiments, a portable electronic device includes a touch screen display; means for monitoring a workout by a user with a workout monitoring application, wherein the workout has a predetermined workout goal for the user; means for displaying a workout progress bar on the touch screen display, wherein the workout progress bar indicates a portion of the predetermined workout goal fulfilled by the user; means for updating the workout progress bar to display the portion of the predetermined workout goal fulfilled by the user until the predetermined workout goal is met; means for displaying a post-workout-goal activity bar on the touch screen display, wherein the post-workout-goal activity bar indicates activity by the user beyond the predetermined workout goal; and means for updating the post-workout-goal activity bar while the user continues to workout after reaching the predetermined workout goal.

In accordance with some embodiments, a computer-implemented method is performed at a portable electronic device with a touch screen display while the portable electronic device is in a user-interface locked mode of a workout monitoring application with the touch screen display turned on. The computer-implemented method includes: detecting a finger gesture on a powersong initiation icon; and, in response to detecting the finger gesture on the powersong initiation icon, initiating playing of an audio file previously selected by the user as the user's powersong.

In accordance with some embodiments, a portable electronic device includes: a touch screen display; one or more processors; memory; and one or more programs. The one or more programs are stored in the memory and configured to be executed by the one or more processors. The one or more programs include instructions for, while the portable electronic device is in a user-interface locked mode of a workout monitoring application with the touch screen display turned on: detecting a finger gesture on a powersong initiation icon; and, in response to detecting the finger gesture on the powersong initiation icon, initiating playing of an audio file previously selected by the user as the user's powersong.

In accordance with some embodiments, a computer readable storage medium has stored therein instructions, which when executed by a portable electronic device with a touch screen display while the portable electronic device is in a user-interface locked mode of a workout monitoring application with the touch screen display turned on, cause the portable electronic device to: detect a finger gesture on a powersong initiation icon; and, in response to detecting the finger gesture on the powersong initiation icon, initiate playing of an audio file previously selected by the user as the user's powersong.

In accordance with some embodiments, a graphical user interface on a portable electronic device with a touch screen display includes a powersong initiation icon on the touch screen display. While the portable electronic device is in a user-interface locked mode of a workout monitoring application with the touch screen display turned on: a finger gesture is detected on the powersong initiation icon; and, in response to detecting the finger gesture on the powersong initiation icon, play is initiated of an audio file previously selected by the user as the user's powersong.

In accordance with some embodiments, a portable electronic device includes a touch screen display. While the portable electronic device is in a user-interface locked mode of a workout monitoring application with the touch screen display turned on, the device includes: means for detecting a finger gesture on a powersong initiation icon; and, in response to detecting the finger gesture on the powersong initiation icon, means for initiating playing of an audio file previously selected by the user as the user's powersong.

In accordance with some embodiments, a computer-implemented method is performed at a portable electronic device with a touch screen display while the portable electronic device is in a user-interface locked mode of a workout monitoring application with the touch screen display turned on. The computer-implemented method includes: monitoring a workout by a user with the workout monitoring application; playing an audio file from a playlist with a plurality of audio files; detecting a finger swipe gesture on the touch screen display; determining whether the detected finger swipe gesture is in a first predefined direction or a second predefined direction on the touch screen display, the second predefined direction being opposite the first predefined direction; in response to determining that the finger swipe gesture is in the first predefined direction, terminating play of the audio file and initiating play of a next audio file from the playlist; and, in response to determining that the finger swipe gesture is in the second predefined direction, terminating play of the audio file and initiating play of a previous audio file from the playlist.

In accordance with some embodiments, a portable electronic device includes: a touch screen display; one or more processors; memory; and one or more programs. The one or more programs are stored in the memory and configured to be executed by the one or more processors. The one or more programs include instructions for, while the portable electronic device is in a user-interface locked mode of a workout monitoring application with the touch screen display turned on: monitoring a workout by a user with the workout monitoring application; playing an audio file from a playlist with a plurality of audio files; detecting a finger swipe gesture on the touch screen display; determining whether the detected finger swipe gesture is in a first predefined direction or a second predefined direction on the touch screen display, the second predefined direction being opposite the first predefined direction; in response to determining that the finger swipe gesture is in the first predefined direction, terminating play of the audio file and initiating play of a next audio file from the playlist; and, in response to determining that the finger swipe gesture is in the second predefined direction, terminating play of the audio file and initiating play of a previous audio file from the playlist.

In accordance with some embodiments, a computer readable storage medium has stored therein instructions, which when executed by a portable electronic device with a touch screen display while the portable electronic device is in a user-interface locked mode of a workout monitoring application with the touch screen display turned on, cause the portable electronic device to: monitor a workout by a user with the workout monitoring application; play an audio file from a playlist with a plurality of audio files; detect a finger swipe gesture on the touch screen display; determine whether the detected finger swipe gesture is in a first predefined direction or a second predefined direction on the touch screen display, the second predefined direction being opposite the first predefined direction; in response to determining that the finger swipe gesture is in the first predefined direction, terminate play of the audio file and initiate play of a next audio file from the playlist; and, in response to determining that the finger swipe gesture is in the second predefined direction, terminate play of the audio file and initiate play of a previous audio file from the playlist.

In accordance with some embodiments, a portable electronic device includes a touch screen display. While the portable electronic device is in a user-interface locked mode of a workout monitoring application with the touch screen display turned on, the device includes: means for monitoring a workout by a user with the workout monitoring application; means for playing an audio file from a playlist with a plurality of audio files; means for detecting a finger swipe gesture on the touch screen display; means for determining whether the detected finger swipe gesture is in a first predefined direction or a second predefined direction on the touch screen display, the second predefined direction being opposite the first predefined direction; in response to determining that the finger swipe gesture is in the first predefined direction, means for terminating play of the audio file and means for initiating play of a next audio file from the playlist; and, in response to determining that the finger swipe gesture is in the second predefined direction, means for terminating play of the audio file and means for initiating play of a previous audio file from the playlist.

In accordance with some embodiments, a computer-implemented method is performed at a portable electronic device with a touch screen display while the portable electronic device is in a user-interface locked mode of a workout monitoring application with the touch screen display turned on. The computer-implemented method includes: monitoring a workout by a user with the workout monitoring application; playing an audio file from a playlist with a plurality of audio files; and detecting a finger swipe gesture on the touch screen display. The computer-implemented method further includes, in response to detecting the finger swipe gesture: terminating play of the audio file and initiating play of a next audio ills from the playlist if the detected finger gesture is in a first horizontal direction across the touch screen display; terminating play of the audio file and initiating play of the next audio file from the playlist if the detected finger gesture is in a first vertical direction across the touch screen display; terminating play of the audio file and initiating play of a previous audio file from the playlist if the detected finger gesture is in a second horizontal direction across the touch screen display, the second horizontal direction being opposite the first horizontal direction; and terminating play of the audio file and initiating play of the previous audio file from the playlist if the detected finger gesture is in a second vertical direction across the touch screen display, the second vertical direction being opposite the first vertical direction.

In accordance with some embodiments, a portable electronic device includes: a touch screen display; one or more processors; memory; and one or more programs. The one or more programs are stored in the memory and configured to be executed by the one or more processors. The one or more programs include instructions for, while the portable electronic device is in a user-interface locked mode of a workout monitoring application with the touch screen display turned on; monitoring a workout by a user with the workout monitoring application; playing an audio file from a playlist with a plurality of audio files; and detecting a finger swipe gesture on the touch screen display. The one or more programs further include instructions for, in response to detecting the finger swipe gesture: terminating play of the audio file and initiating play of a next audio file from the playlist if the detected finger gesture is in a first horizontal direction across the touch screen display; terminating play of the audio file and initiating play of the next audio file from the playlist if the detected finger gesture is in a first vertical direction across the touch screen display; terminating play of the audio file and initiating play of a previous audio file from the playlist if the detected finger gesture is in a second horizontal direction across the touch screen display, the second horizontal direction being opposite the first horizontal direction; and terminating play of the audio file and initiating play of the previous audio file from the playlist if the detected finger gesture is in a second vertical direction across the touch screen display, the second vertical direction being opposite the first vertical direction.

In accordance with some embodiments, a computer readable storage medium has stored therein instructions, which when executed by a portable electronic device with a touch screen display while the portable electronic device is in a user-interface locked mode of a workout monitoring application with the touch screen display turned on, cause the portable electronic device to: monitor a workout by a user with the workout monitoring application; play an audio file from a playlist with a plurality of audio files; and detect a finger swipe gesture on the touch screen display. The instructions further cause the device to, in response to detecting the finger swipe gesture: terminate play of the audio file and initiate play of a next audio file from the playlist if the detected finger gesture is in a first horizontal direction across the touch screen display; terminate play of the audio file and initiate play of the next audio file from the playlist if the detected finger gesture is in a first vertical direction across the touch screen display; terminate play of the audio file and initiate play of a previous audio file from the playlist if the detected finger gesture is in a second horizontal direction across the touch screen display, the second horizontal direction being opposite the first horizontal direction; and terminate play of the audio file and initiate play of the previous audio file from the playlist if the detected finger gesture is in a second vertical direction across the touch screen display, the second vertical direction being opposite the first vertical direction.

In accordance with some embodiments, a portable electronic device includes a touch screen display. While the portable electronic device is in a user-interface locked mode of a workout monitoring application with the touch screen display turned on, the device includes: means for monitoring a workout by a user with the workout monitoring application; means for playing an audio file from a playlist with a plurality of audio files; and means for detecting a finger swipe gesture on the touch screen display. The device also includes, in response to detecting the finger swipe gesture: means for terminating play of the audio file and means for initiating play of a next audio file from the playlist if the detected finger gesture is in a first horizontal direction across the touch screen display; means for terminating play of the audio file and means for initiating play of the next audio file from the playlist if the detected finger gesture is in a first vertical direction across the touch screen display; means for terminating play of the audio file and means for initiating play of a previous audio file from the playlist if the detected finger gesture is in a second horizontal direction across the touch screen display, the second horizontal direction being opposite the first horizontal direction; and means for terminating play of the audio file and means for initiating play of the previous audio file from the playlist if the detected finger gesture is in a second vertical direction across the touch screen display, the second vertical direction being opposite the first vertical direction.

In accordance with some embodiments, a computer-implemented method is performed at a portable electronic device with a touch screen display while the portable electronic device is in a user-interface locked mode of an application with the touch screen, display turned on. The computer-implemented method includes: displaying a locked-mode user interface for the application on the touch screen display; detecting a finger gesture on the touch screen display; and, in response to detecting the finger gesture on the touch screen display, performing a control operation in the application while maintaining display of the same locked-mode user interface for the application.

In accordance with some embodiments, a portable electronic device includes: a touch screen display; one or more processors; memory; and one or more programs. The one or more programs are stored in the memory and configured to be executed by the one or more processors. The one or more programs include instructions for, while the portable electronic device is in a user-interface locked mode of an application with the touch screen display turned on; displaying a locked-mode user interface for the application on the touch screen display; detecting a finger gesture on the touch screen display; and, in response to detecting the finger gesture on the touch screen display, performing a control operation in the application while maintaining display of the same locked-mode user interface for the application.

In accordance with some embodiments, a computer readable storage medium has stored therein instructions, which when executed by a portable electronic device with a touch screen display while the portable electronic device is in a user-interface locked mode of an application with the touch screen display turned on, cause the portable electronic device to: display a locked-mode user interface for the application on the touch screen display; detect a finger gesture on the touch screen display; and in response to detecting the finger gesture on the touch screen display, perform a control operation in the application while maintaining display of the same locked-mode user interface for the application.

In accordance with some embodiments, a graphical user interface on a portable electronic device with a touch screen display includes a locked-mode user interface for an application. While the portable electronic device is in a user-interface locked mode of the application with the touch screen display turned on: the locked-mode user interface for the application is displayed on the touch screen display; a finger gesture is detected on the touch screen display; and, in response to detecting the finger gesture on the touch screen display, a control operation is performed in the application while maintaining display of the same locked-mode user interface for the application.

In accordance with some embodiments, a portable electronic device includes a touch screen display. While the portable electronic device is in a user-interface locked mode of an application with the touch screen display turned on, the device includes: means for displaying a locked-mode user interface for the application on the touch screen display; means for detecting a finger gesture on the touch screen display; and means for, in response to detecting the finger gesture on the touch screen display, performing a control operation in the application while maintaining display of the same locked-mode user interface for the application.

Thus, the invention provides simple, efficient and easy-to-use interfaces for operating a workout monitoring application on a portable electronic device with a touch-sensitive display. The invention also provides for control of an application (e.g., a workout support application or other application that provides audio) on a portable electronic device with a touch screen display with finger gestures while the application is in a user-interface locked mode of operation.

BRIEF DESCRIPTION OF THE DRAWINGS

For a better understanding of the aforementioned embodiments of the invention as well as additional embodiments thereof, reference should be made to the Description of Embodiments below, in conjunction with the following drawings in which like reference numerals refer to corresponding parts throughout the figures.

FIGS. 5A-5J are flow diagrams illustrating a method of operating a workout support application on a portable electronic device with a touch-sensitive display in accordance with some embodiments.

FIGS. 6A-6B are flow diagrams illustrating a method of monitoring and displaying post-workout-goal activity in accordance with some embodiments.

FIG. 7 is a flow diagram illustrating a method of initiating play of a powersong in accordance with some embodiments.

FIG. 8 is a flow diagram illustrating a method of initiating play of a next or previous audio file from a playlist in accordance with some embodiments.

FIG. 9 is a flow diagram illustrating a method of initiating play of a next or previous audio file from a playlist in accordance with some embodiments.

FIG. 10 is a flow diagram illustrating a method of controlling an application with finger gestures while the application is in a user-interface locked mode of operation in accordance with some embodiments.

DESCRIPTION OF EMBODIMENTS

Figure 1A:
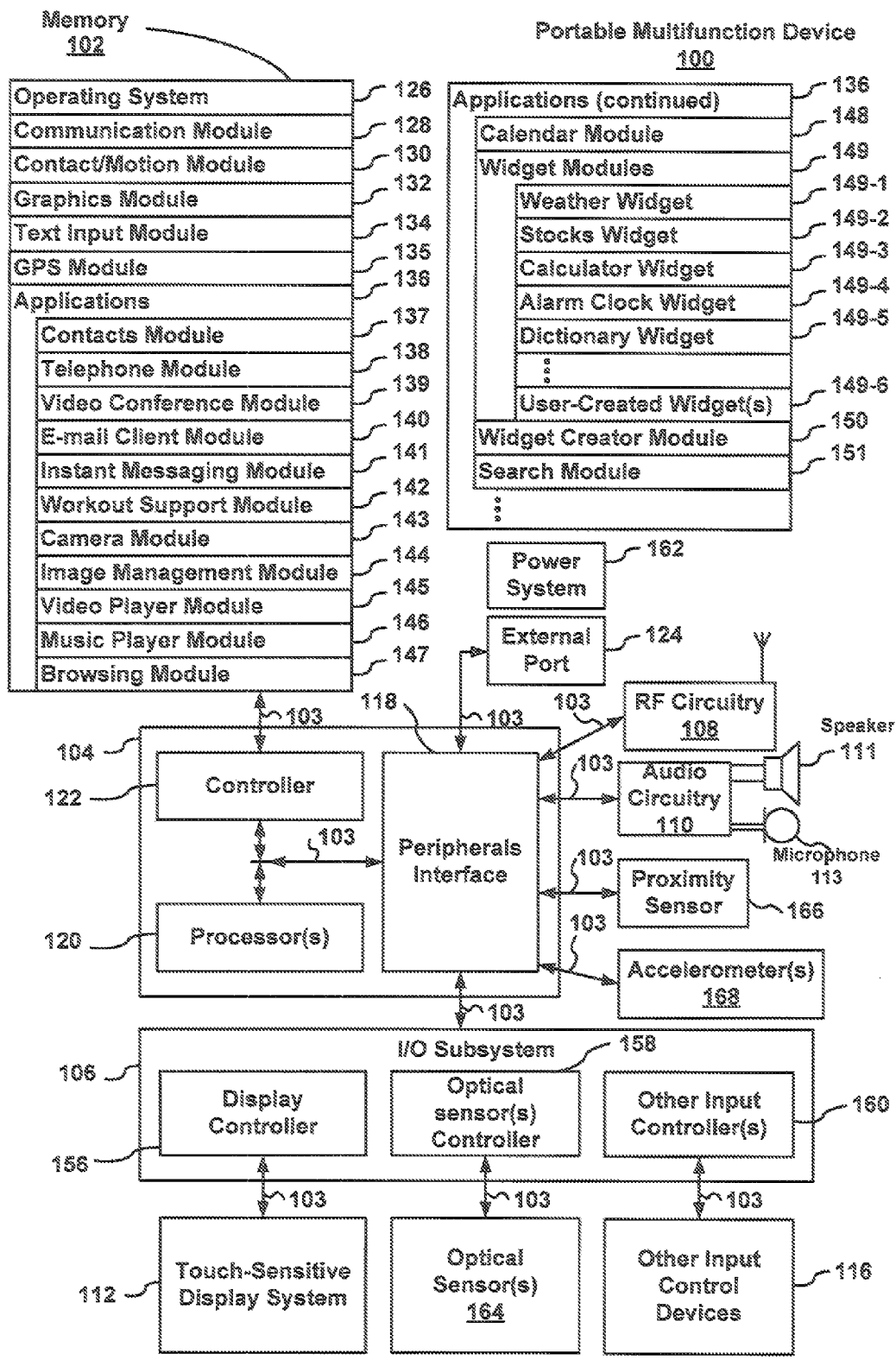
FIGS. 1A and 1B are block diagrams illustrating portable multifunction devices with touch-sensitive displays in accordance with some embodiments.

Reference will now be made in detail to embodiments, examples of which are illustrated in the accompanying drawings. In the following detailed description, numerous specific details are set forth in order to provide a thorough understanding of the present invention. However, it will be apparent to one of ordinary skill is the art that the present invention may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first gesture could be termed a second gesture, and, similarly, a second gesture could be termed a first gesture, without departing from the scope of the present invention.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Embodiments of a portable multifunction device, user interfaces for such devices, and associated processes for using such devices are described. In some embodiments, the device is a portable communications device such as a mobile telephone that also contains other functions, such as workout support, PDA, and/or music player functions.

The user interface may include a physical click wheel in addition to a touch screen or a virtual click wheel displayed on the touch screen. A click wheel is a user-interface device that may provide navigation commands based on an angular displacement of the wheel or a point of contact with the wheel by a user of the device. A click wheel may also be used to provide a user command corresponding to selection of one or more items, for example, when the user of the device presses down on at least a portion of the wheel or the center of the wheel. Alternatively, breaking contact with a click wheel image on a touch screen surface may indicate a user command corresponding to selection. For simplicity, in the discussion that follows, a portable multifunction device that includes a touch screen is used as an exemplary embodiment. It should be understood, however, that some of the user interfaces and associated processes may be applied to other portable devices.

In addition to the workout support application, the device may support a variety of other applications, such as one or more of the following: a telephone application, a video conferencing application, an e-mail application, an instant messaging application, a blogging application, a photo management application, a digital camera application, a digital video camera application, a web browsing application, a digital music player application, and/or a digital video player application.

The various applications that may be executed on the device may use at least one common physical user-interface device, such as the touch screen. One or more functions of the touch screen as well as corresponding information displayed on the device may be adjusted and/or varied from one application to the next and/or within a respective application. In this way, a common physical architecture (such as the touch screen) of the device may support the variety of applications with user interfaces that are intuitive and transparent.

The user interfaces may include one or more soft keyboard embodiments. The soft keyboard embodiments may include standard (QWERTY) and/or non-standard configurations of symbols on the displayed icons of the keyboard, such as those described in U.S. patent application Ser. Nos. 11/459,606, "Keyboards For Portable Electronic Devices," filed Jul. 24, 2006, and 11/459,615, "Touch Screen Keyboards For Portable Electronic Devices," filed Jul. 24, 2006, the contents of which are hereby incorporated by reference in their entirety. The keyboard embodiments may include a reduced number of icons (or soft keys) relative to the number of keys in existing physical keyboards, such as that for a typewriter. This may make it easier for users to select one or more icons in the keyboard, and thus, one or more corresponding symbols. The keyboard embodiments may be adaptive. For example, displayed icons may be modified in accordance with user actions, such as selecting one or more icons and/or one or more corresponding symbols. One or more applications on the portable device may utilize common and/or different keyboard embodiments. Thus, the keyboard embodiment used may be tailored to at least some of the applications. In some embodiments, one or more keyboard embodiments may be tailored to a respective user. For example, one or more keyboard embodiments may be tailored to a respective user based on a word usage history (lexicography, slang, individual usage) of the respective user. Some of the keyboard embodiments may be adjusted to reduce a probability of a user error when selecting one or more icons, and thus one or more symbols, when using the soft keyboard embodiments.

Figure 1B:
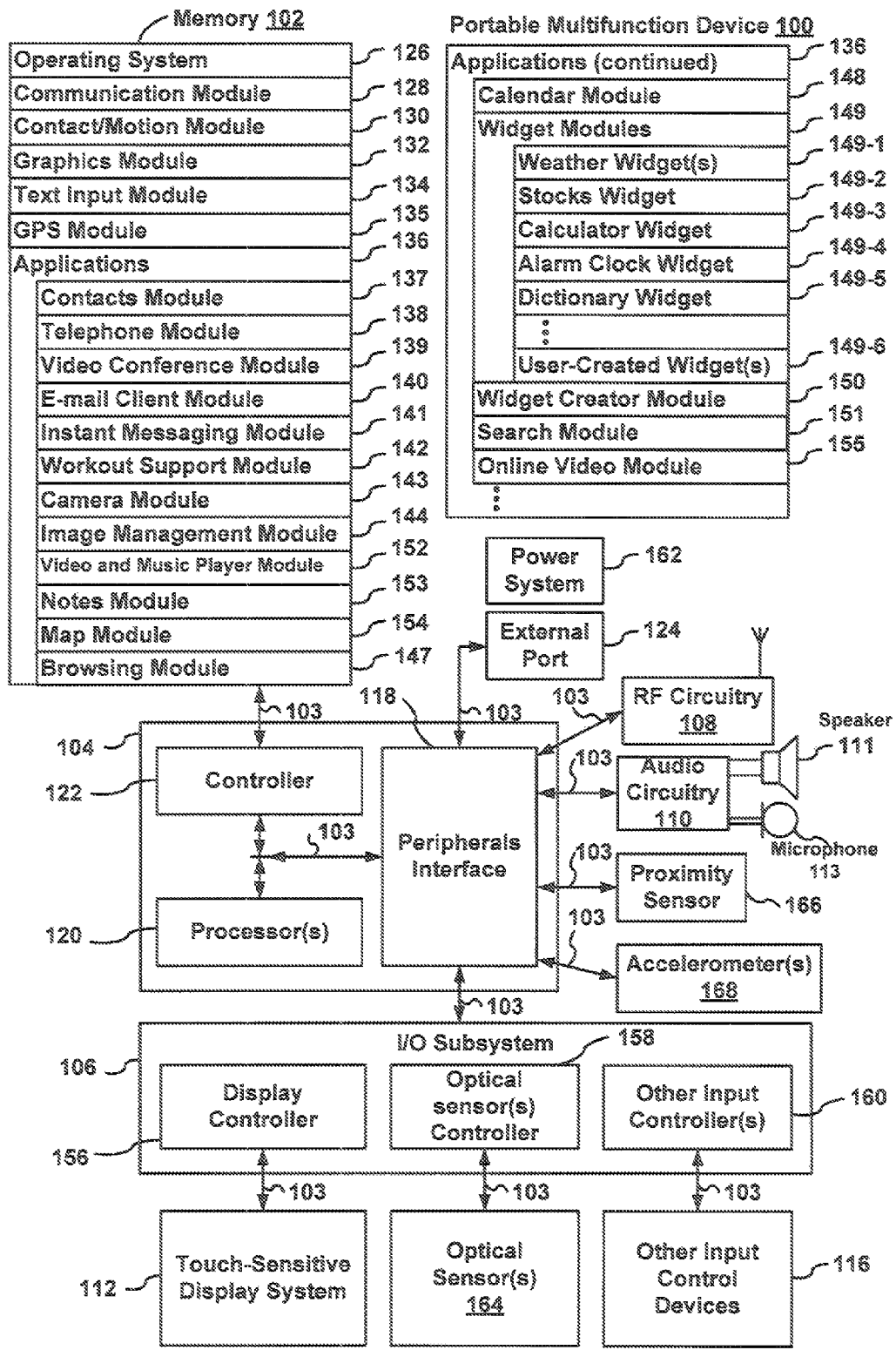

Attention is now directed towards embodiments of the device. FIGS. 1A and 1B are block diagrams illustrating portable multifunction devices 100 with touch-sensitive displays 112 in accordance with some embodiments. The touch-sensitive display 112 is sometimes called a "touch screen" for convenience, and may also be known as or called a touch-sensitive display system. The device 100 may include a memory 102 (which may include one or more computer readable storage mediums), a memory controller 122, one or more processing units (CPU's) 120, a peripherals interface 118, RF circuitry 108, audio circuitry 110, a speaker 111, a microphone 113, an input/output (I/O) subsystem 106, other input or control devices 116, and an external port 124. The device 100 may include one or more optical sensors 164. These components may communicate over one or more communication buses or signal lines 103.

It should be appreciated that the device 100 is only one example of a portable multifunction device 100, and that the device 100 may have more or fewer components than shown, may combine two or more components, or a may have a different configuration, or arrangement of the components. The various components shown in FIGS. 1A and 1B may be implemented in hardware, software or a combination of both hardware and software, including one or more signal processing and/or application specific integrated circuits.

Memory 102 may include high-speed random access memory and may also include non-volatile memory, such as one or more magnetic disk storage devices, flash memory devices, or other non-volatile solid-state memory devices. Access to memory 102 by other components of the device 100, such as the CPU 120 and the peripherals interface 118, may be controlled by the memory controller 122.

The peripherals interface 118 couples the input and output peripherals of the device to the CPU 120 and memory 102. The one or more processors 120 run or execute various software programs and/or sets of instructions stored in memory 102 to perform various functions for the device 100 and to process data.

In some embodiments, the peripherals interface 118, the CPU 120, and the memory controller 122 may be implemented on a single chip, such as a chip 104. In some other embodiments, they may be implemented on separate chips.

The RF (radio frequency) circuitry 108 receives and sends RF signals, also called electromagnetic signals. The RF circuitry 108 converts electrical signals to/from electromagnetic signals and communicates with communications networks and other communications devices via the electromagnetic signals. The RF circuitry 108 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 108 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth®, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

The audio circuitry 110, the speaker 111, and the microphone 113 provide an audio interface between a user and the device 100. The audio circuitry 110 receives audio data from the peripherals interface 118, converts the audio data to an electrical signal, and transmits the electrical signal to the speaker 111. The speaker 111 converts the electrical signal to human-audible sound waves. The audio circuitry 110 also receives electrical signals converted by the microphone 113 from sound waves. The audio circuitry 110 converts the electrical signal to audio data and transmits the audio data to the peripherals interface 118 for processing. Audio data may be retrieved from and/or transmitted to memory 102 and/or the RF circuitry 108 by the peripherals interface 118. In some embodiments, the audio circuitry 110 also includes a headset jack (e.g. 212, FIG. 2). The headset jack provides an interface between the audio circuitry 110 and removable audio input/output peripherals, such as output-only headphones or a headset with both output (e.g., a headphone for one or both ears) and input (e.g., a microphone).

The I/O subsystem 106 couples input/output peripherals on the device 100, such as the touch screen 112 and other input/control devices 116, to the peripherals interface 118. The I/O subsystem 106 may include a display controller 156 and one or more input controllers 160 for other input or control devices. The one or more input controllers 160 receive/send electrical signals from/to other input or control devices 116. The other input/control devices 116 may include physical buttons (e.g., push buttons, rocker buttons, etc.), dials, slider switches, joysticks, click wheels, and so forth. In some alternate embodiments, input controller(s) 160 may be coupled to any (or none) of the following: a keyboard, infrared port, USB port, and a pointer device such as a mouse. The one or more buttons (e.g., 208, FIG. 2) may include an up/down button for volume control of the speaker 111 and/or the microphone 113. The one or more buttons may include a push button (e.g., 206, FIG. 2). A quick press of the push button may disengage a lock of the touch screen 112 or begin a process that uses gestures on the touch screen to unlock the device, as described in U.S. patent application Ser. No. 11/322,549, "Unlocking a Device by Performing Gestures on an Unlock Image," filed Dec. 23, 2005, which is hereby incorporated by reference in its entirety. A longer press of the push button (e.g., 206) may turn power to the device 100 on or off. The user may be able to customize a functionality of one or more of the buttons. The touch screen 112 is used to implement virtual or soft buttons and one or more soft keyboards.

The touch-sensitive touch screen 112 provides an input interface and an output interface between the device and a user. The display controller 156 receives and/or sends electrical signals from/to the touch screen 112. The touch screen 112 displays visual output to the user. The visual output may include graphics, text, icons, video, and any combination thereof (collectively termed "graphics"). In some embodiments, some or all of the visual output may correspond to user-interface objects.

A touch screen 112 has a touch-sensitive surface, sensor or set of sensors that accepts input from the user based on haptic and/or tactile contact. The touch screen 112 and the display controller 156 (along with my associated modules and/or sets of instructions in memory 102) detect contact (and any movement or breaking of the contact) on the touch screen 112 and converts the detected contact into interaction with user-interface objects (e.g., one or more soft keys, icons, web pages or images) that are displayed on the touch screen. In an exemplary embodiment, a point of contact between a touch screen 112 and the user corresponds to a finger of the user.

The touch screen 112 may use LCD (liquid crystal display) technology, or LPD (light emitting polymer display) technology, although other display technologies may be used in other embodiments. The touch screen 112 and the display controller 156 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 112. In an exemplary embodiment, projected mutual capacitance sensing technology is used, such as that found in the iPhone® and iPod Touch® from Apple Computer, Inc. of Cupertino, Calif.

A touch-sensitive display in some embodiments of the touch screen 112 may be analogous to the multi-touch sensitive tablets described in the following U.S. Pat. Nos. 6,323,846 (Westerman et al.), 6,570,557 (Westerman et al.), and/or 6,677,932 (Westerman), and/or U.S. Patent Publication 2002/0015024A1, each of which is hereby incorporated by reference in its entirety. However, a touch screen 112 displays visual output from the portable device 100, whereas touch sensitive tablets do not provide visual output.

A touch-sensitive display in some embodiments of the touch screen 112 may be as described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen. Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

The touch screen 112 may have a resolution in excess of 100 dpi. In an exemplary embodiment, the touch screen has a resolution of approximately 160 dpi. The user may make contact with the touch screen 112 using any suitable object or appendage, such as a stylus, a finger, and so forth. In some embodiments, the user interface is designed to work primarily with finger-based contacts and gestures, which are much less precise than stylus-based input due to the larger area of contact of a finger on the touch screen. In some embodiments, the device translates the rough finger-based input into a precise pointer/cursor position of command for performing the actions desired by the user.

In some embodiments, in addition to the touch screen, the device 100 may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from the touch screen 112 or an extension of the touch-sensitive surface formed by the touch screen.

In some embodiments, the device 100 may include a physical or virtual click wheel as an input control device 116. A user may navigate among and interact with one or more graphical objects (henceforth referred to as icons) displayed in the touch screen 112 by rotating the click wheel or by moving a point of contact with the click wheel (e.g., where the amount of movement of the point of contact is measured by its angular displacement with respect to a center point of the click wheel). The click wheel may also be used to select one or more of the displayed icons. For example, the user may press down on at least a portion of the click wheel or an associated button. User commands and navigation commands provided by the user via the click wheel may be processed by an input controller 160 as well as one or more of the modules and/or sets of instructions in memory 102. For a virtual click wheel, the click wheel and click wheel controller may be part of the touch screen 112 and the display controller 156, respectively. For a virtual click wheel, the click wheel may be either an opaque or semitransparent object that appears and disappears on the touch screen display in response to user interaction with the device. In some embodiments, a virtual click wheel is displayed on the touch screen of a portable multifunction device and operated by user contact with the touch screen.

The device 100 also includes a power system 162 for powering the various components. The power system 162 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

The device 100 may also include one or more optical sensors 164. FIGS. 1A and 1B show an optical sensor coupled to an optical sensor controller 158 in I/O subsystem 106. The optical sensor 164 may include charge-coupled device (CCD) or complementary metal-oxide semiconductor (CMOS) phototransistors. The optical sensor 164 receives light from the environment, projected through one or more lens, and converts the light to data representing an image. In conjunction with an imaging module 143 (also called a camera module), the optical sensor 164 may capture still images or video. In some embodiments, an optical sensor is located on the back of the device 100, opposite the touch screen display 112 on the front of the device, so that the touch screen display may be used as a viewfinder for still and/or video image acquisition. In some embodiments, an optical sensor is located on the front of the device so that the user's image may be obtained for videoconferencing while the user views the other video conference participants on the touch screen display. In some embodiments, the position of the optical sensor 164 can be changed by the user (e.g., by rotating the lens and the sensor in the device housing) so that a single optical sensor 164 may be used along with the touch screen display for both video conferencing and still and/or video image acquisition.

The device 100 may also include one or more proximity sensors 166. FIGS. 1A and 1B show a proximity sensor 166 coupled to the peripherals interface 118. Alternately, the proximity sensor 166 may be coupled to an input controller 160 in the I/O subsystem 106. The proximity sensor 166 may perform as described in U.S. patent application Ser. Nos. 11/241,839, "Proximity Detector In Handheld Device"; 11/240,788, "Proximity Detector In Handheld Device"; 11/620,702, "Using Ambient Light Sensor To Augment Proximity Sensor Output"; 11/586,862, "Automated Response To And Sensing Of User Activity In Portable Devices"; and 11/638,251, "Methods And Systems For Automatic Configuration Of Peripherals," which are hereby incorporated by reference in their entirety. In some embodiments, the proximity sensor turns off and disables the touch screen 112 when the multifunction device is placed near the user's ear (e.g., when the user is making a phone call). In some embodiments, the proximity sensor keeps the screen off when the device is in the user's pocket, purse, or other dark area to prevent unnecessary battery drainage when the device is a locked state.

The device 100 may also include one or more accelerometers 168. FIGS. 1A and 1B show an accelerometer 168 coupled to the peripherals interface 118. Alternately, the accelerometer 168 may be coupled to an input controller 160 in the I/O subsystem 106. The accelerometer 168 may perform as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are which are incorporated by reference herein in their entirety. In some embodiments, information is displayed on the touch screen display in a portrait view or a landscape view based on an analysis of data received from the one or more accelerometers.

In some embodiments, the software components stored in memory 102 may include an operating system 126, a communication module (or set of instructions) 128, a contact/motion module (or set of instructions) 130, a graphics module (or set of instructions) 132, a text input module (or set of instructions) 134, a Global Positioning System (GPS) module (or set of instructions) 135, and applications (or set of instructions) 136.

The operating system 126 (e.g., Darwin®, RTXC, LINUX, UNIX, OS X, WINDOWS, or an embedded operating system such as VxWorks®) includes various software components and/or drivers for controlling and managing general system tasks (e.g., memory management, storage device control, power management, etc.) and facilitates communication between various hardware and software components.

The communication module 128 facilitates communication with other devices over one or more external ports 124 and also includes various software components for handling data received by the RF circuitry 108 and/or the external port 124. The external port 124 (e.g., Universal Serial Bus (USB), FIREWIRE®, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with the 30-pin connector used on iPod (trademark of Apple Computer, Inc.) devices.

The contact/motion module 130 may detect contact with the touch screen 112 (in conjunction with the display controller 156) and other touch sensitive devices (e.g., a touchpad or physical click wheel). The contact/motion module 130 includes various software components for performing various operations related to detection of contact, such as determining if contact has occurred, determining if there is movement of the contact and tracking the movement across the touch screen 112, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). In some embodiments, the contact/motion module 130 and the display controller 156 also detects contact on a touchpad. In some embodiments, the contact/motion module 130 and the controller 160 detects contact on a click wheel.

The graphics module 132 includes various known software components for rendering and displaying graphics on the touch screen 112, including components for changing the intensity of graphics that are displayed. As used herein, the term "graphics" includes any object that can be displayed to a user, including without limitation text, web pages, icons (such as user-interface objects including soft keys), digital images, videos, animations and the like.

The text input module 134, which may be a component of graphics module 132, provides soft keyboards for entering text in various applications (e.g., contacts 137, e-mail 140, IM 141, workout support 142, browser 147, and any other application that needs text input).

The GPS module 135 determines the location of the device and provides this information for use in various applications (e.g., to telephone 138 for use in location-based dialing, to camera 143 as picture/video metadata, and to applications that provide location-based services such as weather widgets, local yellow page widgets, and map/navigation widgets).

The applications 136 may include the following modules (or sets of instructions), or a subset or superset thereof:
  a contacts module 137 (sometimes called an address book or contact list);
  a telephone module 138;
  a video conferencing module 139;
  an e-mail client module 140;
  an instant messaging (IM) module 141;
  a workout support module 142;
  a camera module 143 for still and/or video images;
  an image management module 144;
  a video player module 145;
  a music player module 146;
  a browser module 147;
  a calendar module 148;
  widget modules 149, which may include weather widget 149-1, stocks widget 149-2, calculator widget 149-3, alarm clock widget 149-4, dictionary widget 149-5, and other widgets obtained by the user, as well as user-created widgets 149-6;
  widget creator module 150 for making user-created widgets 149-6;
  search module 151;
  video and music player module 152, which merges video player module 145 and music player module 146;
  notes module 153;
  map module 154; and/or
  online video module 155.

Examples of other applications 136 that may be stored in memory 102 include other word processing applications, JAVA-enabled applications, encryption, digital rights management, voice recognition, and voice replication.

In conjunction with touch screen 112, display controller 156, contact module 130, graphics module 132, and text input module 134, the contacts module 137 may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference 139, e-mail 140, or IM 141; and so forth.

In conjunction with RF circuitry 108, audio circuitry 110, speaker 111, microphone 113, touch screen 112, display controller 156, contact module 130, graphics module 132, and text input module 134, the telephone module 138 may be used to enter a sequence of characters corresponding to a telephone number, access one or more telephone numbers in the address book 137, modify a telephone number that has been entered, dial a respective telephone number, conduct a conversation and disconnect or hang up when the conversation is completed. As noted above, the wireless communication may use any of a plurality of communications standards, protocols and technologies.

In conjunction with RF circuitry 108, audio circuitry 110, speaker 111, microphone 113, touch screen 112, display controller 156, optical sensor 164, optical sensor controller 158, contact module 130, graphics module 132, text input module 134, contact list 137, and telephone module 138, the videoconferencing module 139 may be used to initiate, conduct, and terminate a video conference between a user and one or more other participants.

In conjunction with RF circuitry 108, touch screen 112, display controller 156, contact module 130, graphics module 132, and text input module 134, the e-mail client module 140 may be used to create, send, receive, and manage e-mail. In conjunction with image management module 144, the e-mail module 140 makes it very easy to crests and send e-mails with still or video images taken with camera module 143.

In conjunction with RF circuitry 108, touch screen 112, display controller 156, contact module 130, graphics module 132, and text input module 134, the instant messaging module 141 may be used to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages and to view received instant messages. In some embodiments, transmitted and/or received instant messages may include graphics, photos, audio files, video files and/or other attachments as are supported in a MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact module 130, graphics module 132, text input module 134, GPS module 135, map module 154, and music player module 146, the workout support module 142 may be used to create workouts (e.g., with time, distance, and/or calorie burning goals); communicate with workout sensors (sports devices); receive workout sensor data; calibrate sensors used to monitor a workout; select and play music for a workout; and display, store and transmit workout data.

In conjunction with touch screen 112, display controller 156, optical sensor(s) 164, optical sensor controller 158, contact module 130, graphics module 132, and image management module 144, the camera module 143 may be used to capture still images or video (including a video stream) and store them into mentor 102, modify characteristics of a still image or video, or delete a still image or video from memory 102.

In conjunction with touch screen 112, display controller 156, contact module 130, graphics module 132, text input module 134, and camera module 143, the image management module 144 may be used to arrange, modify or otherwise manipulate, label, delete, present (e.g., in a digital slide show or album), and store still and/or video images.

In conjunction with touch screen 112, display controller 156, contact module 130, graphics module 132, audio circuitry 110, and speaker 111, the video player module 145 may be used to display, present or otherwise play back videos (e.g., on the touch screen or on an external, connected display via external port 124).

In conjunction with touch screen 112, display system controller 156, contact module 130, graphics module 132, audio circuitry 110, speaker 111, RF circuitry 108, and browser module 147, the music player module 146 allows the user to download and play back recorded music and other sound files stored in one or more file formats, such as MP3 or AAC files. In some embodiments, the device 100 may include the functionality of an MP3 player, such as an iPod (trademark of Apple Computer, Inc.).

In conjunction with RF circuitry 108, touch screen 112, display system controller 156, contact module 130, graphics module 132, and text input module 134, the browser module 147 may be used to browse the Internet, including searching, linking to, receiving, and displaying web pages or portions thereof, as well as attachments and other files linked to web pages.

In conjunction with RF circuitry 108, touch screen 112, display system controller 156, contact module 130, graphics module 132, text input module 134, e-mail module 140, and browser module 147, the calendar module 148 may be used to create, display, modify, and store calendars and data associated with calendars (e.g., calendar entries, to do lists, etc.).

In conjunction with RF circuitry 108, touch screen 112, display system controller 156, contact module 130, graphics module 132, text input module 134, and browser module 147, the widget modules 149 are mini-applications that may be downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript® file. In some embodiments, a widget includes an XML (Extensible Markup Language) file and a JavaScript® file (e.g., Yahoo!® Widgets).

In conjunction with RF circuitry 108, touch screen 112, display system controller 156, contact module 130, graphics module 132, text input module 134, and browser module 147, the widget creator module 150 may be used by a user to create widgets (e.g., turning a user-specified portion of a web page into a widget).

In conjunction with touch screen 112, display system controller 156, contact module 130, graphics module 132, and text input module 134, the search module 151 may be used to search for text, music, sound, image, video, and/or other files in memory 102 that match one or more search criteria (e.g., one or more user-specified search terms).

In conjunction with touch screen 112, display controller 156, contact module 130, graphics module 132, and text input module 134, the notes module 153 may be used to create and manage notes, to do lists, and the like.

In conjunction with RF circuitry 108, touch screen 112, display system controller 156, contact module 130, graphics module 132, text input module 134, GPS module 135, and browser module 147, the map module 154 may be used to receive, display, modify, and store maps and data associated with maps (e.g., driving directions; data on stores and other points of interest at or near a particular location; and other location-based data).

In conjunction with touch screen 112, display system controller 156, contact module 130, graphics module 132, audio circuitry 110, speaker 111, RF circuitry 108, text input module 134, e-mail client module 140, and browser module 147, the online video module 155 allows the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the content of which is hereby incorporated by reference in its entirety.

Each of the above identified modules and applications correspond to a set of instructions for performing one or more functions described above. These modules (i.e., sets of instructions) need not be implemented as separate software programs, procedures or modules, and thus various subsets of these modules may be combined or otherwise rearranged in various embodiments. For example, video player module 145 may be combined with music player module 146 into a single module (e.g., video and music player module 152, FIG. 1B). In some embodiments, memory 102 may store a subset of the modules and data structures identified above. Furthermore, memory 102 may store additional modules and data structures not described above.

In some embodiments, the device 100 is a device where operation of a predefined set of functions on the device is performed exclusively through a touch screen 112 and/or a touchpad. By using a touch screen and/or a touchpad as the primary input/control device for operation of the device 100, the number of physical input/control devices (such as push buttons, dials, and the like) on the device 100 may be reduced.

The predefined set of functions that may be performed exclusively through a touch screen and/or a touchpad include navigation between user interfaces. In some embodiments, the touchpad, when touched by the user, navigates the device 100 to a main, home, or root menu from any user interface that may be displayed on the device 100. In such embodiments, the touchpad may be referred to as a "menu button." In some other embodiments, the menu button may be a physical push button or other physical input/control device instead of a touchpad.

Figure 2:
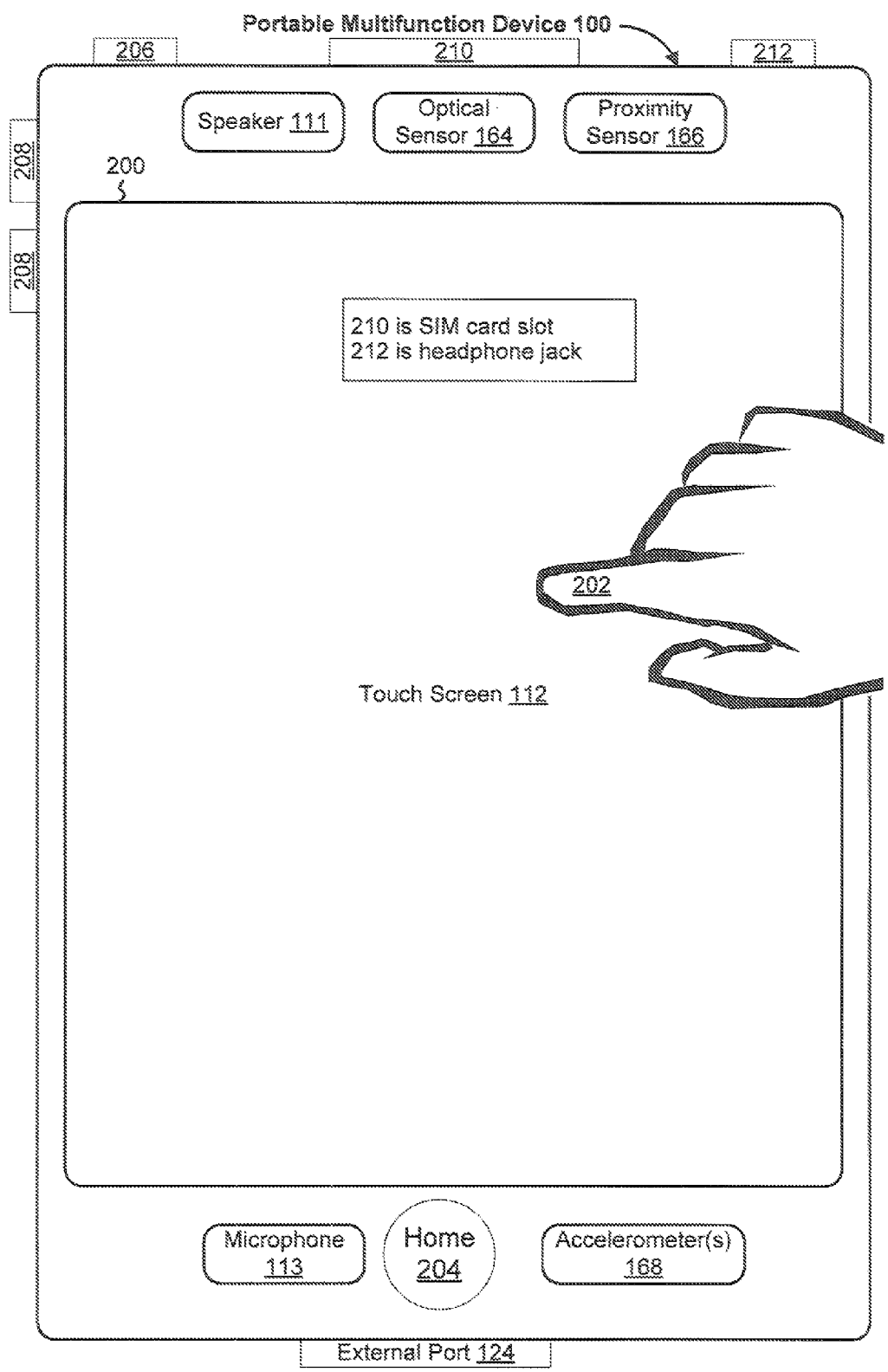
FIG. 2 illustrates a portable multifunction device having a touch screen in accordance with some embodiments.

FIG. 2 illustrates a portable multifunction device 100 having a touch screen 112 in accordance with some embodiments. The touch screen may display one or more graphics within user interface (UI) 200. In this embodiment, as well as others, a user may select one or more of the graphics by making contact or touching the graphics, for example, with one or more fingers 202 (not drawn to scale in the figure). In some embodiments, selection of one or more graphics occurs when the user breaks contact with the one or more graphics. In some embodiments, the contact may include a gesture, such as one or more taps, one or more swipes (from left to right, right to left, upward and/or downward) and/or a rolling of a finger (from right to left, left to right, upward and/or downward) that has made contact with the device 100. In some embodiments, inadvertent contact with a graphic may not select the graphic. For example, a swipe gesture that sweeps over an application icon may not select the corresponding application when the gesture corresponding to selection is a tap.

The device 100 may also include one or more physical buttons, such as "home" or menu button 204. As described previously, the menu button 204 may be used to navigate to any application 136 in a set of applications that may be executed on the device 100. Alternatively, in some embodiments, the menu button is implemented as a soft key in a GUI in touch screen 112.

In one embodiment, the device 100 includes a touch screen 112, a menu button 204, a push button 206 for powering the device on/off and locking the device, volume adjustment button(s) 208, a Subscriber Identity Module (SIM) card slot 210, a head set jack 212, and a docking/charging external port 124. The push button 206 may be used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, the device 100 also may accept verbal input for activation or deactivation of some functions through the microphone 113.

Attention is now directed towards an exemplary embodiment of a workout and sports monitoring system and associated processes that may be implemented on a portable multifunction device 100.

Figure 3:
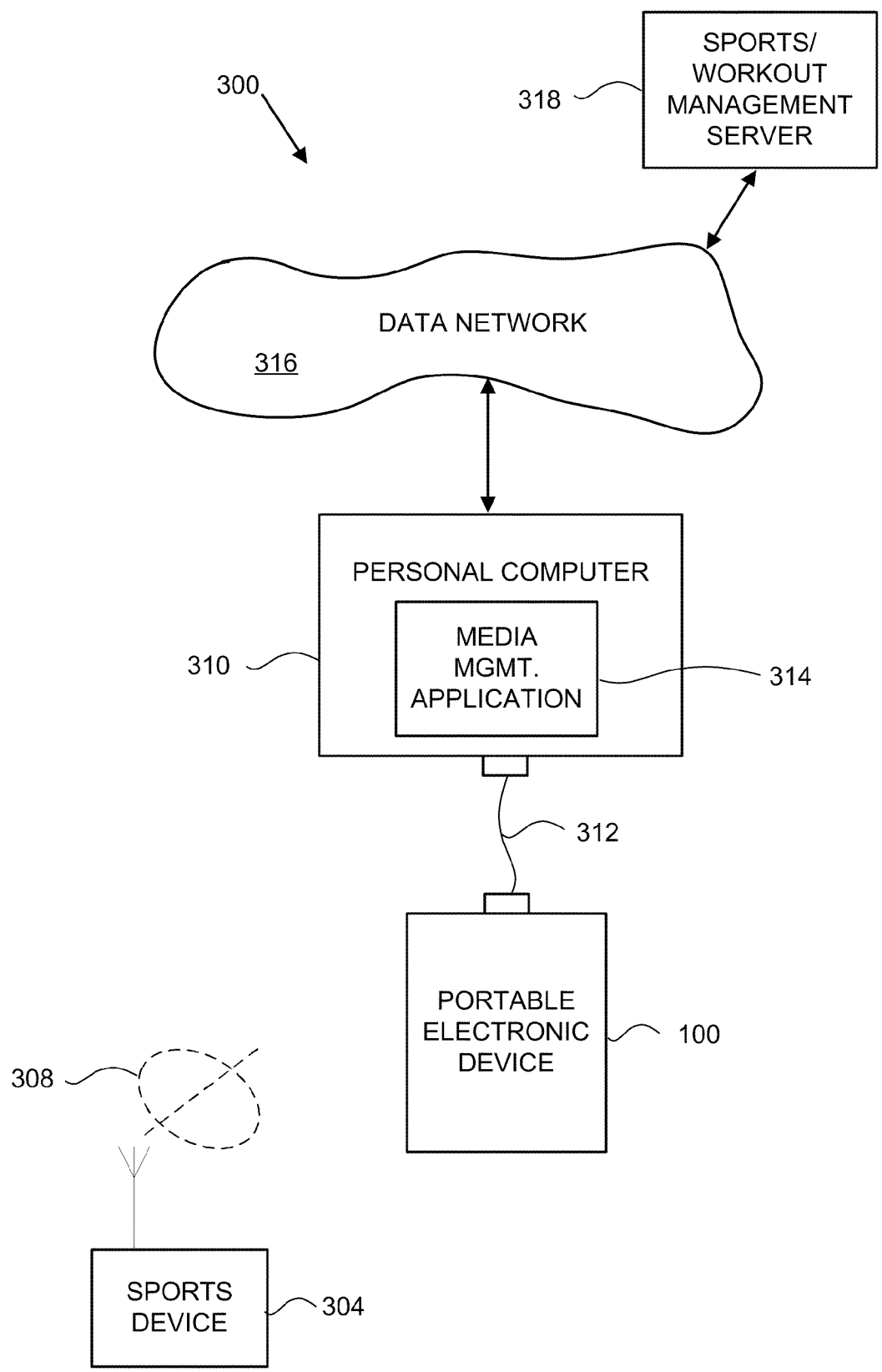
FIG. 3 illustrates an exemplary block diagram of a sports/workout monitoring system in accordance with some embodiments.

FIG. 3 is a block diagram of a sports/workout monitoring system 300 according to one embodiment of the invention. The monitoring system 300 is an electronic system that enables sports/workout related information to be acquired, stored, analyzed, presented and shared.

The sports/workout monitoring system 300 includes a portable electronic device 100. The portable electronic device 100 is capable of storing and playing media for its user. For example, the portable electronic device 100 can output (e.g., play) audio or video. The sports/workout monitoring system 300 also includes a sports device 304. The sports device 304 is, for example, a pedometer, a heart rate monitor, etc. The sports device 304 includes one or more sensors that acquire sports/workout related data.

The sports device 304 also includes wireless transmission capability so that the sports/workout related data can be transmitted to the portable electronic device 100. The portable electronic device 100 includes a wireless transceiver so that the portable electronic device 100 can receive the sports/workout related data being transmitted by the sports device 304 by way of a wireless connection through a personal wireless network 308. The portable electronic device 100 can then operate to process and store the sports/workout related data at the portable electronic device 100.

The sports/workout monitoring system 300 may also include a personal computer 310. The portable electronic device 100 can be electrically connected to the personal computer 310 by way of a cable 312. The cable 312 may, for example, be a Firewire or USB cable. Alternatively, the cable 312 may be replaced with a wireless link. Although the portable electronic device 100 is not normally electrically connected to the personal computer 310, the electrical connection when present facilitates information exchange between the portable electronic device 100 and the personal computer 310.

The personal computer 310 includes a media management application 314. The media management application 314, in one embodiment, can not only manage the media assets stored on the personal computer 310, but can also store and manage sports/workout related data. In one embodiment, the media management application 314 can operate to cause the sports/workout related data stored on the portable electronic device 100 to be copied to the personal computer 310. Thereafter, the sports/workout related data can be analyzed at the personal computer 310 and/or made available to the user of the personal computer 310. In addition, the sports monitoring system 300 can facilitate the portable electronic device 100 and/or the personal computer 310 coupling to a data network 316. The data network 316 can represent a global or wide area network, such as the World Wide Web (or the Internet). When the personal computer 310 is coupled to the data network 316, the sports/workout related data present at the personal computer 310 can be transferred to a sports/workout management server 318. Similarly, when the portable electronic device 100 is coupled to the data network 316, the sports/workout related data present at the portable electronic device 100 can be transferred to the sports/workout management server 318. At the sports/workout management server 318, the sports/workout related data can be former analyzed and/or processed to facilitate usefulness of the data. The sports/workout management server 318 supports storage and analysis of sports/workout related data from a large number of different portable electronic devices and/or personal computers. Hence, the sports/workout management server 318 can also compare the sports/workout related data from different users. The sports/workout management server 318 can also provide a website that can be accessed by a network browser operating on the personal computer 310 or other computing device to access sports related information or other information made available via the website. The website may also be accessed by a browser 147 or workout support application 142 operating on the portable electronic device 100.

The sports/workout monitoring system 300 can also support one or more remote controllers (not shown). A remote controller can also communicate with portable electronic device 100. The remote controller may require it be paired or linked with the portable electronic device 100.

The sports device 304 illustrated in FIG. 3 can take a variety of different forms. In one embodiment, the sports device is a sensor-based device, such as a pedometer.

Additional description of the sports/workout monitoring system 300 can be found in U.S. patent application Ser. Nos. 11/439,523, "Portable Media Device With Workout Support"; 11/585,721, "Calibration Techniques for Activity Sensing Devices"; and 11/439,521, "Communication Protocol For Use with Portable Electronic Devices," which are hereby incorporated by reference in herein their entirety.

FIGS. 4A-4FF illustrate exemplary user interfaces for a workout support application 142 running on a portable electronic device 100 equipped with a touch-sensitive display 112 in accordance with some embodiments. The workout support application interfaces shown here are merely illustrative embodiments. An overview of these figures is provided here.

Figure 4A:
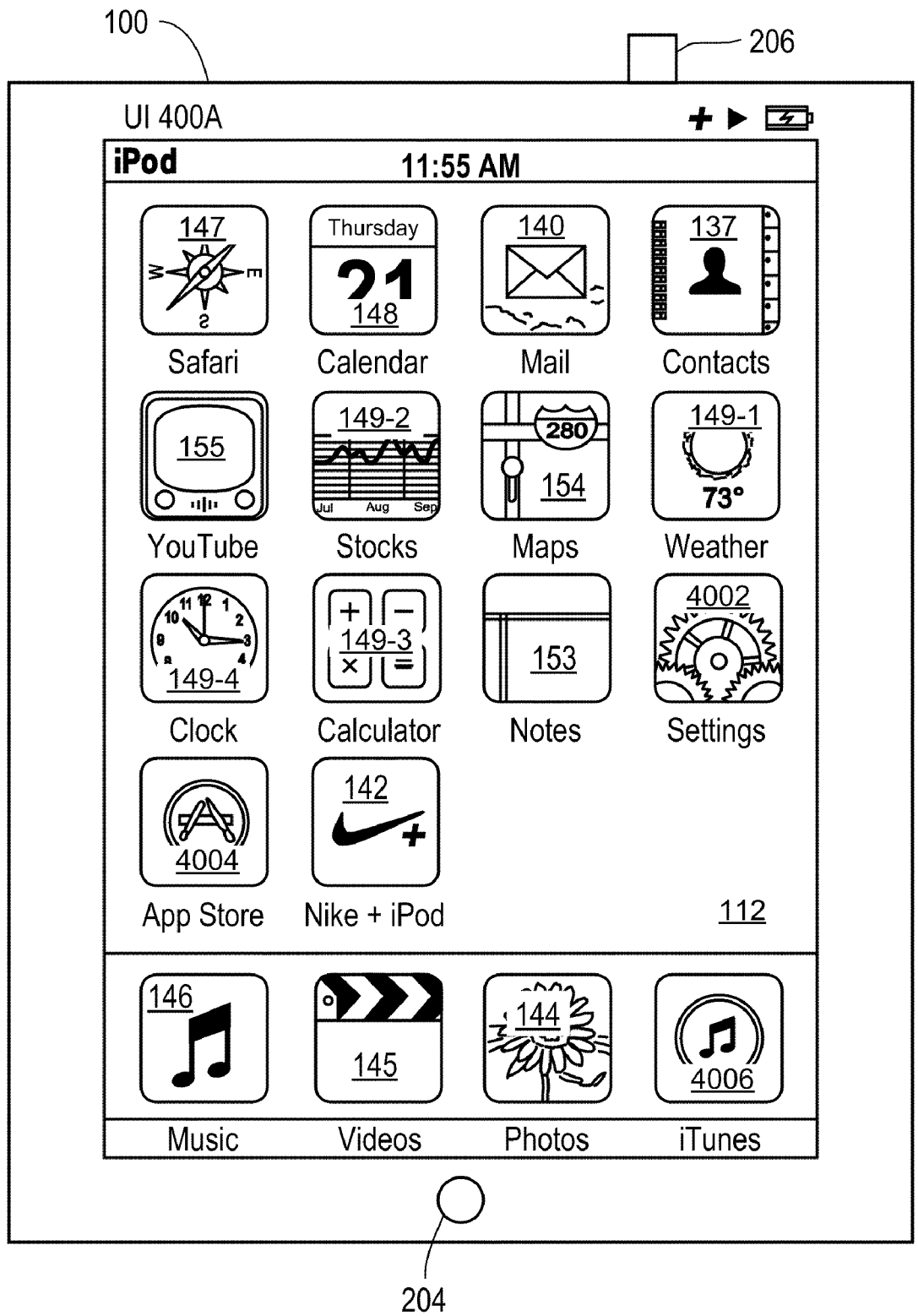
FIGS. 4A-4FF illustrate exemplary user interfaces for a workout support application running on a portable electronic device equipped with a touch-sensitive display in accordance with some embodiments.

FIG. 4A illustrates a user interface 400A on a portable multifunction device 100 with a touch screen 112. As depicted in this example, multiple applications are made available for users by activation of corresponding application icons, such as icons for a browser 147, calendar 148, email 140, contacts 137, online video 155, stocks 149-2, map 154, weather 149-1, clock 149-4, calculator 149-3, notes 153, workout support 142, music player 146, video player 145, and image management 144, as well as icons to access device settings 4002, an application store 4004, and a music/video/media content store 4006. Of particular interest here is the icon for the workout support application 142 (labeled in the illustrative figure as "Nike+iPod®").

Figure 4B:
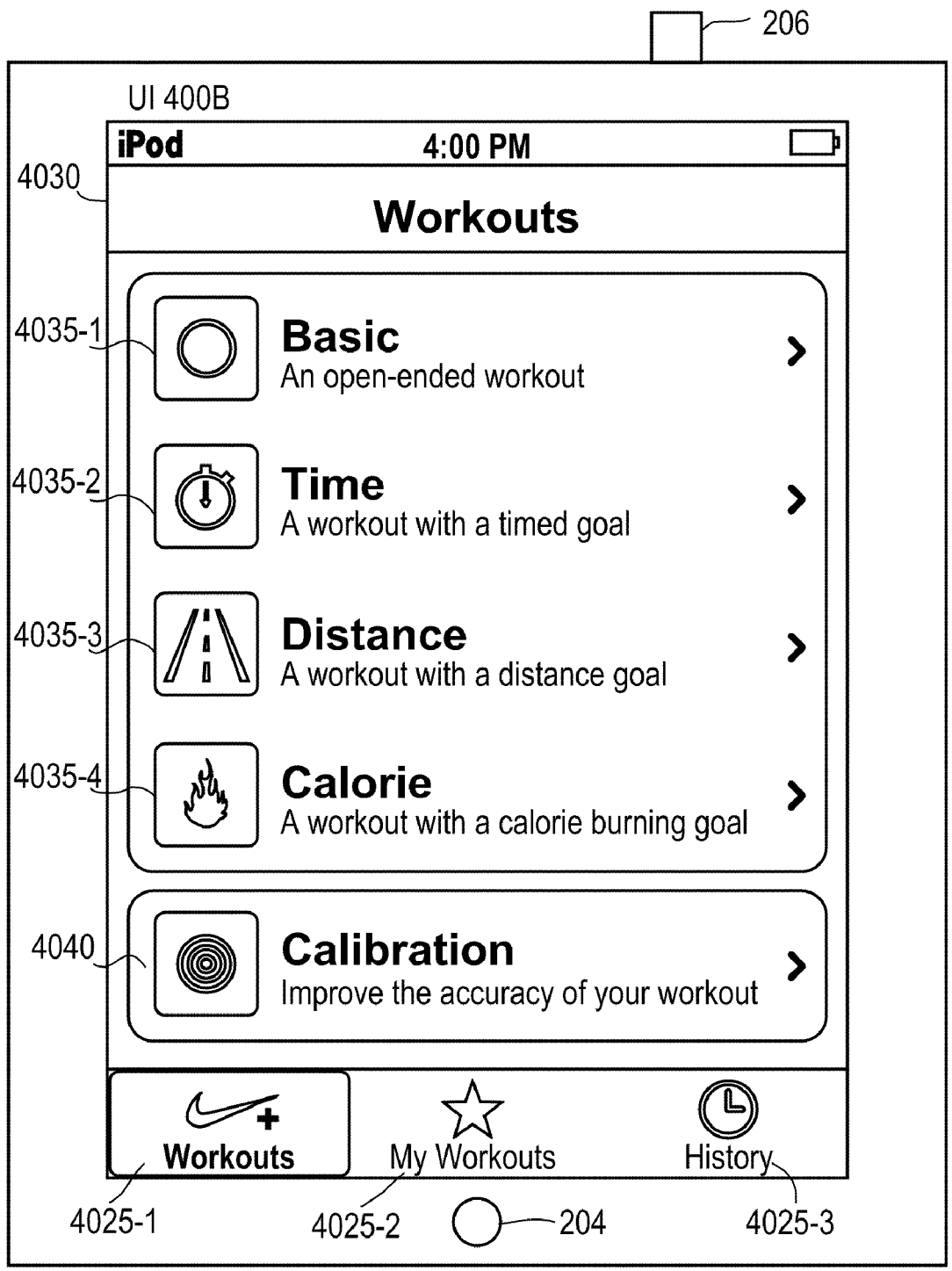

FIG. 4B illustrates an exemplary workout support application user interface, UI 400B. In this example, UI 400B includes a plurality of top-level user-interface screen icons 4025-1, 4025-2, and 4025-3 for the workout support application 142, which permit a user to direct the application to display the corresponding workout support user-interface screens. For example, in response to a finger tap gesture on top-level user-interface screen icon 4025-2, the application 142 will display a top-level user-interface screen entitled "My Workouts" (UI 400M, FIG. 4M). In FIG. 4B, top-level user-interface screen icon 4025-1 is selected and visually highlighted, while top-level user-interface screen icons 4025-2 and 4035-3 are grayed out. In some embodiments, as a further indication to the user of which state the application is in, screen title 4030 can be configured to display text corresponding to the currently active top-level user-interface screen (e.g., display the same text in screen title 4030 as the currently selected top-level user-interface screen selection 4025). Also depicted in FIG. 4B is a plurality of workout type selection icons 4035. In this example, workout type selection icons 4035-1, 4035-2, 4035-3, and 4035-4 are available to permit a user to select, create, and save different workout types, such as: 1) a basic workout, which is open-ended (4035-1); 2) elapsed time, which is a workout with a timed goal (4035-2); 3) distance traveled, which is a workout with a distance goal (4035-3); and 4) estimated calories burned, which is a workout with a calorie burning goal (4035-4). Finally, FIG. 4B also depicts a calibration request icon 4040 that initiates display of a user interface calibrating data collected from user workouts.

Figure 4C:
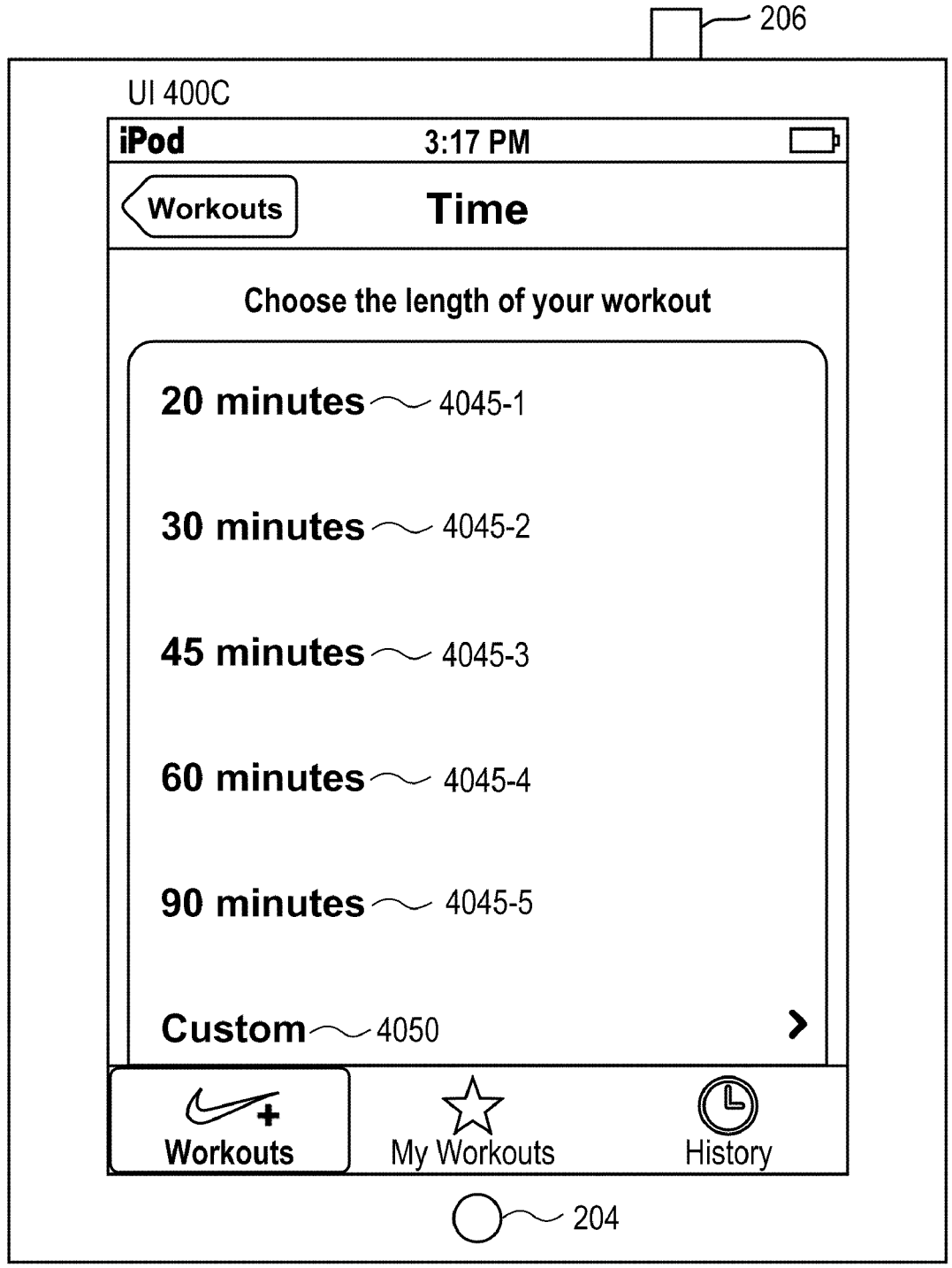
Figure 4D:
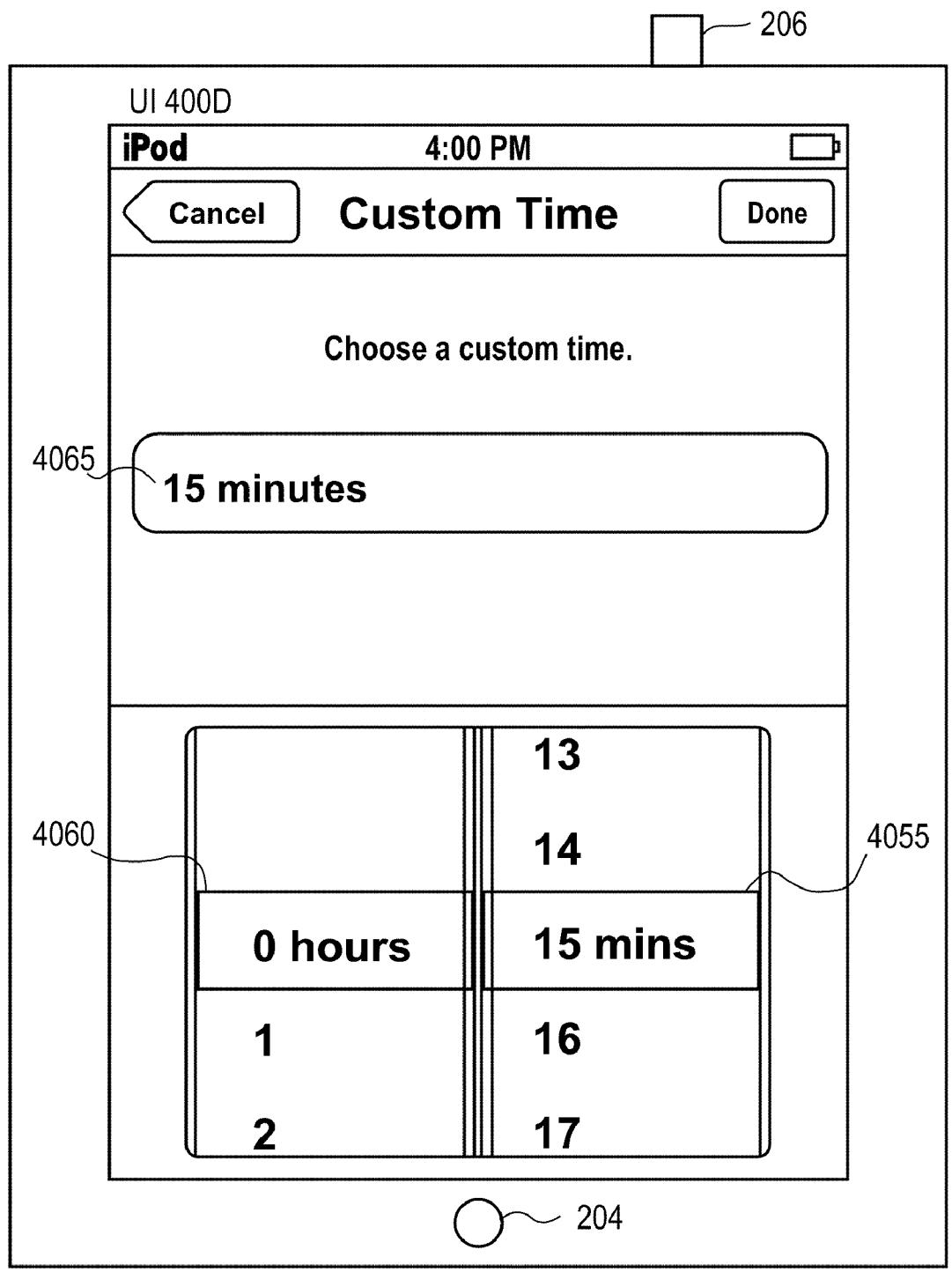

FIGS. 4C and 4D illustrate example workout support application UIs 400C and 400D, which permit a user to select from different lengths of time to workout. UI 400C is displayed in response to detection of a finger gesture on workout type selection icon 4035-2 (FIG. 4B). Exemplary time values may include 20 minutes (4045-1), 30 minutes (4045-2), 45 minutes (4045-3), 60 minutes (4045-4), and 90 minutes (4045-5) (FIG. 4C), and can be selected in response to detecting a user selection of a workout time icon 4045 corresponding to the desired workout time. For example, in FIG. 4C, workout time icon 4045-3 would be used to select a workout time of 45 minutes. In response to detecting a user selection of custom workout time icon 4050, UI 400D (FIG. 4D) is displayed to allow input of a workout time not provide for in the default workout time icons 4045. UI 400D (FIG. 4D) illustrates a user-input mechanism permitting users to specify custom values for workout types. When setting the numeric values for a workout type, e.g., specifying hours and minutes for an elapsed time workout, a mechanism may be used like that described in U.S. patent application Ser. No. 11/968,051, "System, Method, and Graphical User Interface for Inputting Date and Time Information on a Portable Multifunction Device," filed Dec. 31, 2007, the contents of which are incorporated by reference in their entirety. UI 400D provides at least one input mechanism to allow user-input of portions of a time segment. In this example, minutes input mechanism 4055 and hours input mechanism 4060 are shown. Other embodiments may include input mechanisms for additional measurements of time such as days and seconds. In response to user-input of a valid time selection, the time selected field 4065 is populated with the value corresponding to the valid time selection.

UI 400E and UI 400F (FIGS. 4E and 4F) illustrate examples of workout support application screens that permit a user to select different workout distances. These UIs operate in an analogous manner to UI 400C and UI 400D (FIGS. 4C and 4D), described above.

UI 400G and UI 400H (FIGS. 4G and 4H) illustrate examples of workout support application screens that permit a user to select a calorie burning goal. These UIs operate in an analogous manner to UI 400C and UI 400D (FIGS. 4C and 4D), described above.

Exemplary UIs 400I and 400I (FIGS. 4I and 4J) permit a user to select music to play during a workout. UI 400I (FIG. 4I) includes three music selection icons: playlist selection icon 4085; shuffle selection icon 4090; and no music selection icon 4095. In response to detecting a user selection of playlist selection icon 4085, UI 400J (FIG. 4J) is displayed to permit a user to select which playlist to use during a given workout, e.g., a "Driving Mix" playlist, a "Summer Songs" playlist, or a "Workout Music" playlist.

UI 400K (FIG. 4K) permits a user to calibrate the sports device to increase accuracy of the data collected about user workouts. As depicted in UI 400K, walk calibration icon 4105 and run calibration icon 4110 may be provided for displaying separate calibration UIs for walking and running.

UI 400L (FIG. 4L) provides a summary of a completed workout. In some embodiments, the following summary data is displayed: accumulated distance 4115 (here, displaying 0.62 miles), time elapsed 4120 (here, displaying 4:37), average pace 4125 (here, displaying 7'27" per mile), and estimated calories burned 4130 (here, displaying 136). Further, some embodiments may present an option to calibrate a completed workout to a known distance traveled so as to increase accuracy. Following completion of a workout, the system determines if there was a sufficient number of steps taken at a relatively consistent pace. If so, the system indicates the workout can be used for calibration, and presents a calibration icon 4135, which if activated (e.g., by a finger gesture), will cause the workout support application 142 to perform calculations to calibrate the sports device 304 (e.g., calibrate the stride length for distance calculations) and increase accuracy of the calculated summary workout data.

Figure 4E:
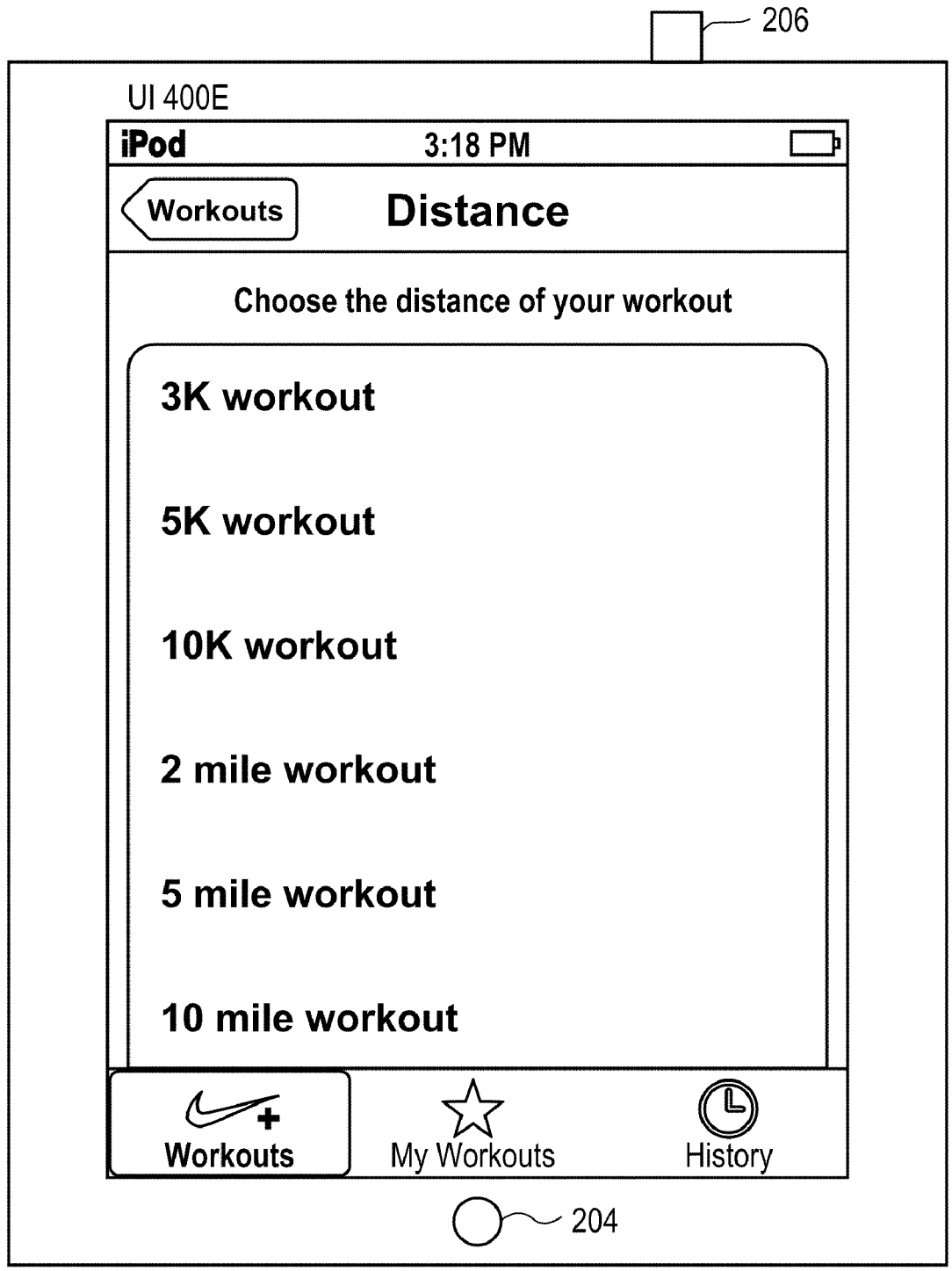
Figure 4F:
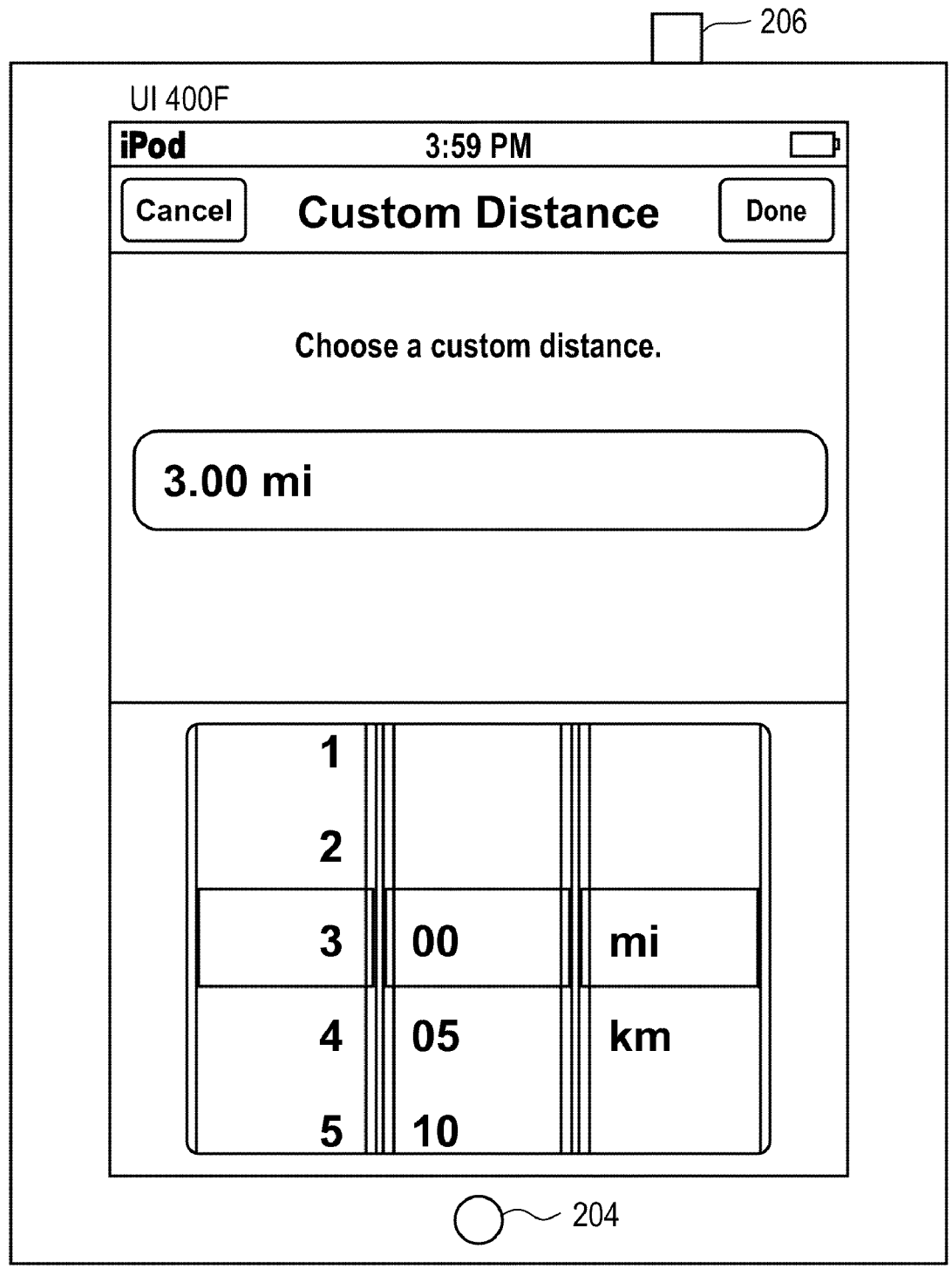
Figure 4G:
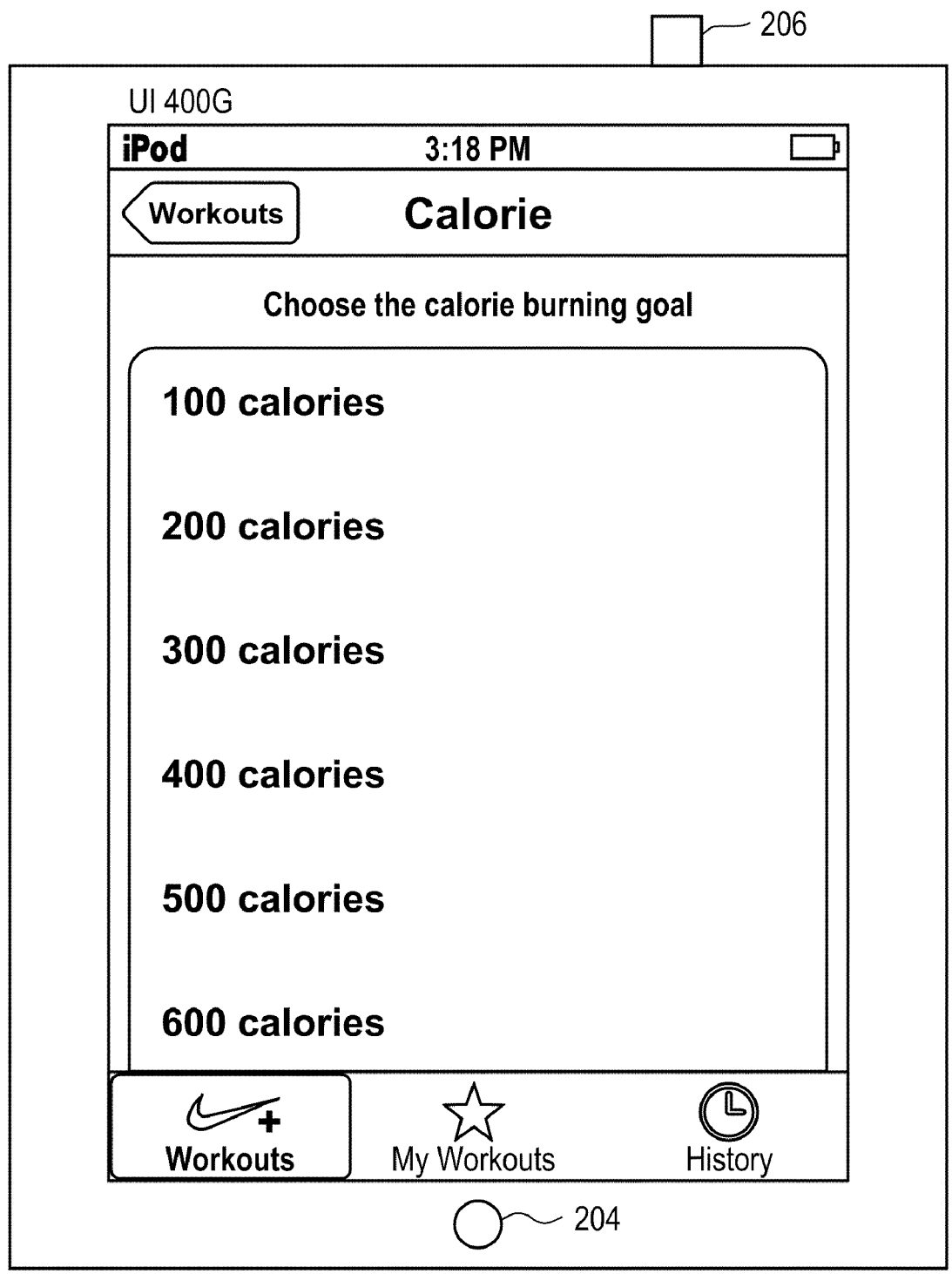
Figure 4H:
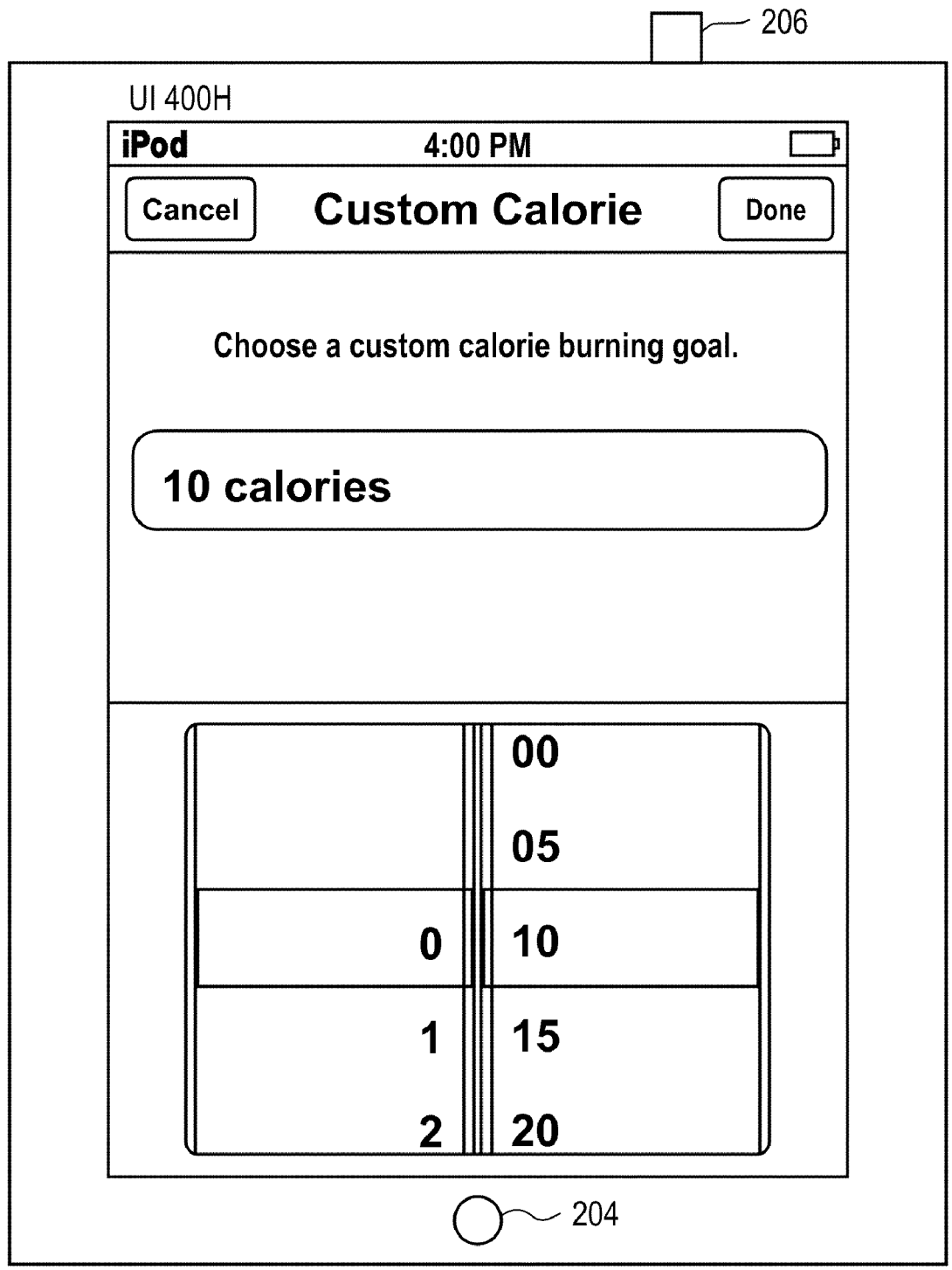
Figure 4I:
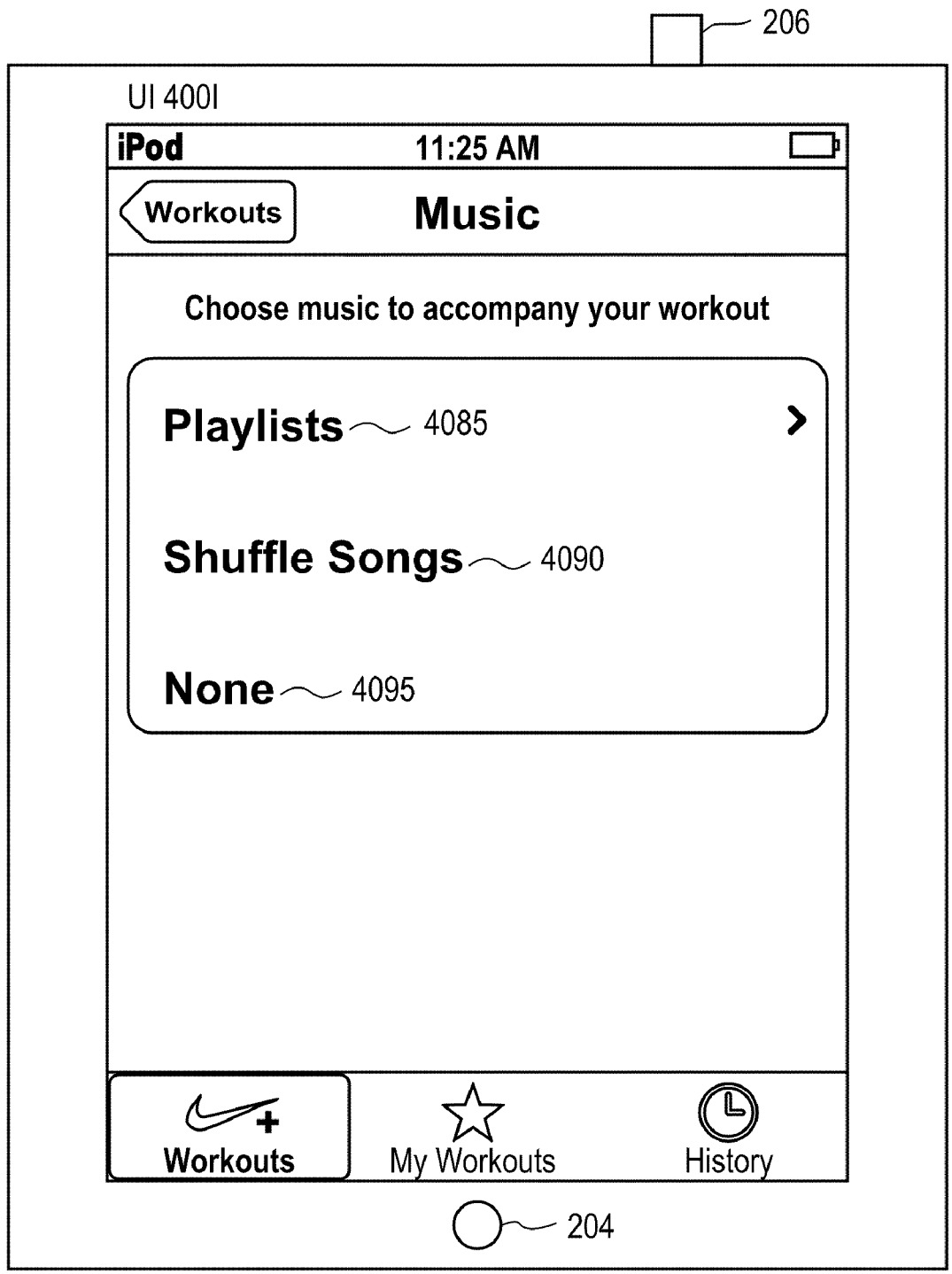

UI 400M (FIG. 4M), with the exemplary title "My Workouts," displays icons corresponding to workout profiles tailored to the user. In some embodiments, defined instances of workout types are saved as workout profiles on the portable electronic device 100. For example, as depicted in FIG. 4M, different workout profiles such as a 3 kilometer run, a 45 minute jog, or a 200 calorie burn workout can be saved. In FIG. 4M, the aforementioned workout profiles correspond, respectively, to first workout profile icon 4145-1, second workout profile icon 4145-2, and third workout profile icon 4145-3. In response to detecting a user-selection of a workout profile icon 4145, the workout support application 142 loads a workout profile corresponding to the selected workout profile icon.

UI 400N (FIG. 4N), with the exemplary title "History," displays icons 4165 corresponding to past workout data. In some embodiments, the workout support application 142 saves data from past workouts for later review. For example, as depicted in FIG. 4N, past workout sessions can be represented by historic workout icons 4165. In some embodiments, in response to selection of a historic workout icon 4165, the workout support application 142 will display further details about the corresponding past workout. UIs 400O-400Q (FIGS. 4O-4Q) depict exemplary summary information about past workouts. In some embodiments, a summary UI may depict which workout type the user had performed. For example, in UI 400O, workout type icon 4170 indicates that the workout type was a calorie workout.

UIs 400R-400T (FIGS. 4R-4T) support activation and linking of the sports device 304 with the portable electronic device 100. UI 400R (FIG. 4R) is an exemplary instructional screen to inform a user that it is necessary to walk around so that the sports device 304 will transmit data that the portable electronic device 100 can receive and process. In some embodiments, a cancel icon 4180 may be provided to cancel linking with the sports device 304. Once the sensor 304 is successfully activated and detected, the system may display a success message 4185 indicating it is linked to a sensor, as depicted in UI 400S (FIG. 4S). In some embodiments, a sensor identification code 4195 is depicted. As illustrated in UI 400T (FIG. 4T), in response to the workout support application 142 detecting an attempt to link to the same sensor it is already linked to, the system may present a warning message 4200 indicating which sensor the system is already linked to. Additionally, in some embodiments, a link new sensor icon 4205 may also be displayed in case the user wishes to link a different sensor 304 with the workout support application 142.

Figure 4J:
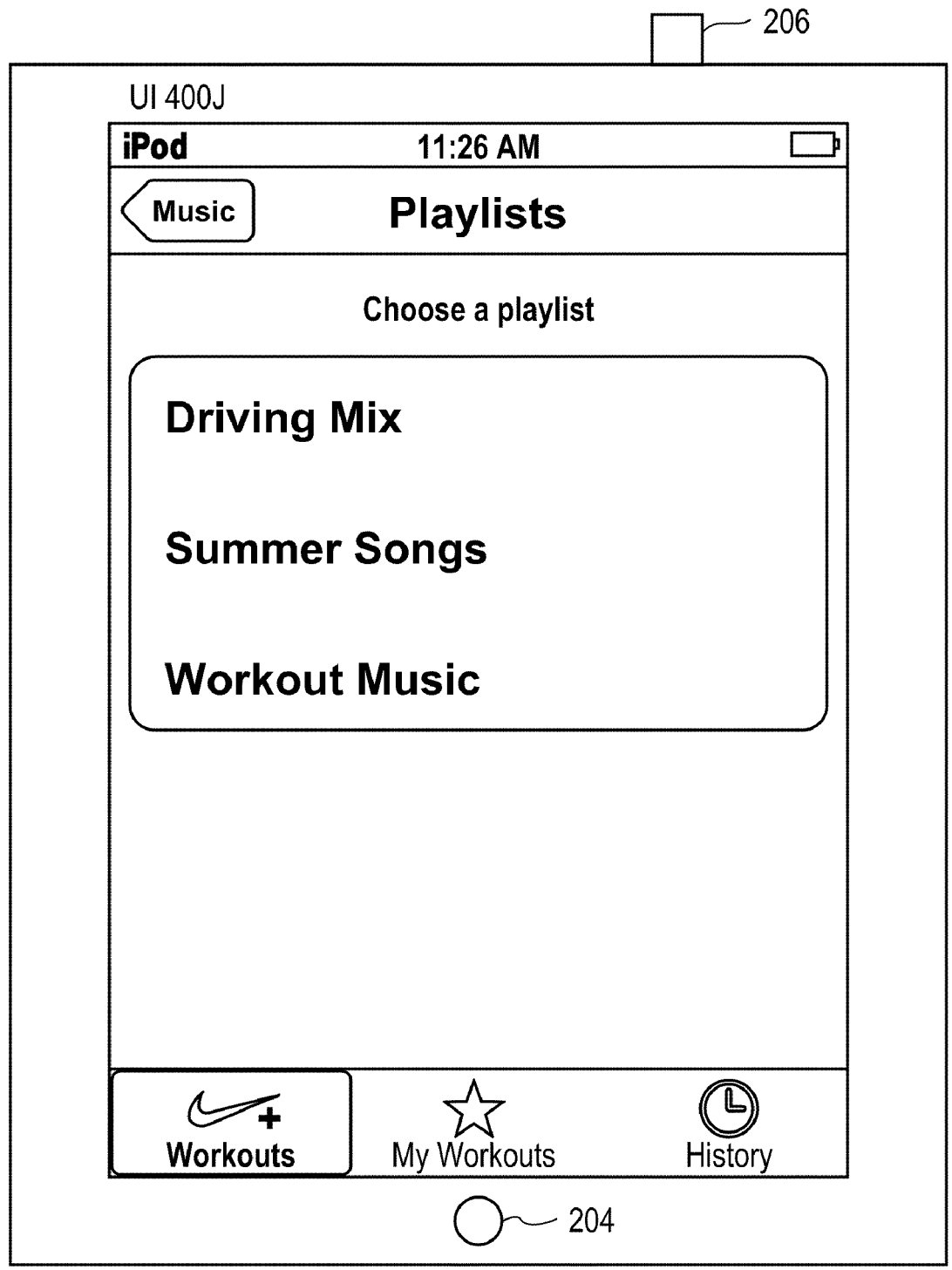
Figure 4K:
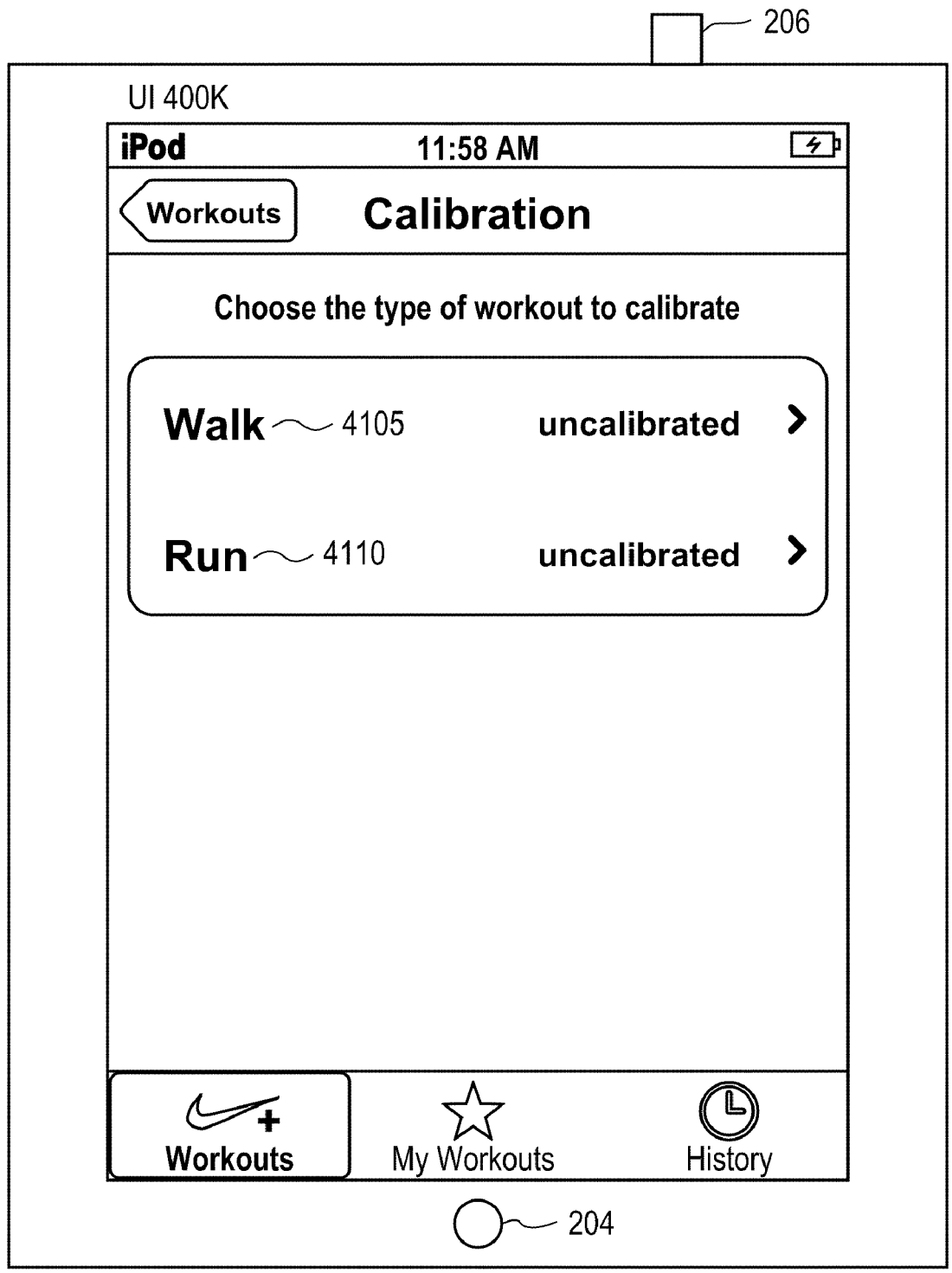
Figure 4L:
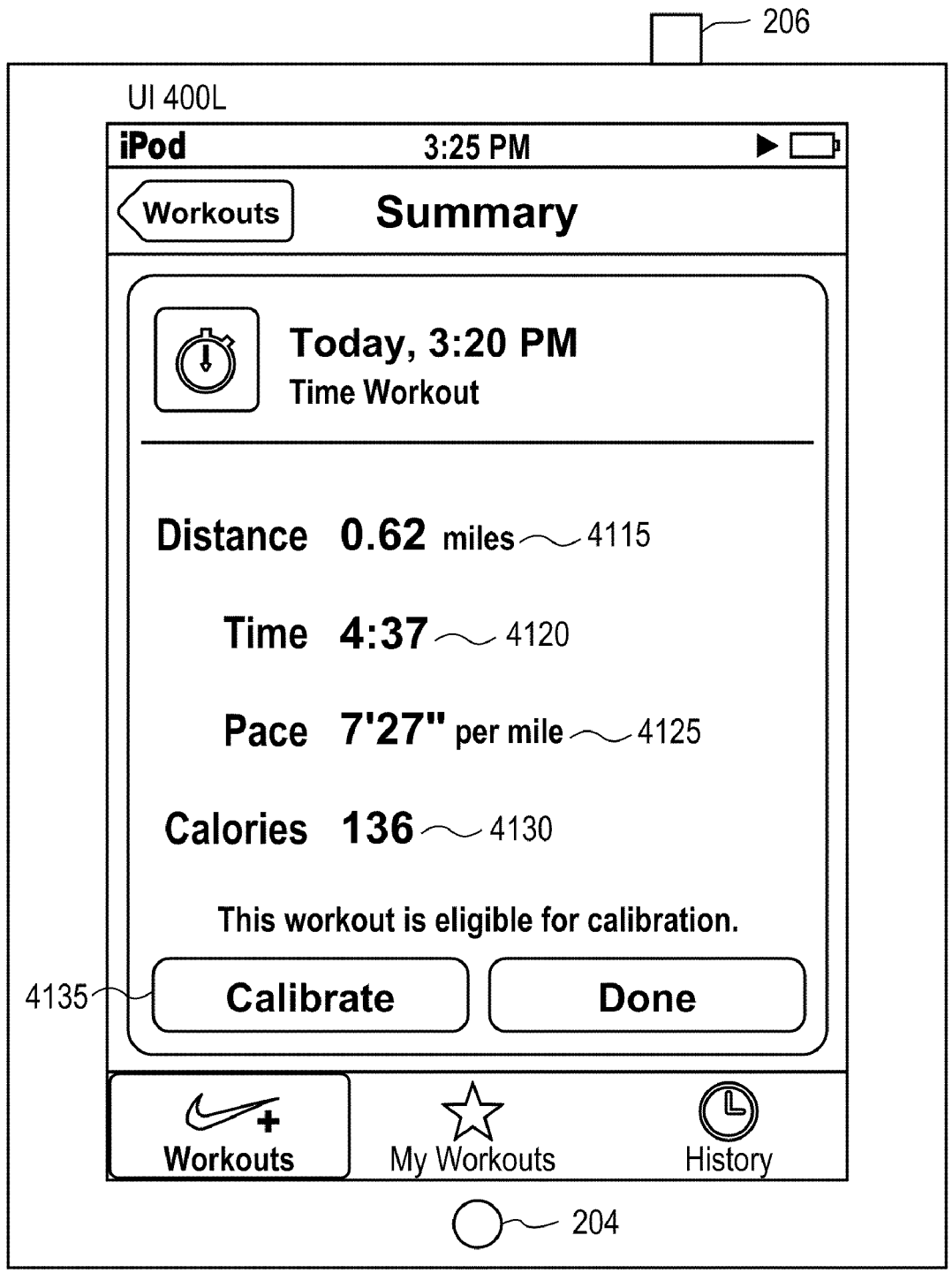
Figure 4M:
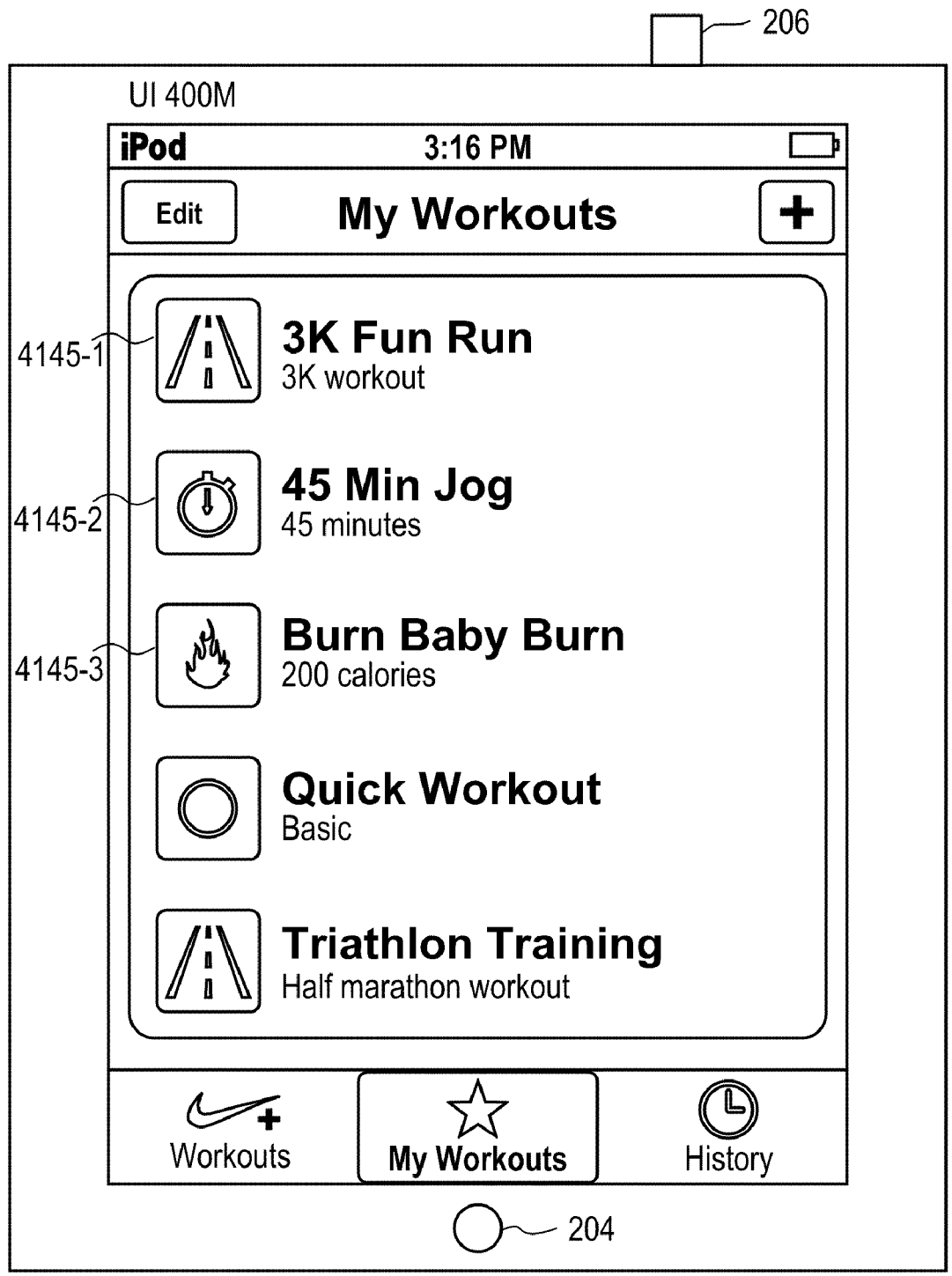
Figure 4N:
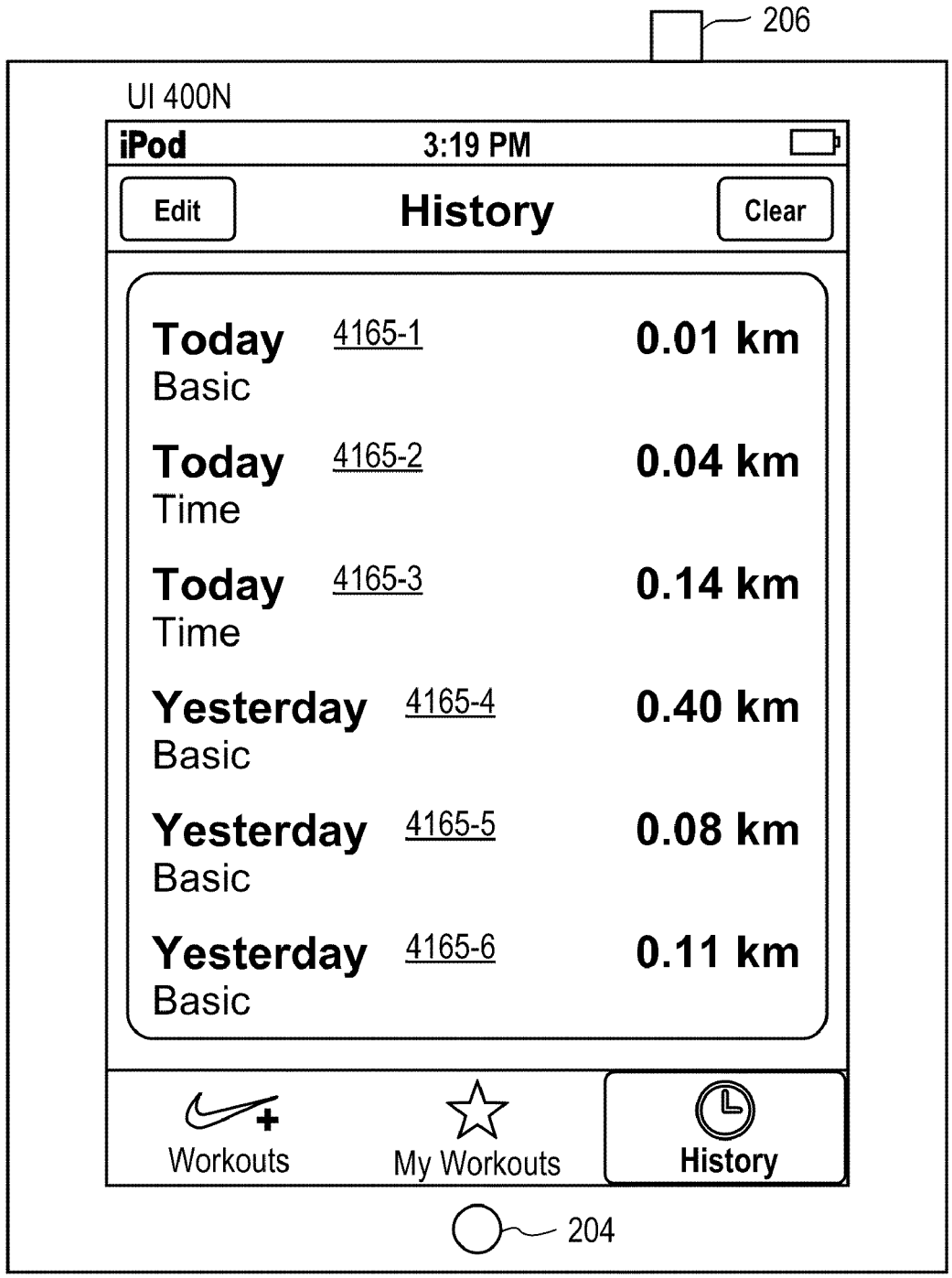
Figure 4O:
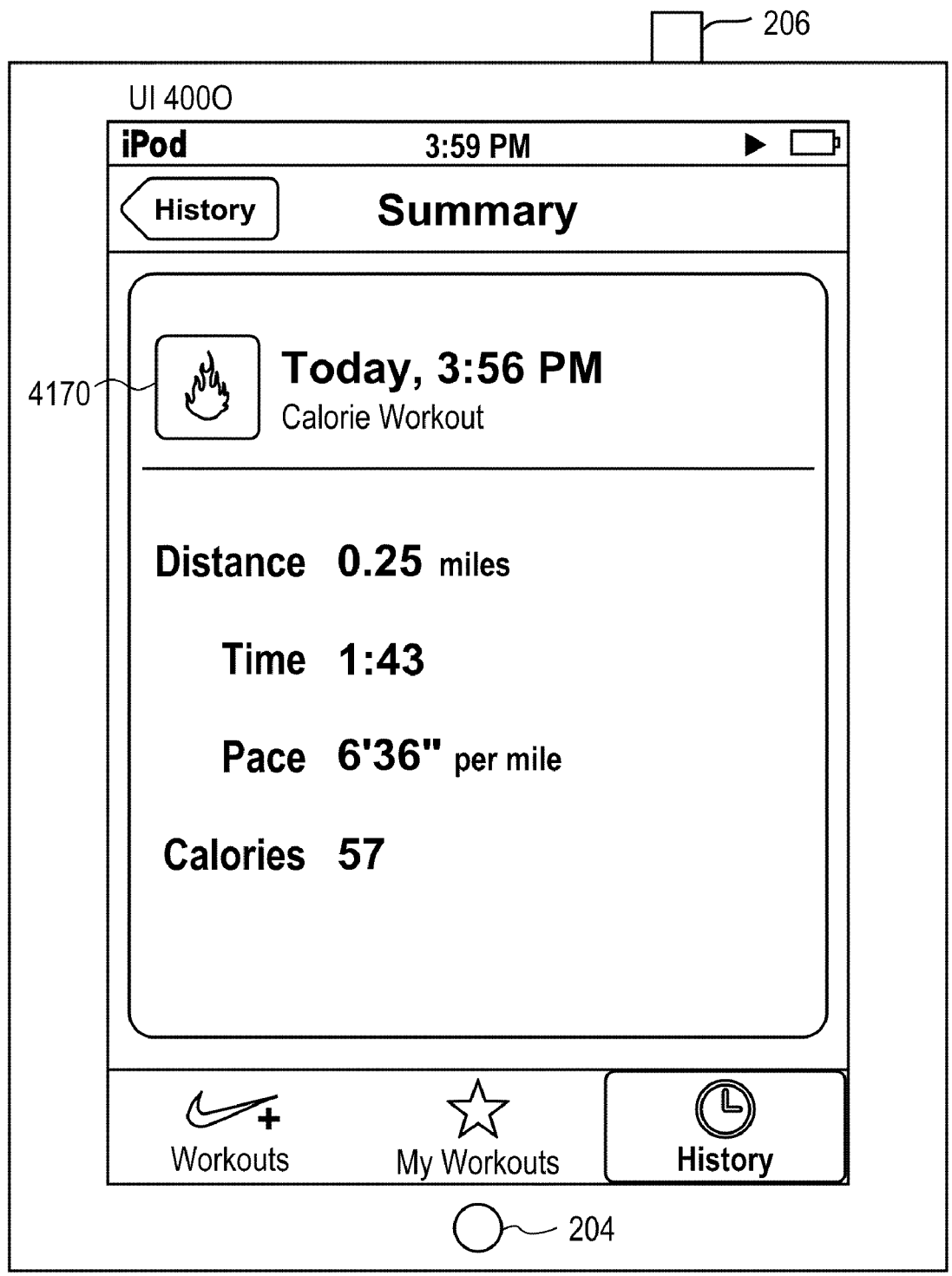
Figure 4P:
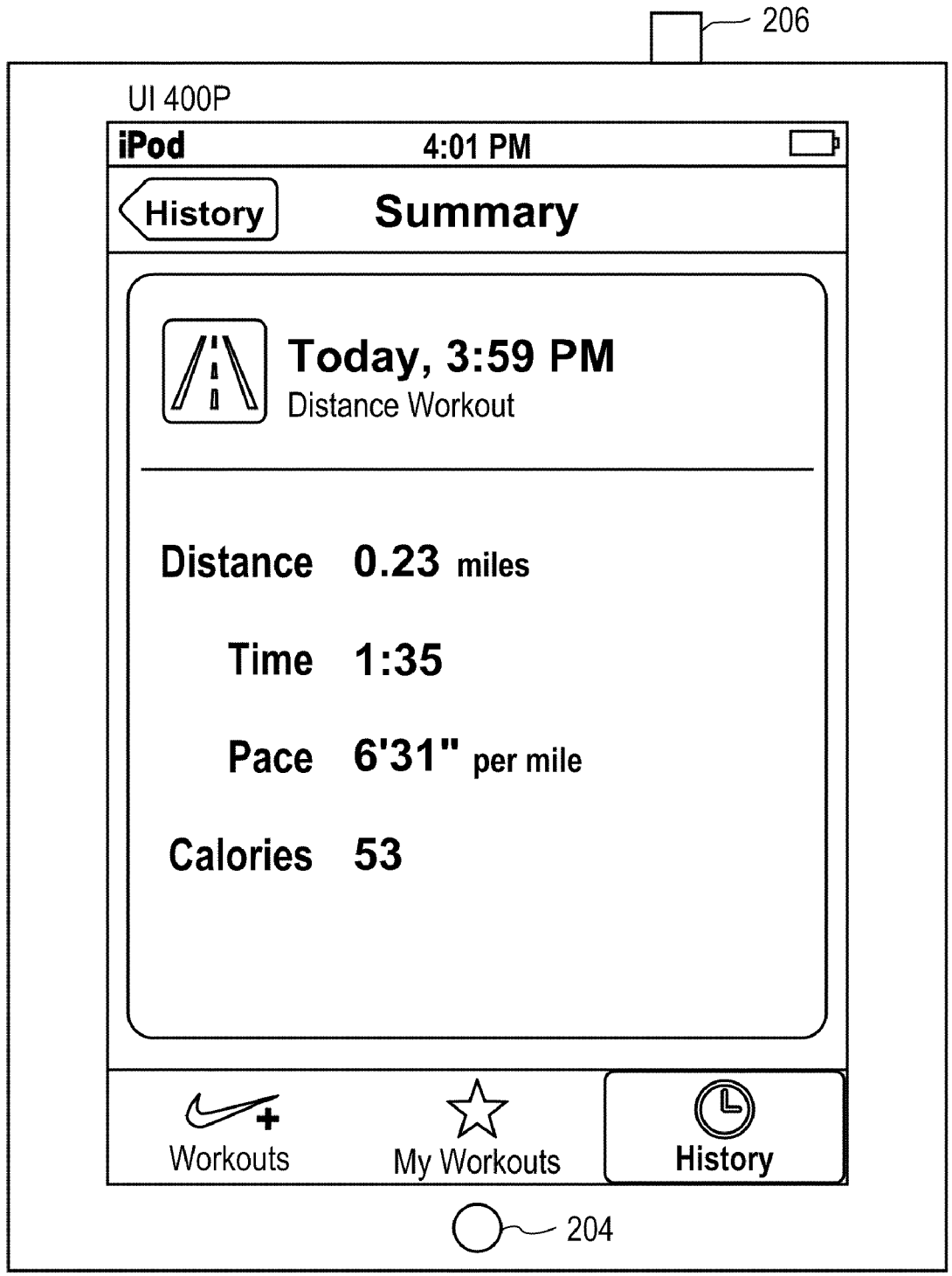
Figure 4Q:
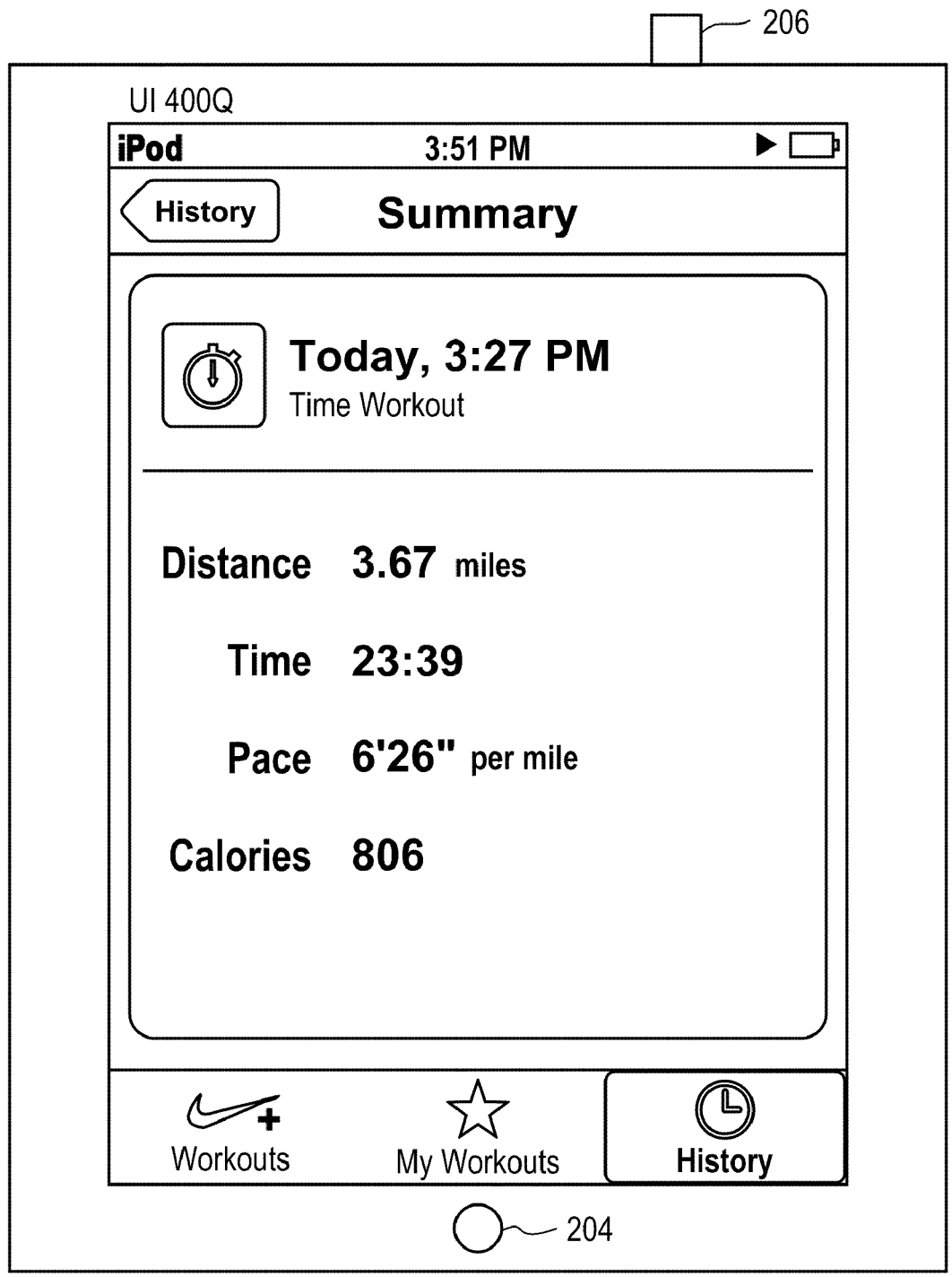
Figure 4R:
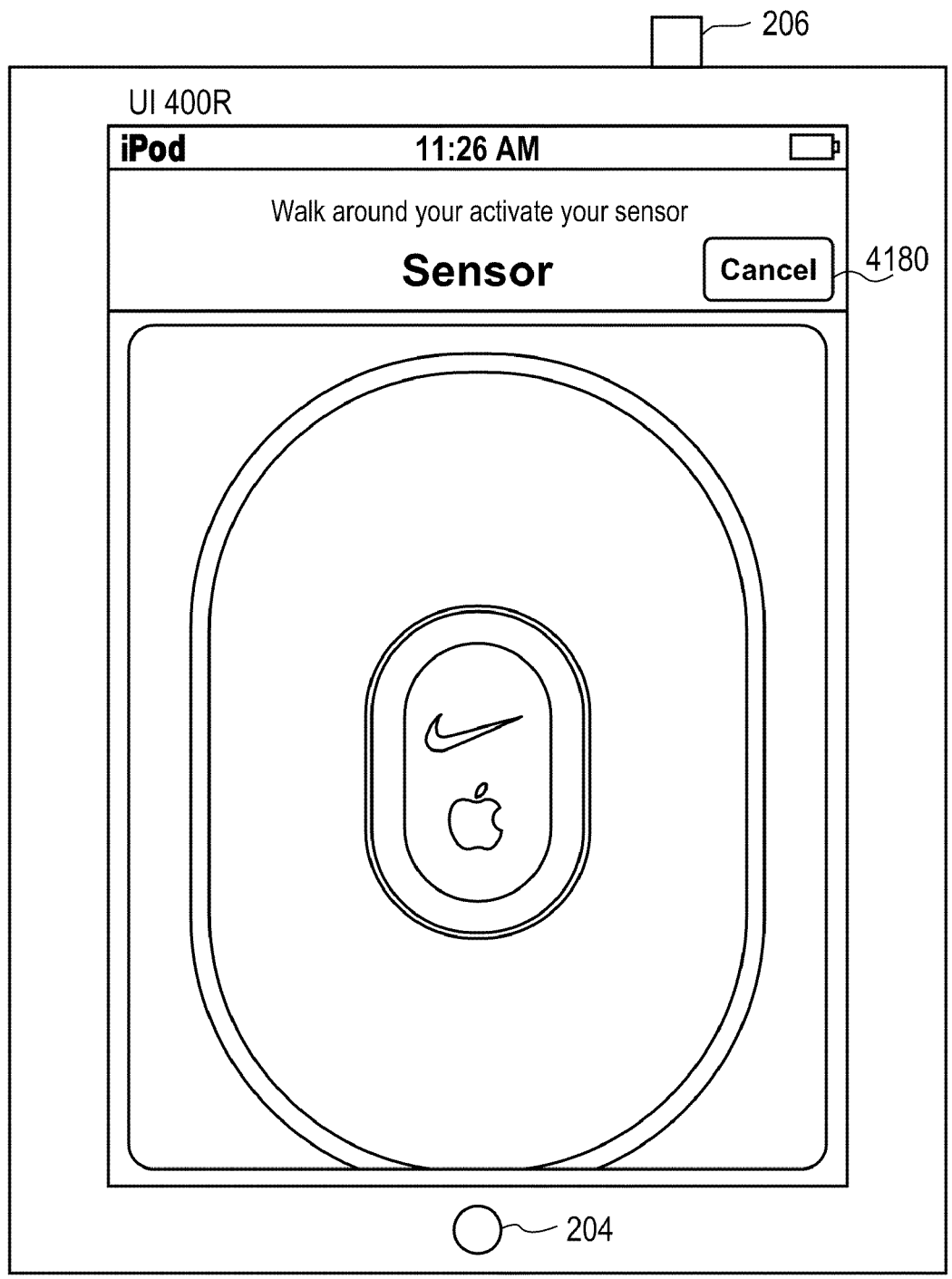
Figure 4S:
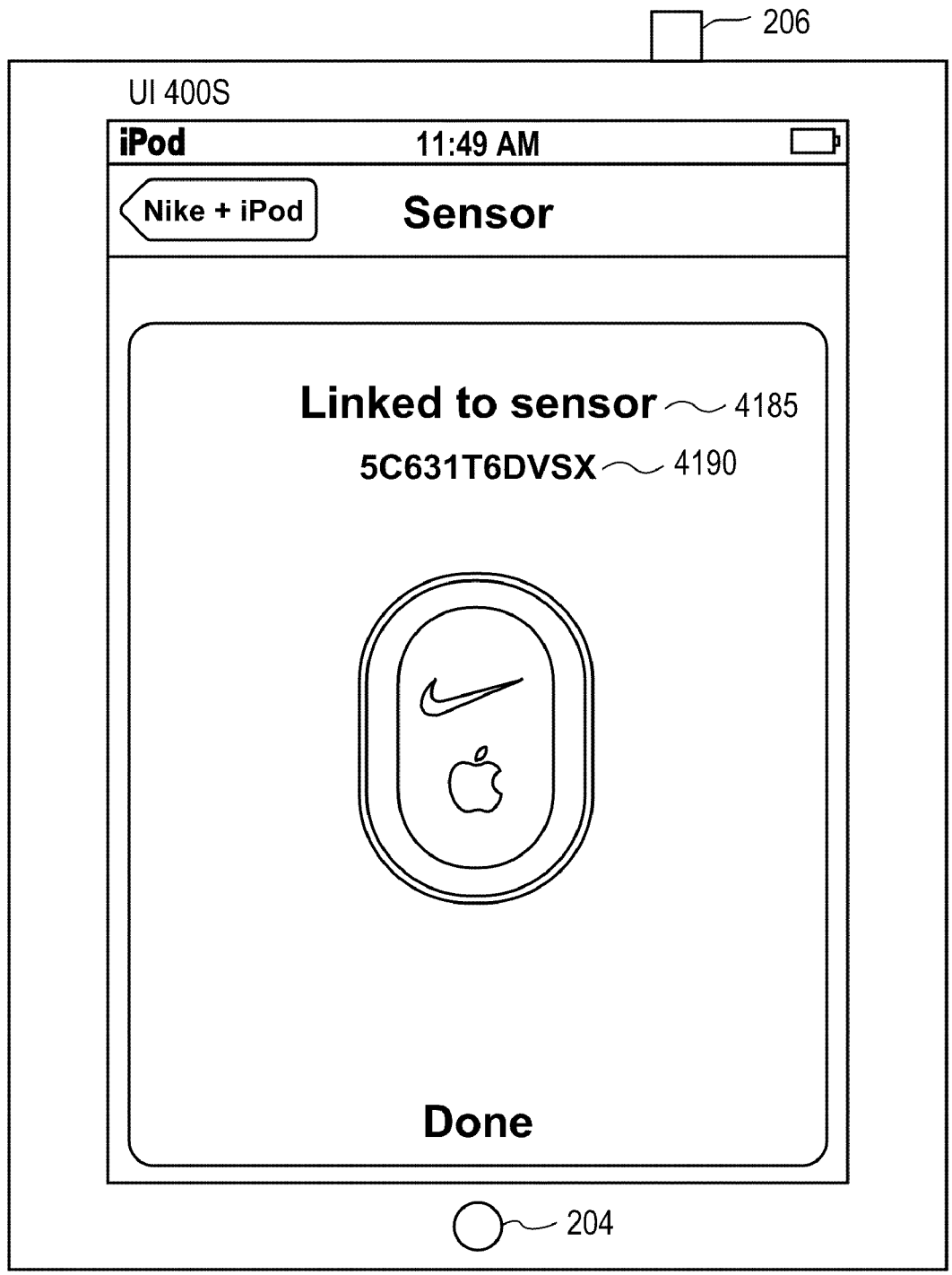
Figure 4T:
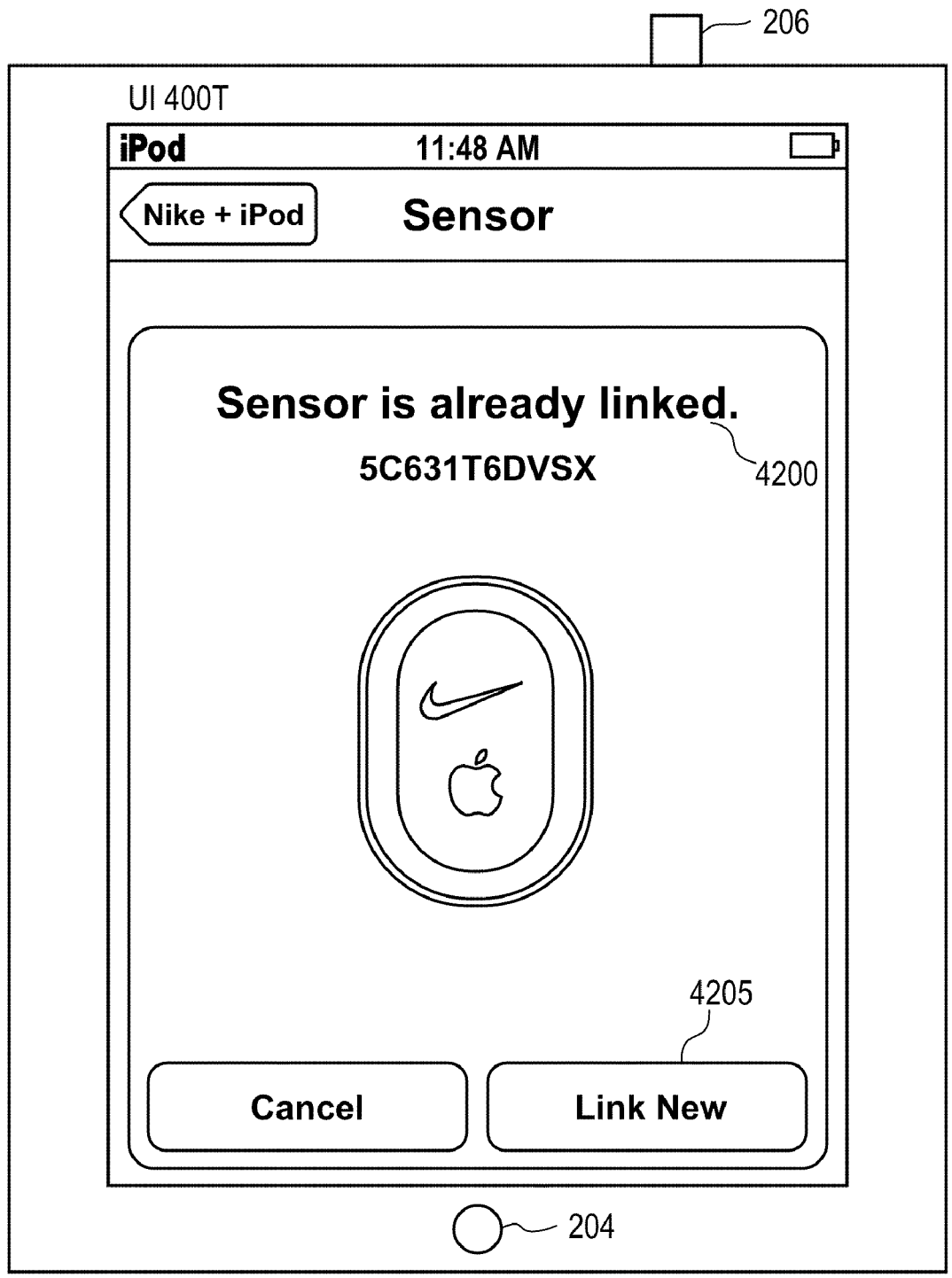

UIs 400U-400W (FIGS. 4U-4W) illustrate exemplary user interfaces when the workout support application 142 is in an unlocked mode monitoring a workout. These interfaces may display one or more of the following: an elapsed time indicator 4210, a distance traveled indicator 4215, and a numeric progress indicator 4220, which in this case, indicates 53 estimated calories burned. A pause-resume toggle icon 4225 is provided to allow the user to start or resume timing the workout. During the workout, this icon can be activated again to pause the workout. While the workout is paused, the time elapsed does not accrue, and no additional progress towards completing the workout is logged. An end workout icon 4230 may be provided to terminate the workout.

Additionally, some embodiments include a workout progress bar 4235. The workout progress bar 4235 graphically depicts how much of the goal set for the workout has been attained during a goal-based workout type, e.g., elapsed time, distance traveled, or estimated calories burned. For example, in UI 400U (FIG. 4U), the workout progress bar conveys that the user has homed approximately 50% of the calories towards completing the workout goal. The workout progress bar 4235 is not specific to workout type, but rather, can be displayed regardless of which type of goal-based workout type is being performed.

Further, in some embodiments, the workout support application 142 may be configured to present music playback controls 4240. For example, in FIG. 4U, previous icon 4240-2 and next icon 4240-1 are used to permit the user to go back to the previous track, or to advance to the next track, respectively. Additionally, a track title 4241 of the music currently being played is displayed in some embodiments.

UIs 400V and 400W (FIGS. 4V and 4W) are analogous to UI 400U (FIG. 4U), but present data related to distance and time workouts, respectively.

In some embodiments, such as that depicted in UI 400U (FIG. 4U), a powersong initiation icon 424 is provided. Referring now to UI 400X (FIG. 4X), in response to detecting activation of the powersong initiation icon 4245, the workout support application immediately changes the music being played to a specific track the user selected as her powersong, and the track title 4241 changes to display the user selected powersong title. In some embodiments, when the powersong initiation icon 4245 is activated, certain elements of the user interface may change. For example, an excitement indicator 4250 may be displayed when the powersong is activated. In this example, excitement indicator 4250 is a pulsating glow surrounding the workout progress bar 4235.

Figure 4U:
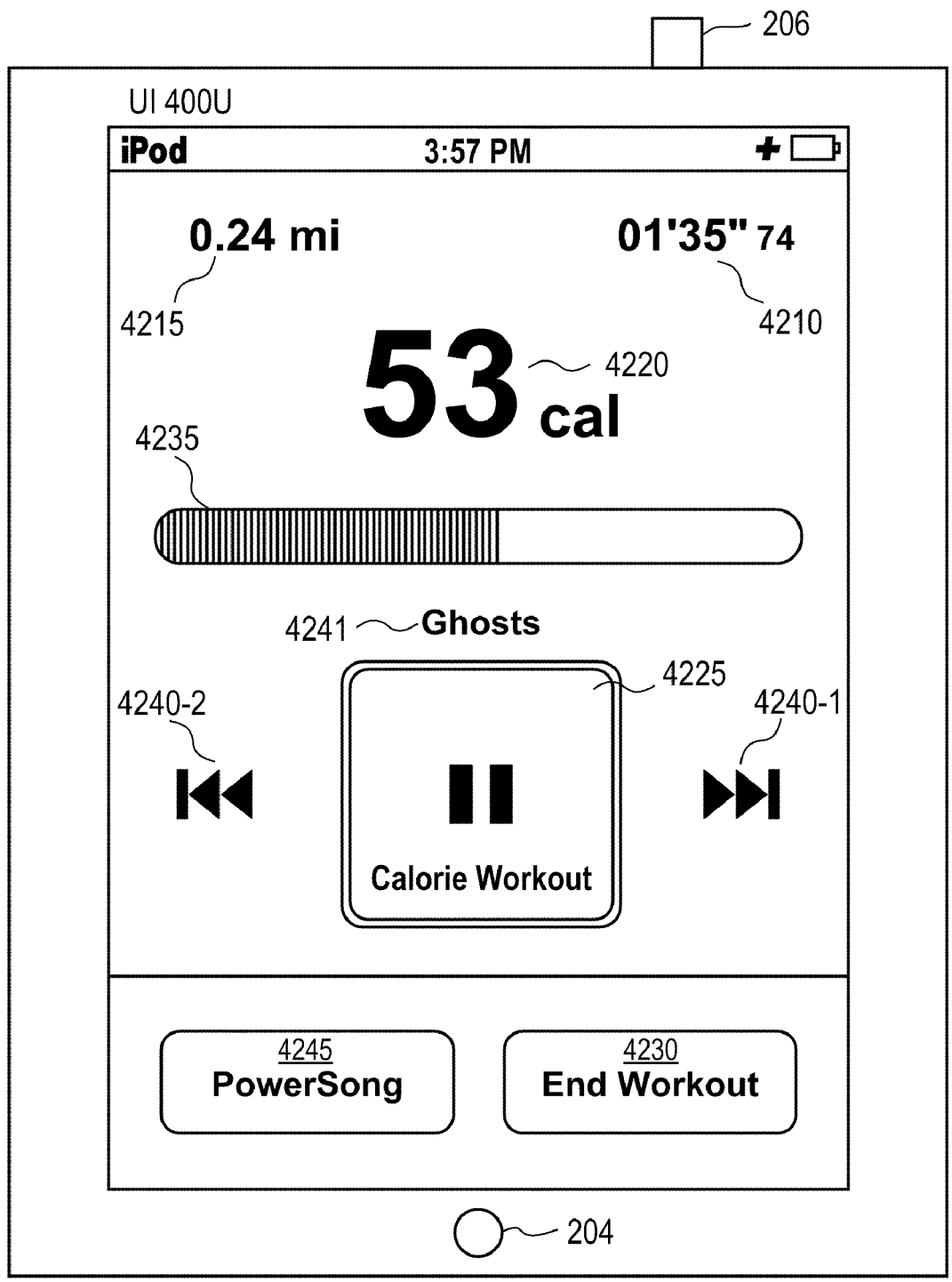
Figure 4V:
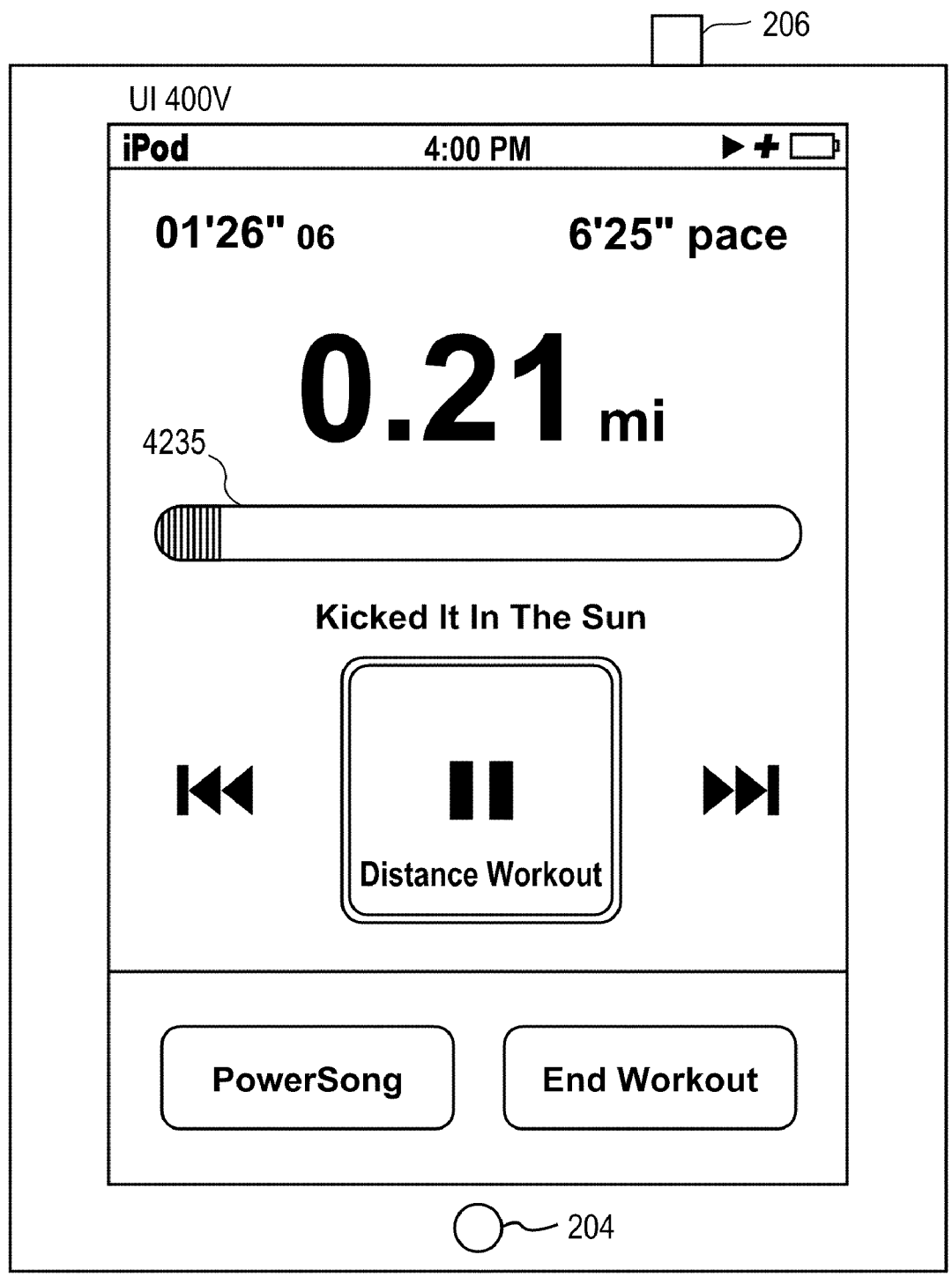

UI 400Y (FIG. 4Y) illustrates a modified application menu UI 400A (FIG. 4A) that is displayed in response to detecting activation of the menu icon or menu button 204 during display of a user interface for the workout monitoring application (e.g., UI 400U, FIG. 4U). In this example, the application menu UI is modified to include a return-to-workout-monitoring-application icon 4255, which, when activated here or when activated while displaying another application besides the workout monitoring application 142, will initiate redisplay of the workout support application 142.

UIs 400Z-400CC (FIGS. 4Z-4CC) are exemplary user interfaces that are displayed in a user-interface locked mode of the workout monitoring application. In comparison to the user-interface unlocked mode of the workout monitoring application, in the user-interface locked mode, only a restricted subset of workout control icons are displayed and the device 100 only responds to a restricted set of finger gestures. For example, just an enlarged toggle icon 4265 and as unlock image 4260 may be displayed (UI 400Z and 400AA) or just an enlarged powersong icon 4285, an enlarged previous track icon 4275, an enlarged next track icon 4280, and the unlock image 4260 may be displayed (UI 400BB and 400CC). In addition, as described below, a small number of gestures may be used to pause and resume the workout monitoring application and change the currently playing music. The use of the unlock image is described in more detail below.

The UIs in the user-interface locked mode typically have fewer, but larger control icons to allow a user to perform some operations on the device without looking at the control icons, i.e., unsighted operation. In some embodiments, the previous, next, pause/resume and/or powersong icons are larger in size when the workout support application is in the user-interface locked mode to make unsighted operation of the device easier. Moreover, in some embodiments, some of the enlarged control icons are placed in the corners of the touch screen to facilitate unsighted activation of these icons. For example, in UI 400BB (FIG. 4BB), the enlarged previous track icon 4275 and the enlarged next track icon 4280 are placed in the top-left corner and the top-right corner of the display, respectively, to make unsighted activation of these icons easier. Additionally, in some embodiments, finger gestures on the touch screen (e.g., swipe gestures) that are independent of the location of the gesture on the touch screen display are detected and used to control the device during a workout, which also permits unsighted operation.

UI 400Z (FIG. 4Z) illustrates that the workout support application 142 may be displayed in portrait orientation, while UI 400AA (FIG. 4AA) illustrates that the workout support application may be displayed in landscape orientation.

UI 400CC (FIG. 4CC) illustrates an exemplar version of the workout support application running in locked screen mode while a powersong is being played.

UI 400DD and 400EE (FIGS. 4DD and 4EE) illustrate that, in some embodiments, after the workout goal has been achieved, the application may display an indicator 4290 that the predetermined workout goal has been reached, such as a checkmark. In response to detecting further workout activity after the workout goal has been achieved, some embodiments may display a post-workout-goal activity bar 4295. In FIG. 4DD, the post-workout-goal activity bar 4295-1 is overlaid on the workout progress bar 4235. As shown in FIG. 4EE, the post-workout-goal activity bar 4295-2 may be configured to expand as further workout activity is detected.

UI 400FF (FIG. 4FF) illustrates a modified application UI that is displayed in response to detecting a finger gesture (e.g., a finger tap gesture) on an application icon in the menu of application icons other than an icon for the workout monitoring application (e.g., calendar icon 148). In this example, the application menu UI is modified to include a return-to-workout-monitoring-application icon 4255, which, when activated here or when activated while displaying another application besides the workout monitoring application 142, will initiate redisplay of the workout support application 142.

Some of the user interfaces in FIG. 4A-4FF are used to illustrate the processes described in FIGS. 5A-5J, 6A-6B, and 7-10 below.

FIGS. 5A-5J are flow diagrams illustrating a method of operating a workout support application 142 on a portable electronic device with a touch-sensitive display in accordance with some embodiments. The method 5000 is performed on a portable electronic device having a touch screen display (e.g., portable multifunction device 100). The method provides a simple and intuitive way for a user to control the workout support application 142 while exercising.

Operations 5002-5020 are performed while the portable electronic device 100 is in a user-interface locked mode of a workout monitoring application with the touch screen display turned off. Typically, other applications on the device are also locked when the device is in this mode. The device 100 will typically be in this mode when the user is exercising to reduce power and extend the battery life (e.g., by turning off the touch screen display).

The workout monitoring application 142 monitors (5002) a workout by a user. In some embodiments, monitoring the workout includes receiving (5004) data from a sensor that is separate from the portable electronic device, such as sports device 304.

In some embodiments, the device plays (5006) an audio file from a playlist with a plurality of audio files (e.g., an audio file from one of the playlists listed in UI 400J, FIG. 4J).

The device detects (5008) an interaction by a user with a first physical button (e.g., menu button 204, FIG. 2) on the portable electronic device.

The device determines (5010) whether the detected interaction by the user with the first physical button corresponds to a first predefined action. In some embodiments, the first predefined action is a single activation of the first physical button in a predefined time period (e.g., pressing the menu button 204 once in 0.3 seconds) (5012).

In response to determining mat the interaction by the user with the first physical button corresponds to the first predefined action, the device: turns on the touch screen display 112; displays a workout pause icon on the touch screen display (e.g., icon 4265, FIG. 4Z); and displays an unlock image on the touch screen display (e.g., unlock image 4260, FIG. 4Z) (5014). In some embodiments, in response to determining that the interaction by the user with the first physical button corresponds to the first predefined action, an audio status import of the workout by the user is provided (e.g., via speaker 111 or via headphones) (5015). In some embodiments, in response to determining that the interaction by the user with the first physical button corresponds to the first predefined action, workout information is also displayed, such as an elapsed time indicator 4210, a distance traveled indicator 4215, and/or a workout progress bar 4235 (FIG. 4Z).

As the name implies, a workout pause icon (e.g., icon 4265, FIG. 4Z) is an icon that when activated (e.g., by a finger tap on the icon) pauses the workout monitoring program.

The unlock image 4260 is a graphical user interface object with which the user interacts in order to change an application (e.g., workout monitoring application 142) to a user-interface unlocked mode. This interaction with the unlock image typically unlocks the rest of the device, too, so that other applications on the portable electronic device may also be used. Addition description of the use of an unlock image to unlock a device is described in U.S. patent application Ser. No. 11/322,549, "Unlocking a Device by Performing Gestures on an Unlock Image," filed Dec. 23, 2005, which is incorporated by reference herein in its entirety. U.S. patent application Ser. No. 11/322,549 focuses on using an unlock image to unlock a device with multiple applications. But analogous methods may used to change an application from a locked mode to an unlocked mode, independent of whether the rest of the device is also unlocked.

In some embodiments, the device determines (5016) whether the detected interaction by the user with the first physical button corresponds to a second predefined action, the second predefined action being different from the first predefined action. In some embodiments, the second predefined action is a double activation of the first physical button in a predefined time period (e.g., pressing the menu button 204 twice in succession in 0.3 seconds) (5018).

In response to determining that the interaction by the user with the first physical button corresponds to the second predefined action, the device: turns on the touch screen display 112; displays a powersong initiation icon on the touch screen display (e.g., icon 4285, FIG. 4BB); and displays the unlock image on the touch screen display (e.g., unlock image 4260, FIG. 4BB) (5020). In some embodiments, in response to determining that the interaction by the user with the first physical button corresponds to the second predefined action, an audio status report of the workout by the user is provided (e.g., via speaker 111 or via headphones) (5021). In some embodiments, in response to determining that the interaction by the user with the first physical button corresponds to the second predefined action, workout information is also displayed, such as an elapsed time indicator 4210, and/or a workout progress bar 4235 (FIG. 4BB).

As the name implies, a powersong initiation icon (e.g., icon 4260) is an icon that when activated (e.g., by a finger tap on the icon) initiates playing of an audio file previously selected by the user as the user's powersong.

In some embodiments, the device detects (5022) activation of the first physical button (e.g., menu button 204) while the audio status report is being provided. In response to detecting activation of the first physical button while the audio status report is being provided, the device ceases (5024) to provide the audio status report. Thus, the method may provide an audio status report by default, but it is easy to stop the audio status report if the user does not want to listen to the report.

In some embodiments, while the portable electronic device is in the user-interface locked mode of the workout monitoring application with the touch screen display turned off, the device detects (5026) activation of a second physical button (e.g., power on/off button 206, FIG. 2) on the portable electronic device. The second physical button is different from the first physical button. In response to detecting activation of a second physical button, the device: turns on the touch screen display 112 without providing an audio status report of the workout by the user; displays the workout pause icon on the touch screen display (e.g., icon 4265, FIG. 4Z); and displays the unlock image 4260 on the touch screen display (e.g., unlock image 4260, FIG. 4Z) (5028). Thus, by activating a second physical button, the user can keep the audio status report from playing at all.

In some embodiments, while the portable electronic device is in the user-interface locked mode of the workout monitoring application with the touch screen display turned on, the device detects (5030) a finger gesture on the workout pause icon 4265 (e.g., tap gesture 402, FIG. 4Z). In response to detecting the finger gesture on the workout pause icon, the device pauses (5032) monitoring of the workout by the workout monitoring application and pauses audio playback.

In some embodiments, while the portable electronic device is in the user-interface locked mode of the workout monitoring application with the touch screen display turned on, the device detects (5034) a finger gesture on the powersong initiation icon 4285 displayed on the touch screen display (e.g., tap gesture 404, FIG. 4BB). In response to detecting the finger gesture on the powersong initiation icon, the device initiates (5036) playing of an audio file previously selected by the user as the user's powersong.

In some embodiments, the portable electronic device performs operations 5038-5048 while the device is in the user-interface locked mode of the workout monitoring application with the touch screen display turned on. The device monitors (5038) the workout by the user with the workout monitoring application 142. The device plays (5040) an audio file from a playlist with a plurality of audio files. The device detects (5042) a finger swipe gesture on the touch screen display. The device determines (5044) whether the detected finger swipe gesture is in a first predefined direction or a second predefined direction on the touch semen display, the second predefined direction being opposite the first predefined direction. For example, the device determines whether the swipe gesture is from right to left on the touch screen display (e.g., gesture 406, FIG. 4Z) or from left to right on the touch screen display (e.g., gesture 408, FIG. 4Z). As another example, the device determines whether the swipe gesture is vertically downward on the touch screen display (e.g., gesture 410, FIG. 4Z) or vertically upward on the touch screen display (e.g., gesture 412, FIG. 4Z). In some embodiments, the direction determination is independent of the location of the swipe gesture on the touch screen display. In response to determining that the finger swipe gesture is in the first predefined direction, the device terminates play of the audio file and initiates play of a next audio file from the playlist (5046). In response to determining that the finger swipe gesture is in the second predefined direction, the device terminates play of the audio file and initiates play of a previous audio file from the playlist (5048).

In some embodiments, the portable electronic device performs operations 5050-5056 while the portable electronic device is in the user-interface locked mode of the workout monitoring application with the touch screen display turned on. The device monitors (5050) the workout by the user with the workout monitoring application 142. The device plays (5052) an audio file from a playlist with a plurality of audio files. The device detects (5054) a finger swipe gesture on the touch screen display. In response to detecting the finger swipe gesture, the device: terminates play of the audio file and initiates play of a next audio file from the playlist if the detected finger gesture is in a first horizontal or substantially horizontal direction (e.g., swipe gesture 406, FIG. 4Z, moving from right to left across the touch screen display within a predetermined angle of the horizontal axis of the touch screen display) across the touch screen display; terminates play of the audio file and initiates play of the next audio file from the playlist if the detected finger gesture is in a first vertical or substantially vertical direction (e.g., swipe gesture 410, FIG. 4Z, moving from top to bottom across the touch screen display within a predetermined angle of the vertical axis of the touch screen display) across the touch screen display; terminates play of the audio file and initiates play of a previous audio file from the playlist if the detected finger gesture is in a second horizontal or substantially horizontal direction (e.g., swipe gesture 408, FIG. 4Z, moving from left to right across the touch screen display within a predetermined angle of the horizontal axis of the touch screen display) across the touch screen display, the second horizontal direction being opposite the first horizontal direction; and terminates play of the audio file and initiates play of the previous audio file from the playlist if the detected finger gesture is in a second vertical or substantially vertical direction (e.g., swipe gesture 412, FIG. 4Z, moving from bottom to top across the touch screen display within a predetermined angle of the vertical axis of the touch screen display) across the touch screen display, the second vertical direction being opposite the first vertical direction (5056).

Thus, the user can use simple finger swipe gestures (e.g., gestures 406, 408, 410, and/or 412, FIG. 4Z) while exercising to play a next track or a previous track while the workout support application and the device remain locked, without needing to see the touch screen display or make precise contacts with the display.

In some embodiments, the portable electronic device contains one or more accelerometers 168 (FIG. 1).

In some embodiments, the device detects (5058) with the one or more accelerometers 168 a first movement of the portable electronic device. The device determines (5060) whether the first movement is due to a first predetermined type of user gesture exerted on the portable electronic device (e.g., a single smack (slap) exerted or the portable electronic device within a predefined time window or a predefined number of smacks (e.g., two) exerted on the portable electronic device within a predefined time window). The device initiates (5062) play of a powersong audio file of the user if the movement is due to the first predetermined type of user gesture. Thus, in some embodiments, the user can use smacks while exercising to play a powersong, without needing to see the touch screen display or make precise contacts with the display.

In some embodiments, the device detects (5064) with the one or more accelerometers 168 a second movement of the portable electronic device. The device determines (5066) whether the movement is due to a second predetermined type of user gesture exerted on the portable electronic device (e.g., a predefined number of smacks (e.g., two) exerted on the portable electronic device within a predefined time window or a single smack exerted on the portable electronic device within a predefined time window). The device toggles (5068) between monitoring the workout and pausing monitoring of the workout if the movement is due to the second predetermined type of user gesture. Thus, in some embodiments, the user can use smacks while exercising to pause and resume the workout, without needing to see the touch screen display or make precise contacts with the display.

In some embodiments, the portable electronic device performs operations 5070-5076 while the device is in the user-interface locked mode of the workout monitoring application with the touch screen display turned on. The device detects (5070) a finger contact with the unlock image 4260 and subsequent movement of the finger contact on the touch screen display (e.g., finger contact 414, FIG. 4Z). The device moves (5072) the unlock image on the touch screen display in accordance with the detected movement of the finger contact. The device transitions (5074) the workout monitoring application to a user-interface unlocked mode and displays a user interface in the workout monitoring application (e.g., UI 400W, FIG. 4W) if the detected movement of the finger contact corresponds to a predefined gesture. The device and other applications therein may also transition to respective user-interface unlock states if the detected movement of the finger contact corresponds to the predefined gesture. The device maintains (5076) the device in the user-interface locked mode of the workout monitoring application if the detected movement of the finger contact does not correspond to the predefined gesture.

In some embodiments, the portable electronic device performs operations 5078-5092 while the portable electronic device is in a user-interface unlock state and while monitoring the workout by the user with the workout monitoring application. The device displays (5078) on the touch screen display a user interface for the workout monitoring application (e.g., UI 400W, FIG. 4W). The device detects (5080) activation of a menu icon or menu button (e.g., home button 204, FIG. 4W) during display of the user interface for the workout monitoring application. In response to detecting activation of the menu icon or menu button during display of the user interface for the workout monitoring application, the device replaces (5082) the user interface for the workout monitoring application with a menu of application icons (e.g., UI 400Y, FIG. 4Y). The device maintains (5084) monitoring of the workout by the user while displaying the menu of application icons on the touch screen display. The device detects (5086) a finger gesture on an application icon in the menu of application icons other than an icon for the workout monitoring application (e.g., tap gesture 416 on calendar icon 148, FIG. 4Y). In response to detecting a finger gesture on the application icon in the menu of application icons other than the icon for the workout monitoring application, the device displays (5088) a user interface for a corresponding application on the touch screen display while continuing to maintain monitoring of the workout by the user (e.g., calendar UI 400FF, FIG. 4FF). The user interface for the corresponding application includes a return-to-workout-monitoring-application icon (e.g., icon 4255, FIG. 4FF) that is not displayed in the user interface for the corresponding application when there is no ongoing monitoring of the workout by the user. The device detects (5090) a finger gesture on the return-to-workout-monitoring-application icon (e.g., tap gesture 416, FIG. 4FF). In response to detecting the finger gesture 416 on the return-to-workout-monitoring-application icon, the device replaces (5092) display of the user interface for the corresponding application (e.g., calendar UI 400FF, FIG. 4FF) with a respective user interface for the workout monitoring application (e.g., UI 400W, FIG. 4W) while continuing to monitor the workout by the user.

In some embodiments, the portable electronic device transitions (5094) to a user-interface locked mode of the workout monitoring application upon expiration of a predetermined time period without detecting user input to the device. In some embodiments, the transition to the user-interface locked mode also includes turning off the touch screen display to save power.

In accordance with some embodiments, a graphical user interface on a portable electronic device 100 with a touch screen display 112 includes a workout pause icon 4265 on the touch screen display and an unlock image 4260 on the touch screen display (e.g., UI 400Z, FIG. 4Z). The unlock image 4260 is a graphical user interface object with which the user interacts in order to change a workout monitoring application 142 to a user-interface unlocked mode. While the portable electronic device is in a user-interface locked mode of a workout monitoring application with the touch screen display turned off: a workout by a user is monitored with the workout monitoring application 142; an interaction by the user with a first physical button (e.g., menu button 204, FIG. 4Z) on the portable electronic device is detected; and whether the detected interaction by the user with the first physical button corresponds to a first predefined action is determined. In response to determining that the interaction by the user with the first physical button corresponds to the first predefined action: the touch screen display 112 is turned on; the workout pause icon 4265 is displayed on the touch screen display; and the unlock image 4260 is displayed on the touch screen display. In some embodiments, in response to determining that the interaction by the user with the first physical button corresponds to the first predefined action, workout information is also displayed, such as an elapsed time indicator 4210, a distance traveled indicator 4215, and/or a workout progress bar 4235 (FIG. 4Z).

Figure 6B:
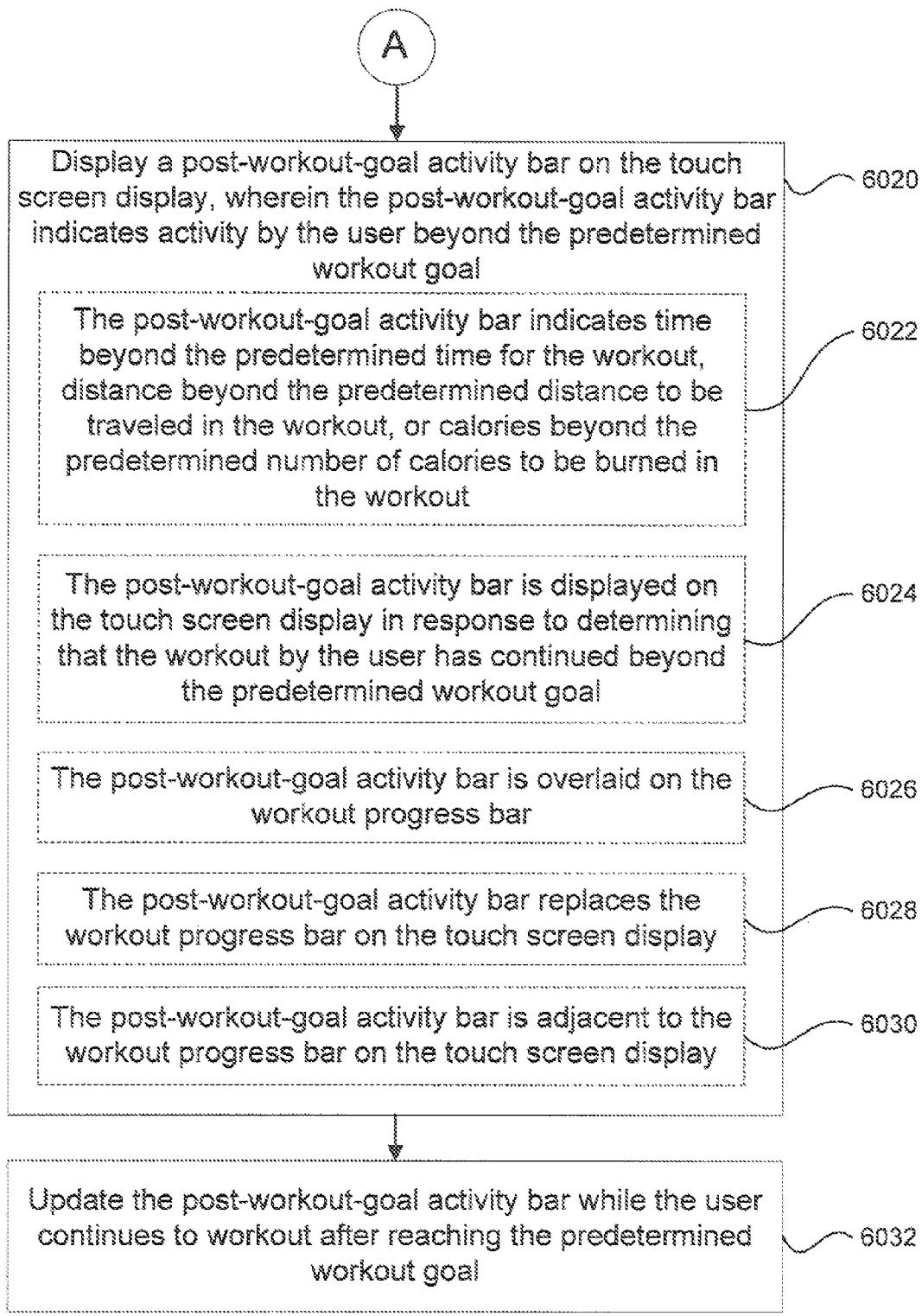

FIGS. 6A-6B are flow diagrams illustrating a method of monitoring and displaying post-workout-goal activity in accordance with some embodiments. The method 6000 is performed on a portable electronic device having a touch screen display (e.g., portable multifunction device 100). The method provides a simple and intuitive way for a user to see progress beyond a specified workout goal.

The device monitors (6002) a workout by a user with a workout monitoring application 142. The workout has a predetermined workout goal for the user. In some embodiments, the predetermined workout goal for the user is a predetermined time for the workout, a predetermined distance to be traveled in the workout, or a predetermined number of calories to be burned in the workout (6004).

Figure 4W:
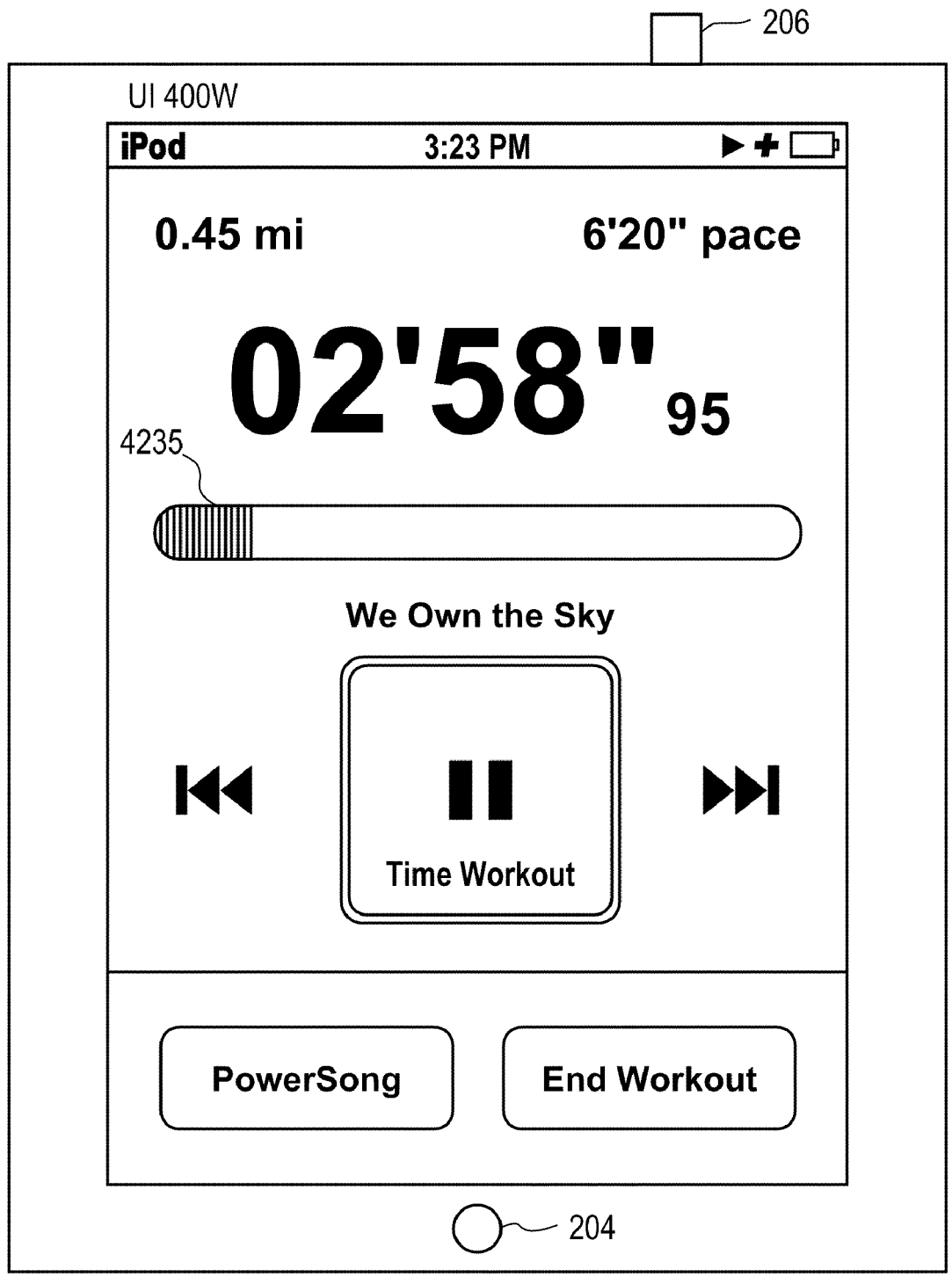
Figure 4X:
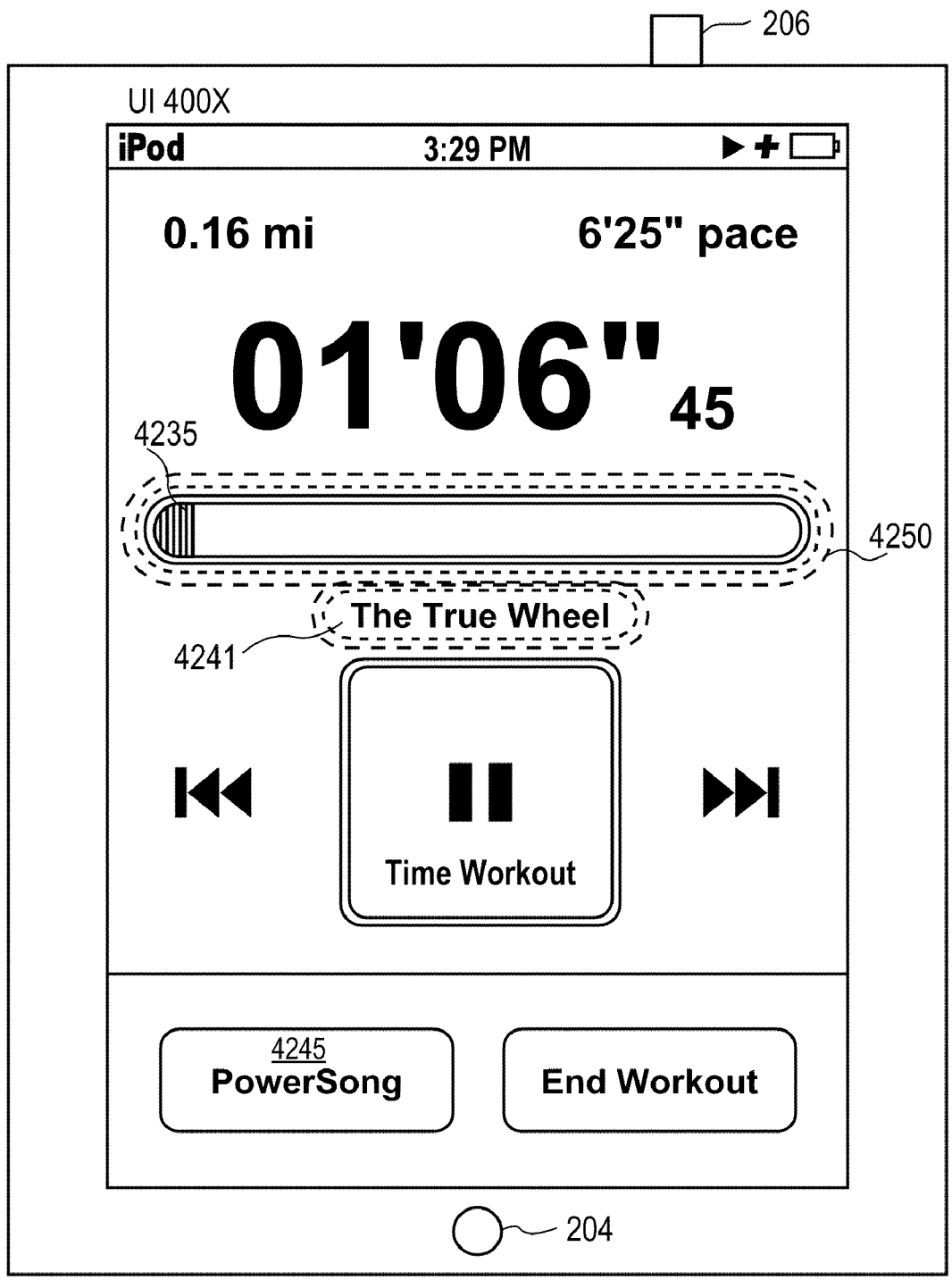
Figure 4Y:
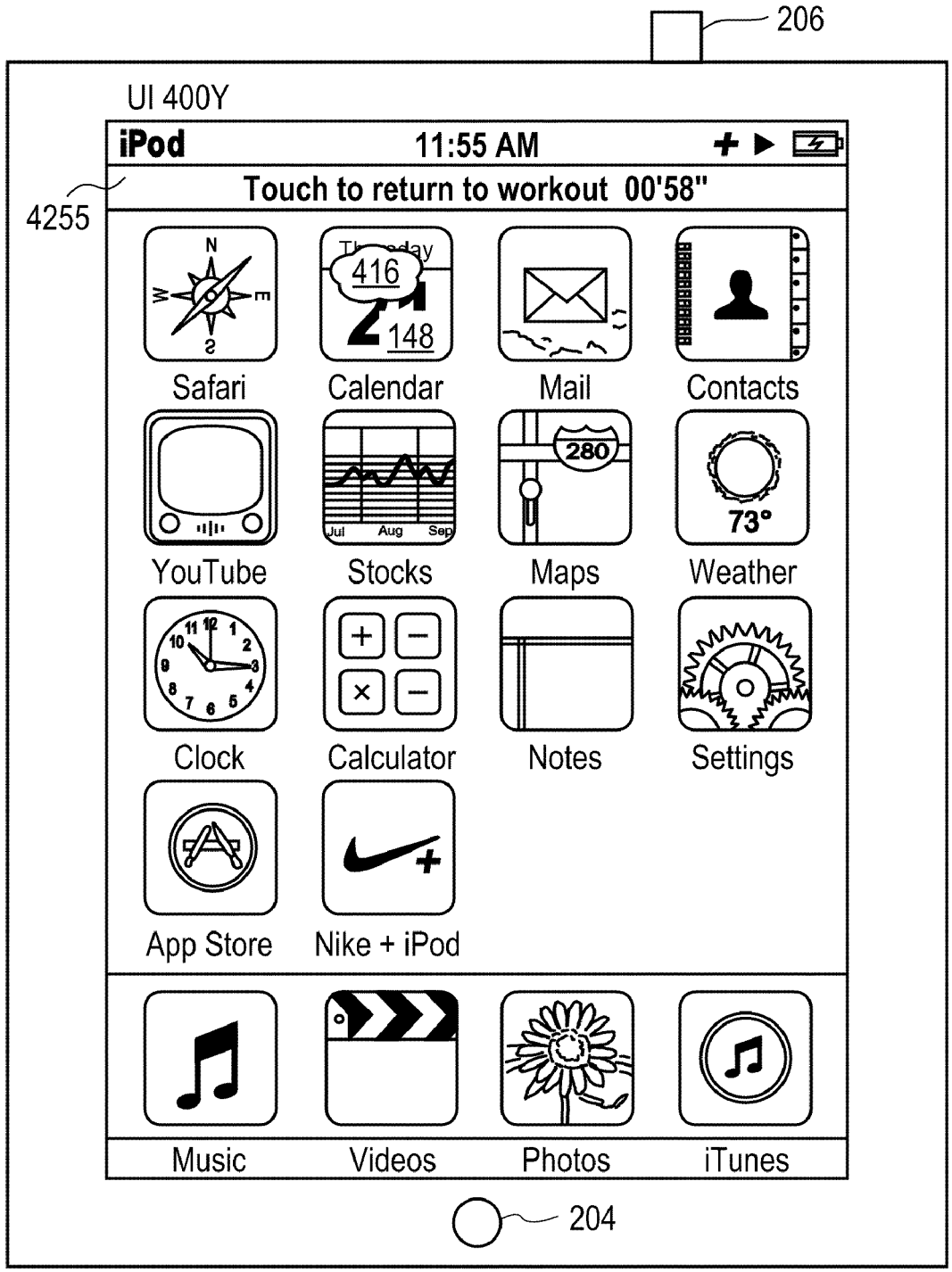
Figure 4Z:
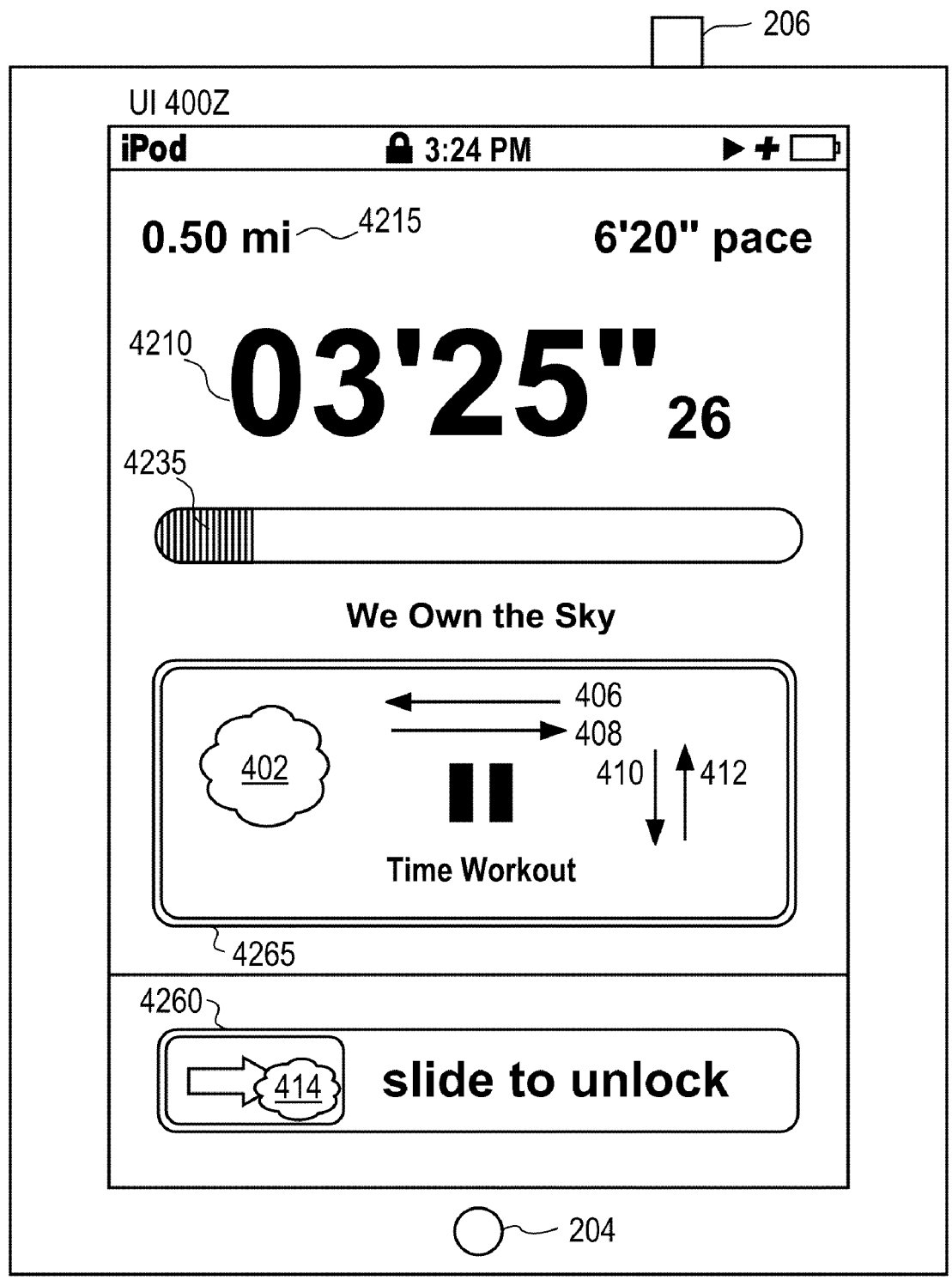
Figure 4A:
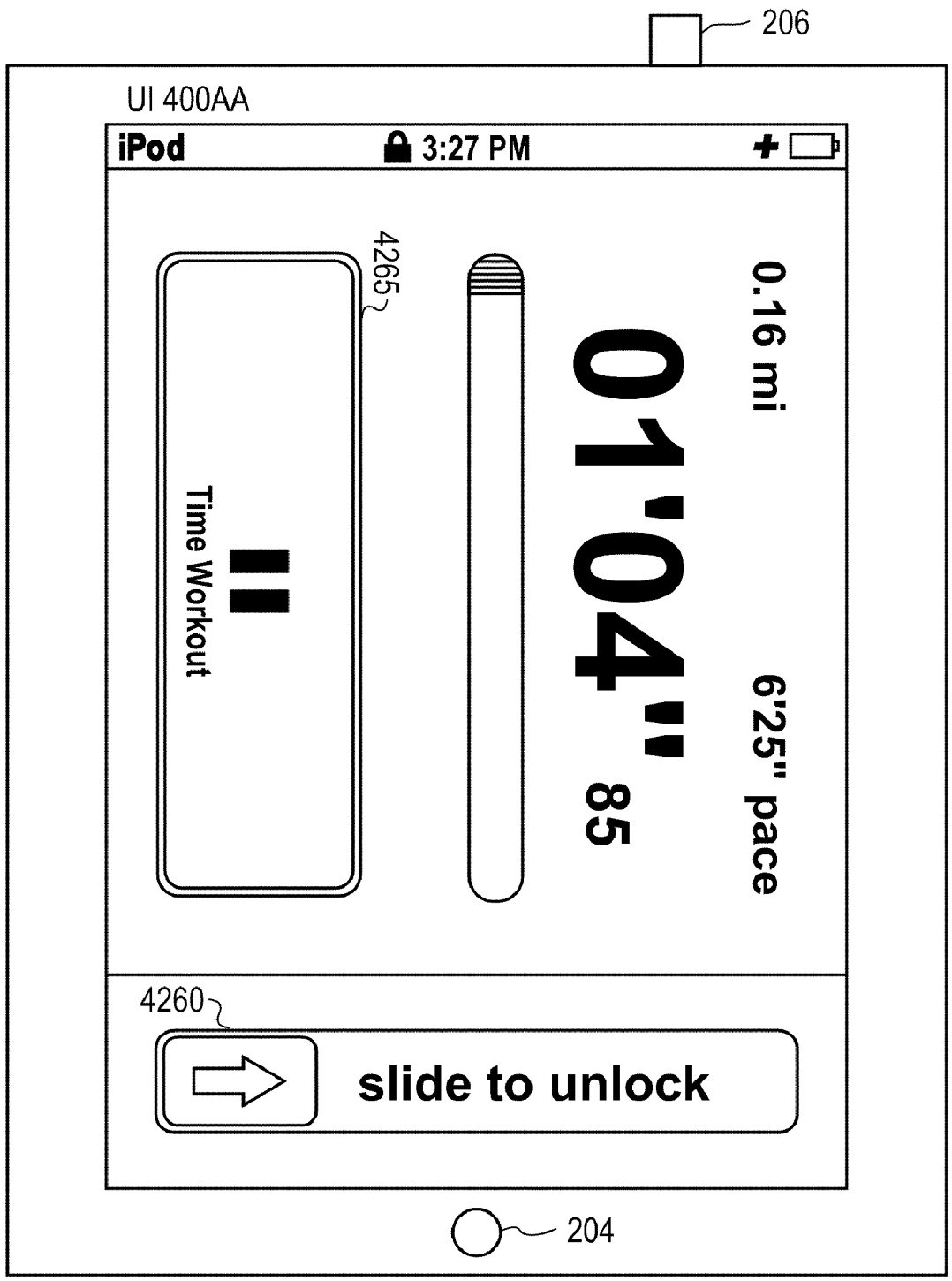
Figure 4B:
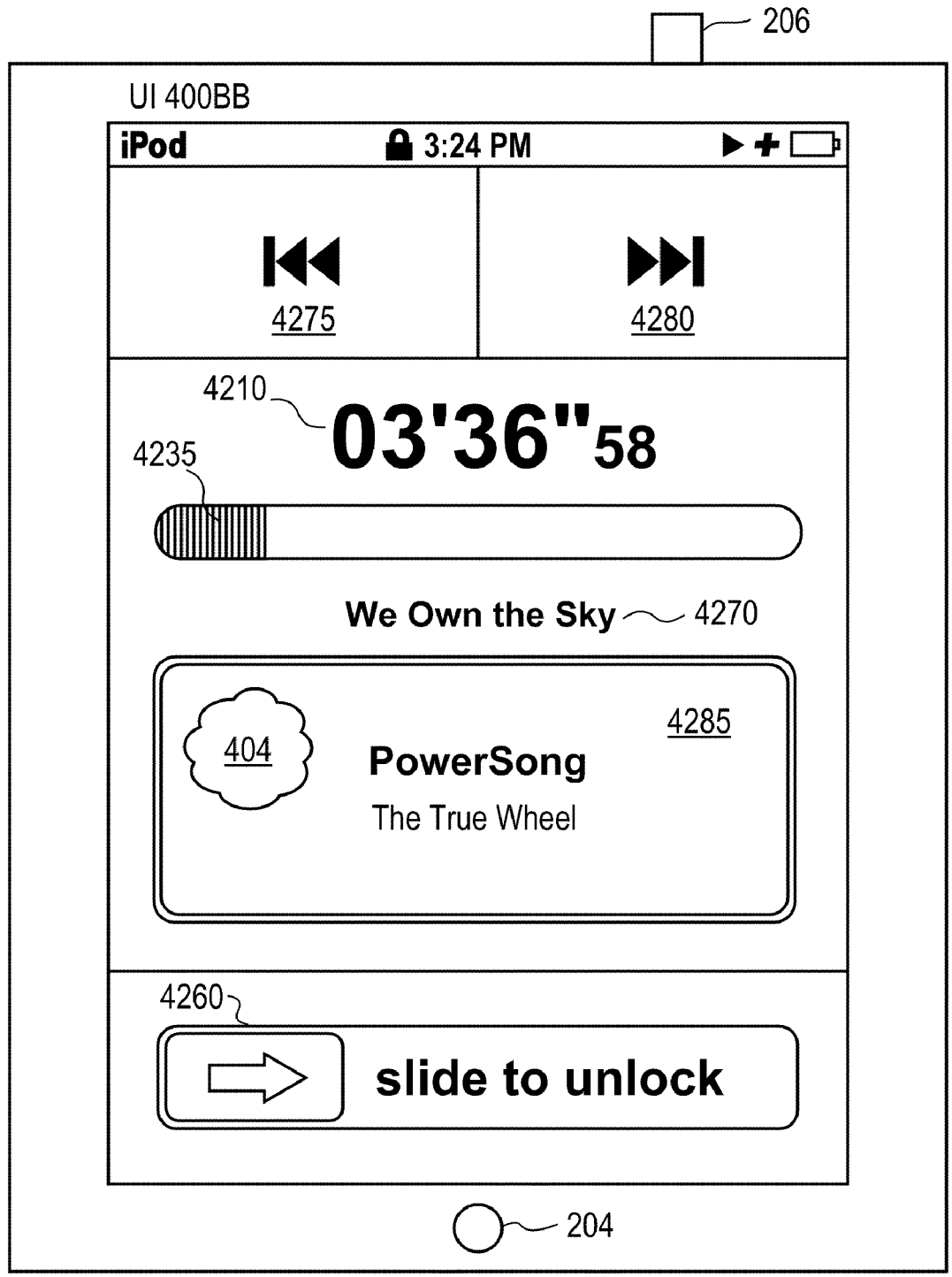
Figure 4C:
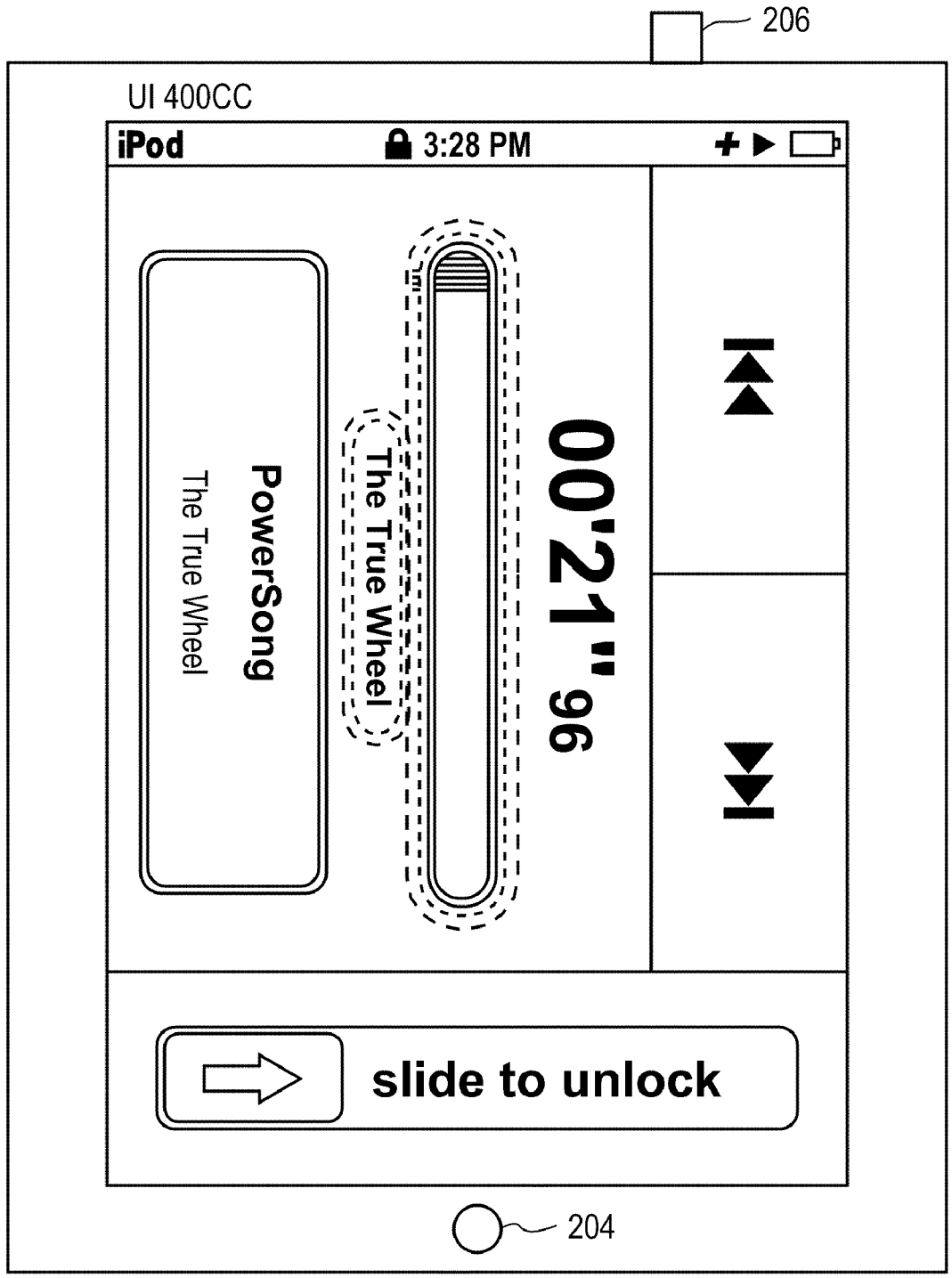
Figure 4D:
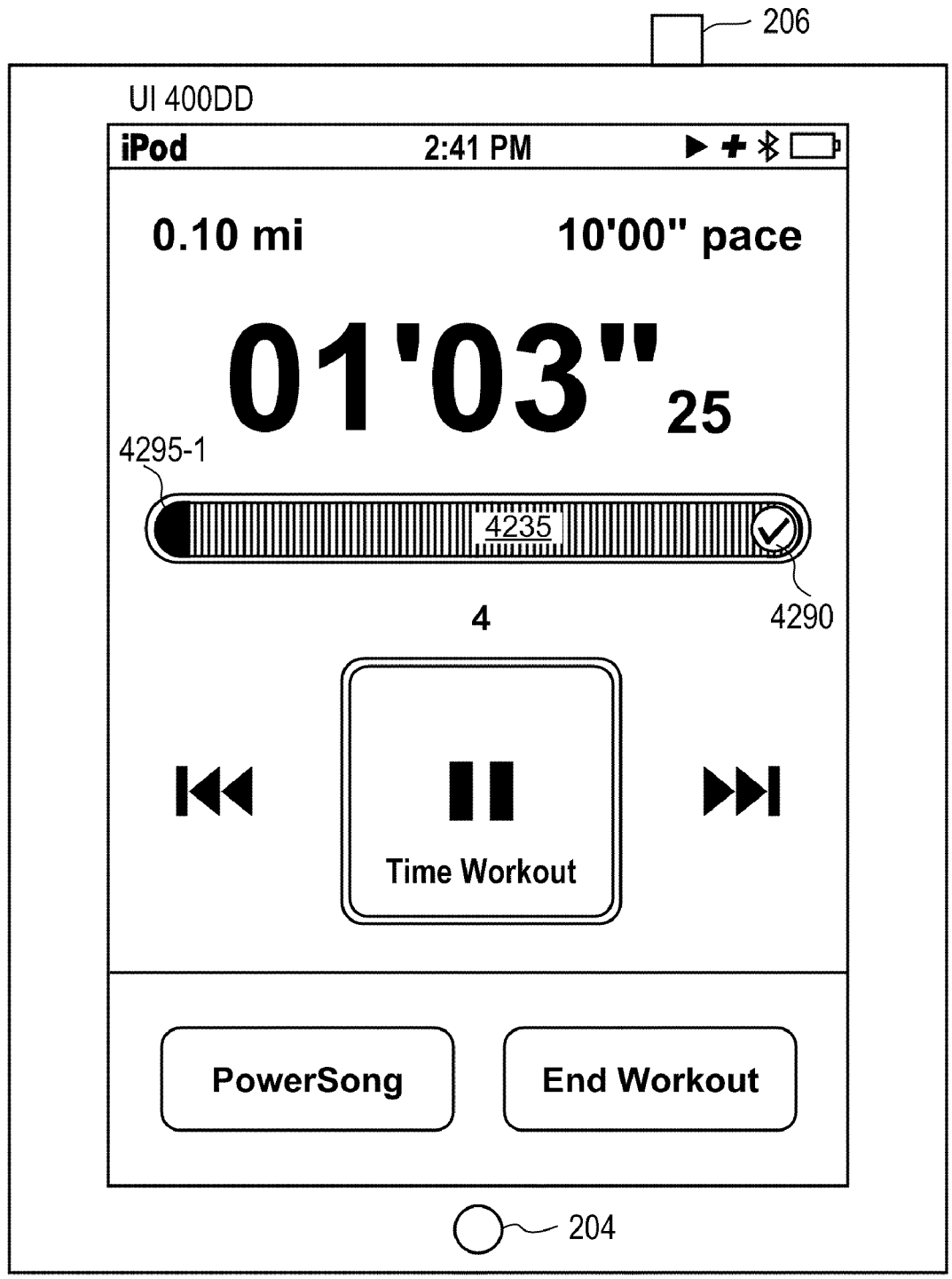
Figure 4E:
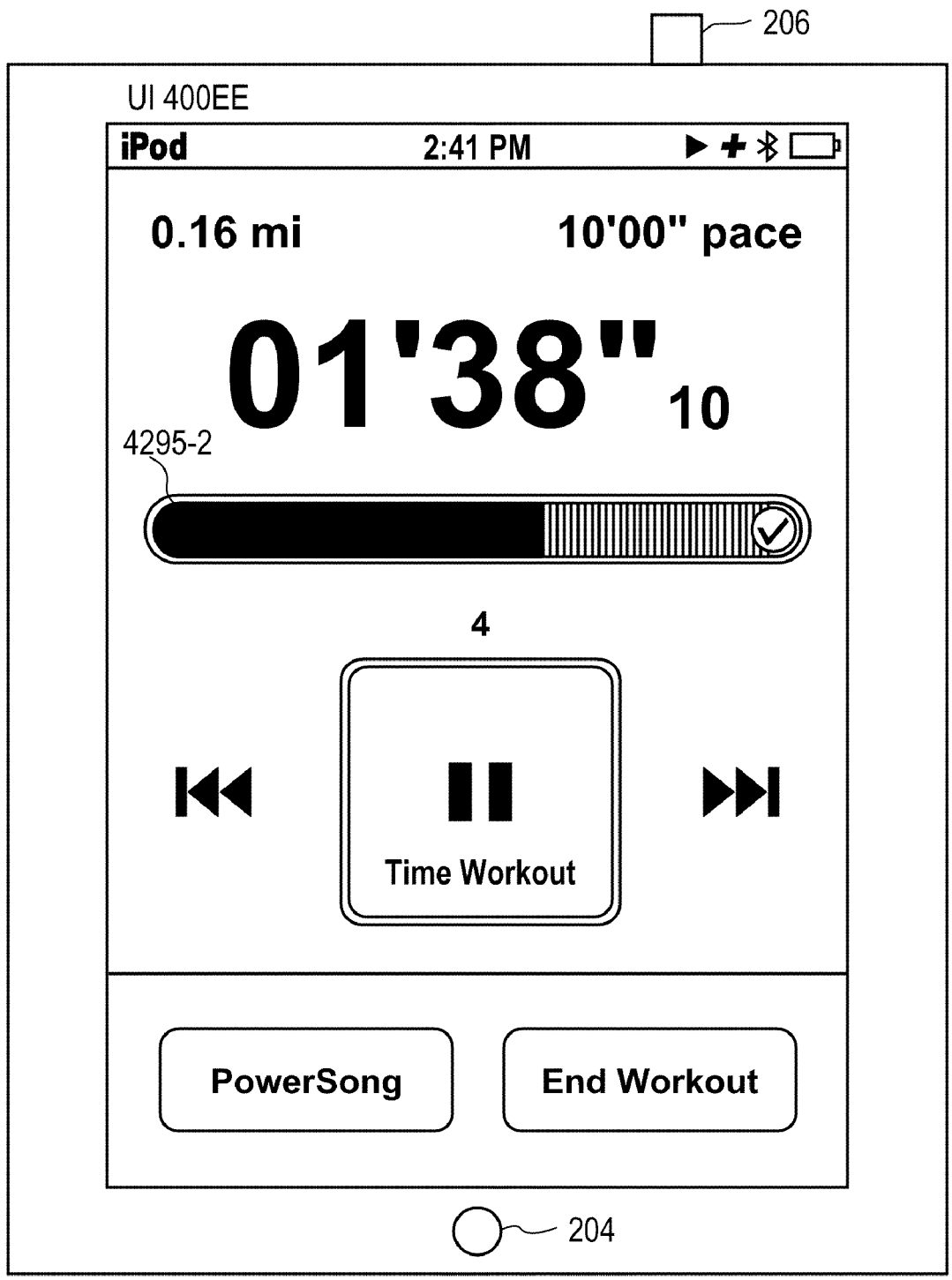
Figure 4F:
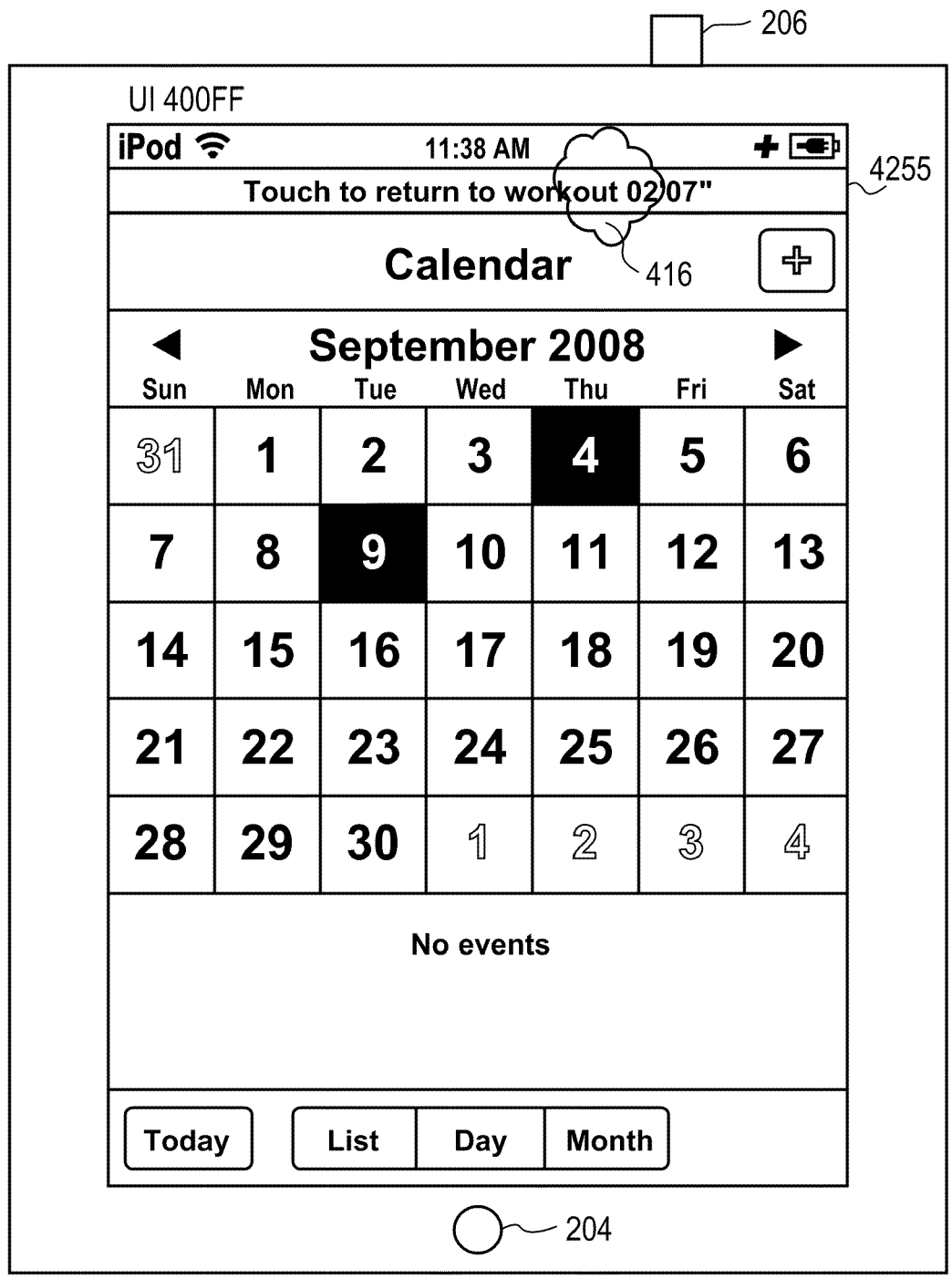
Figure 5B:
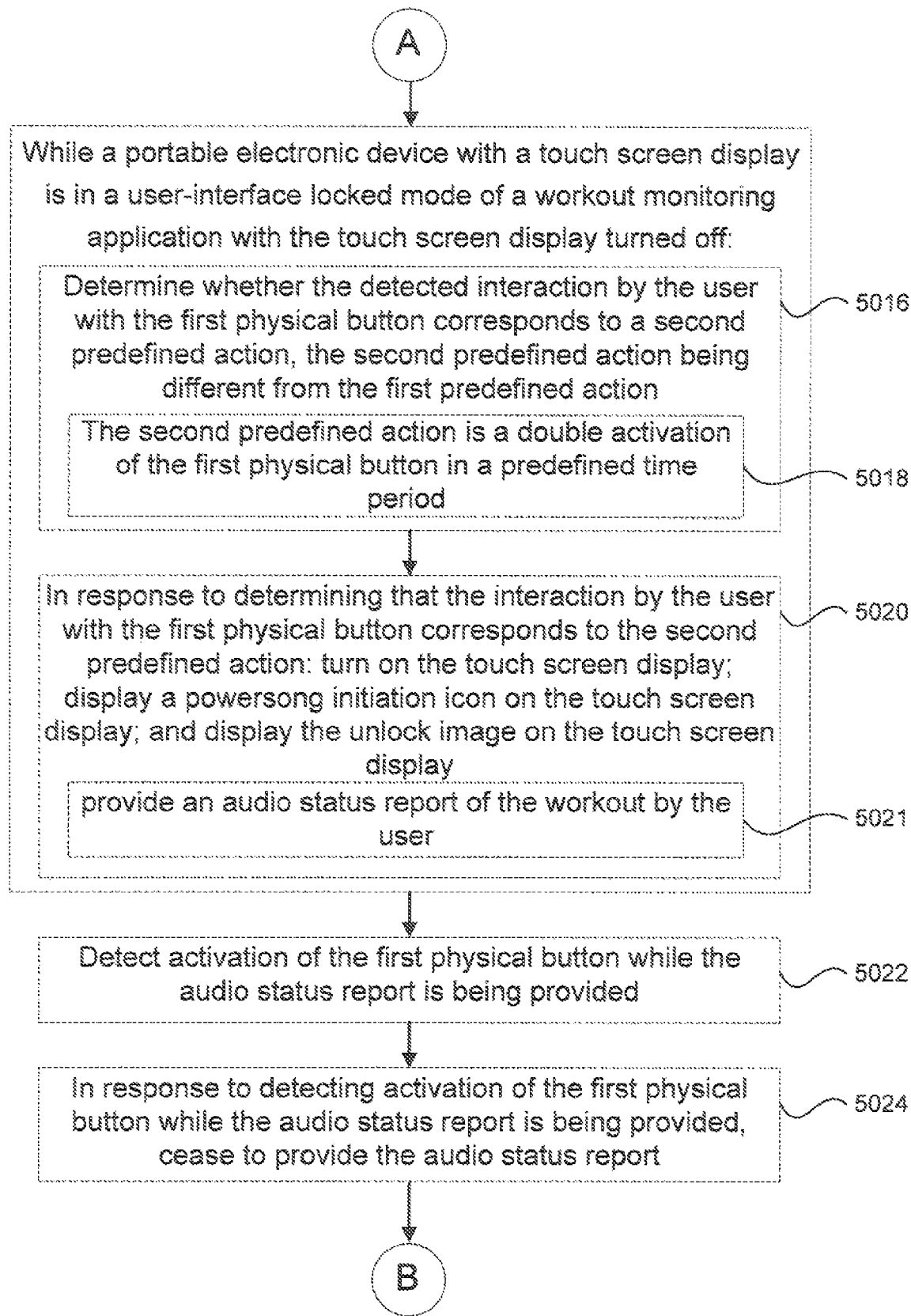
Figure 5C:
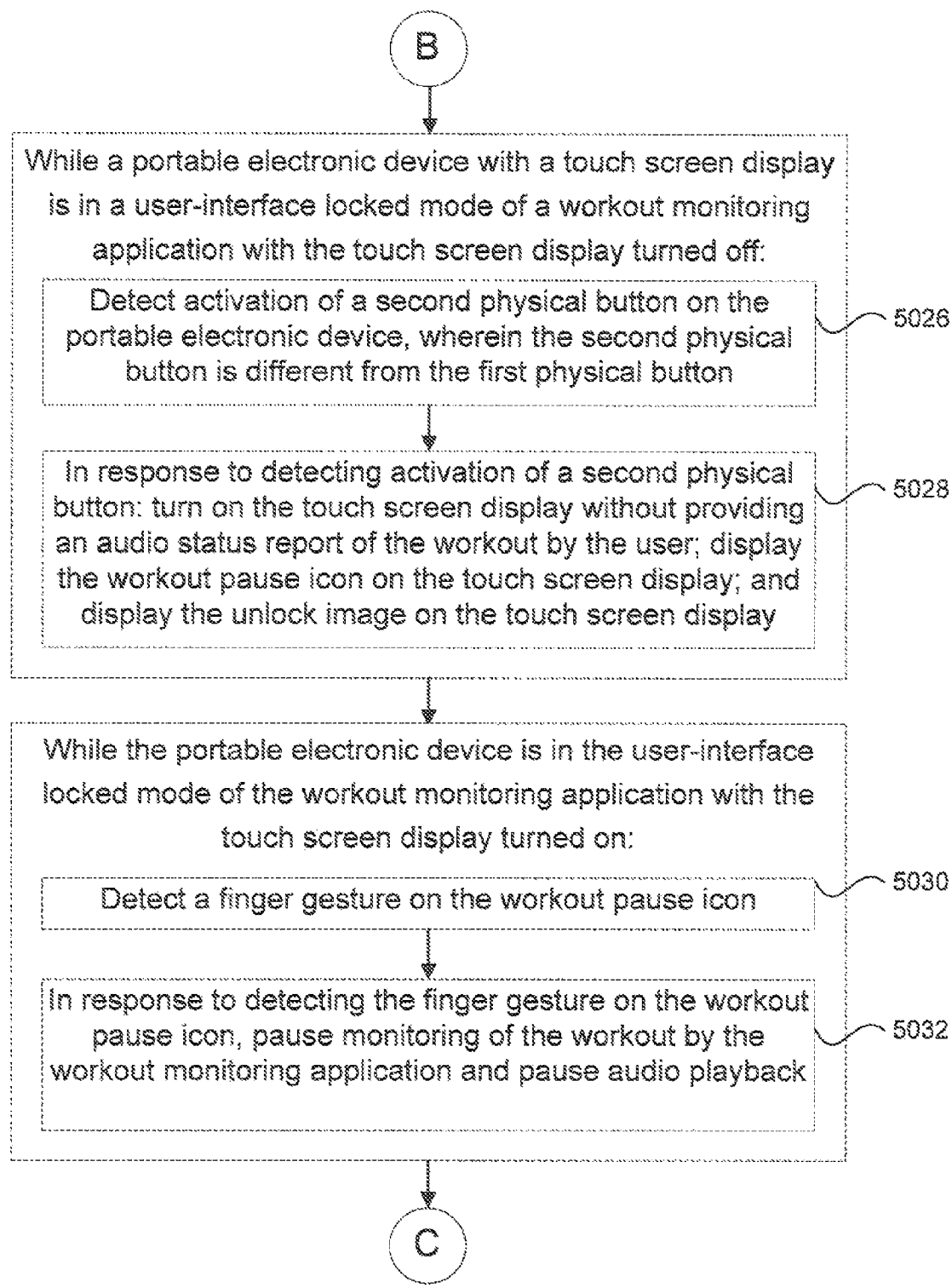
Figure 5D:
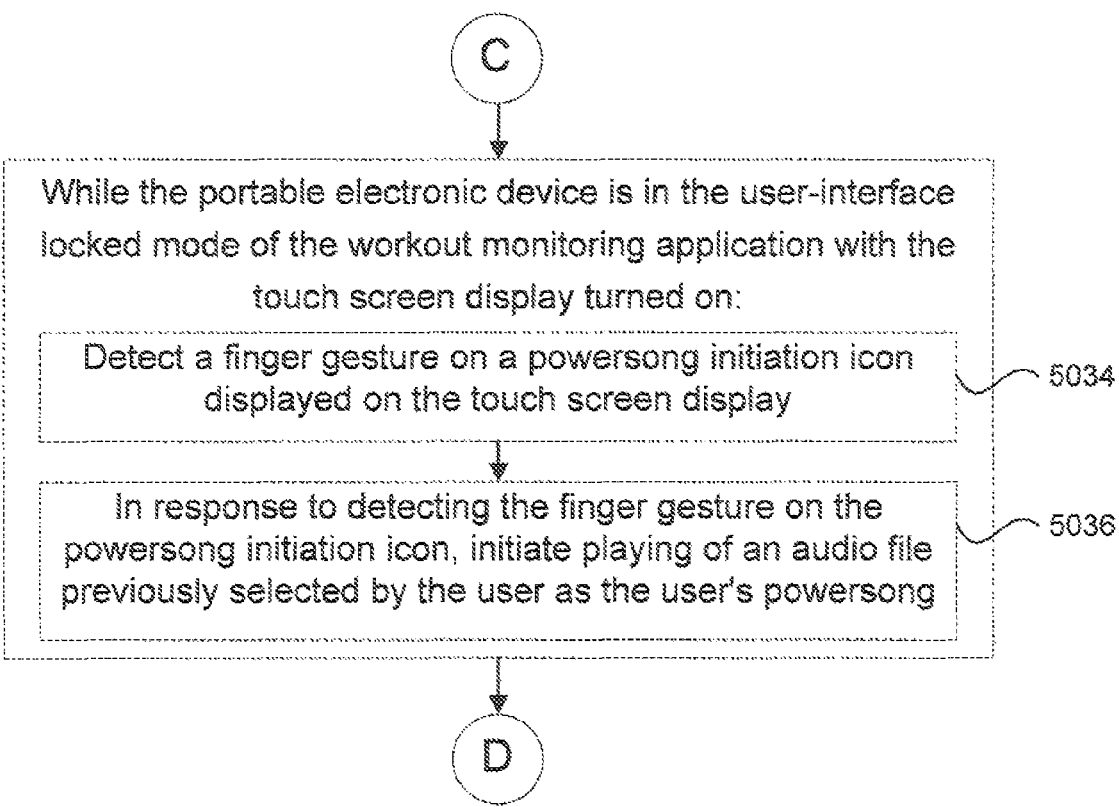
Figure 5E:
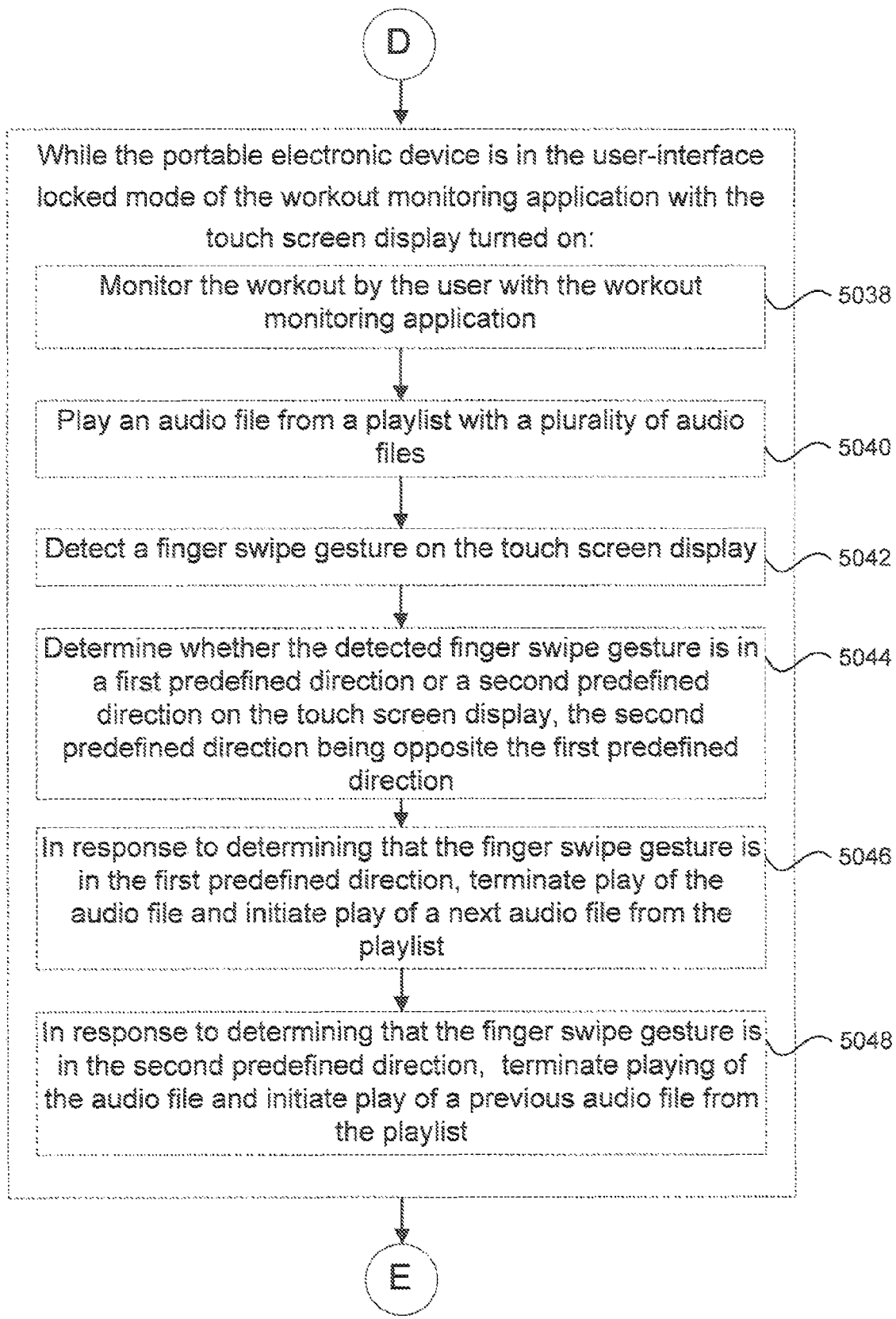
Figure 5F:
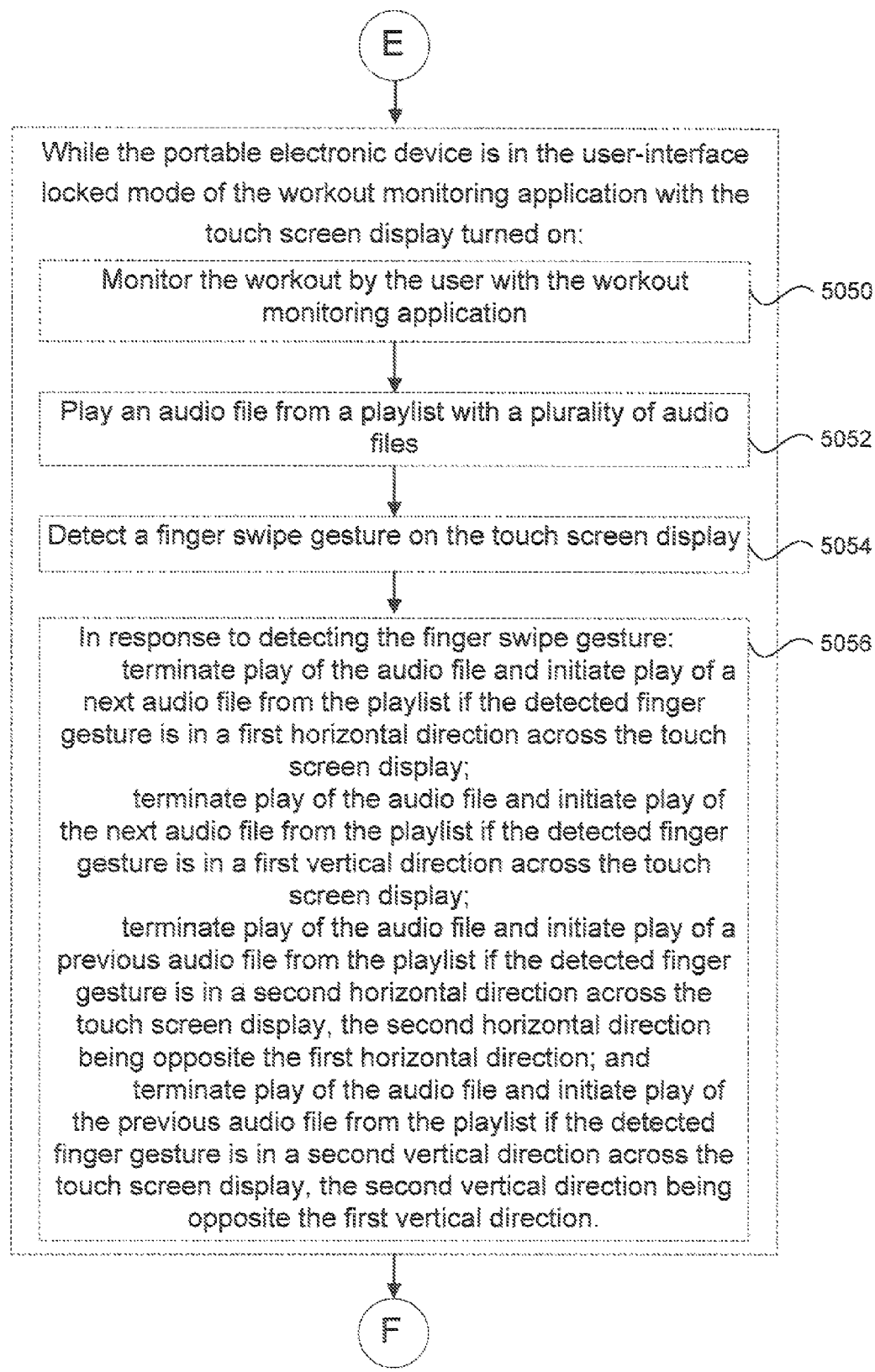
Figure 5G:
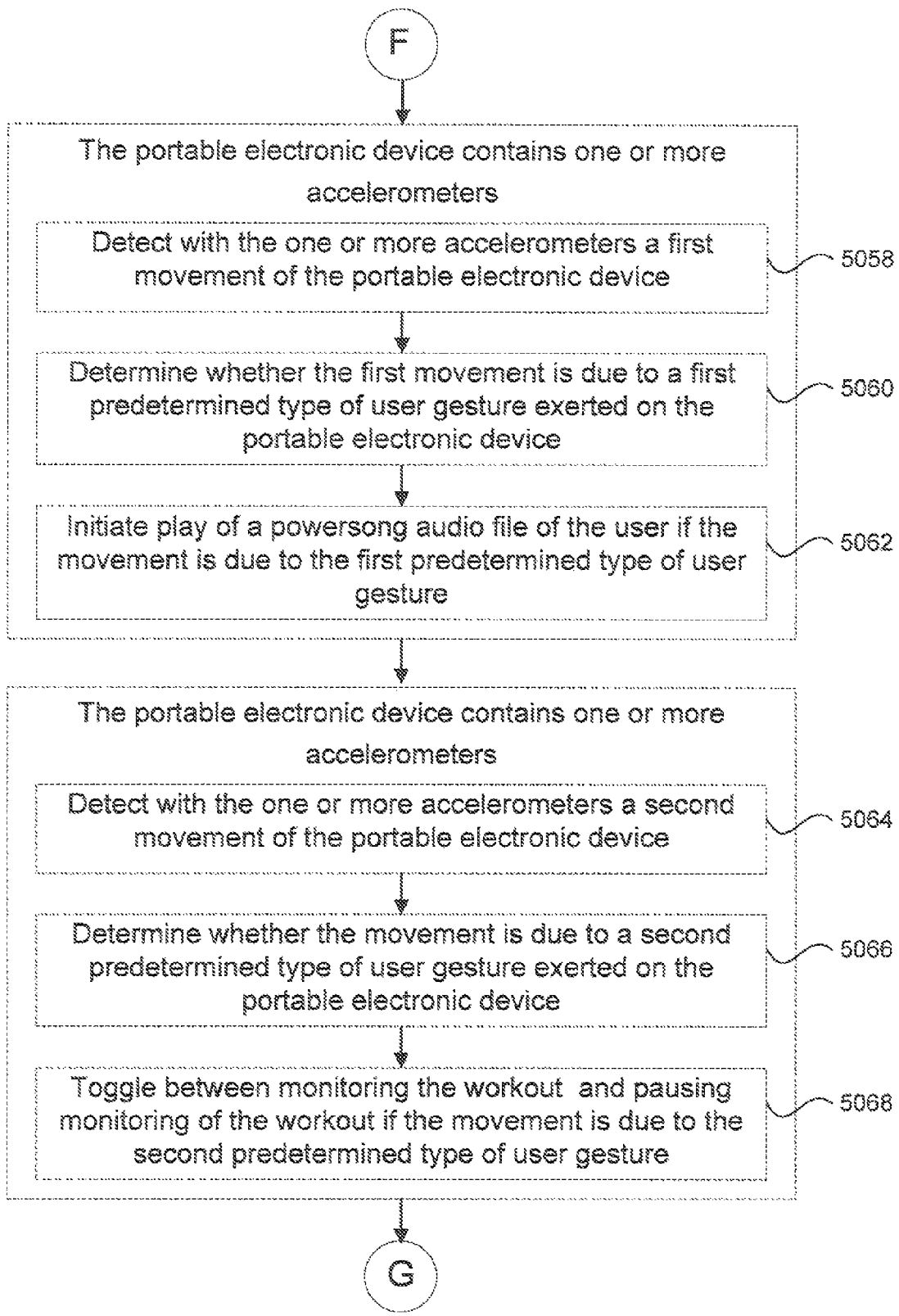
Figure 5H:
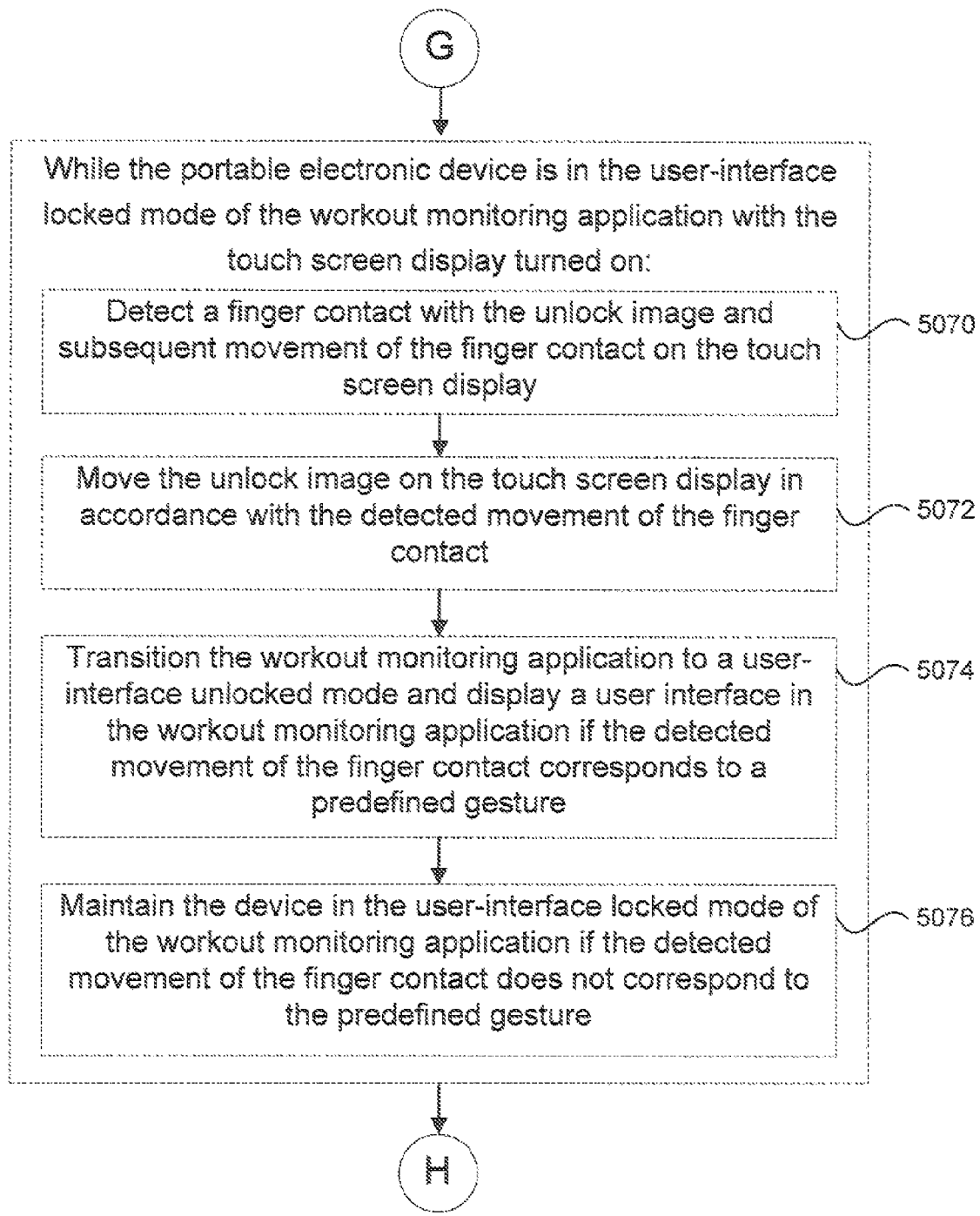
Figure 5I:
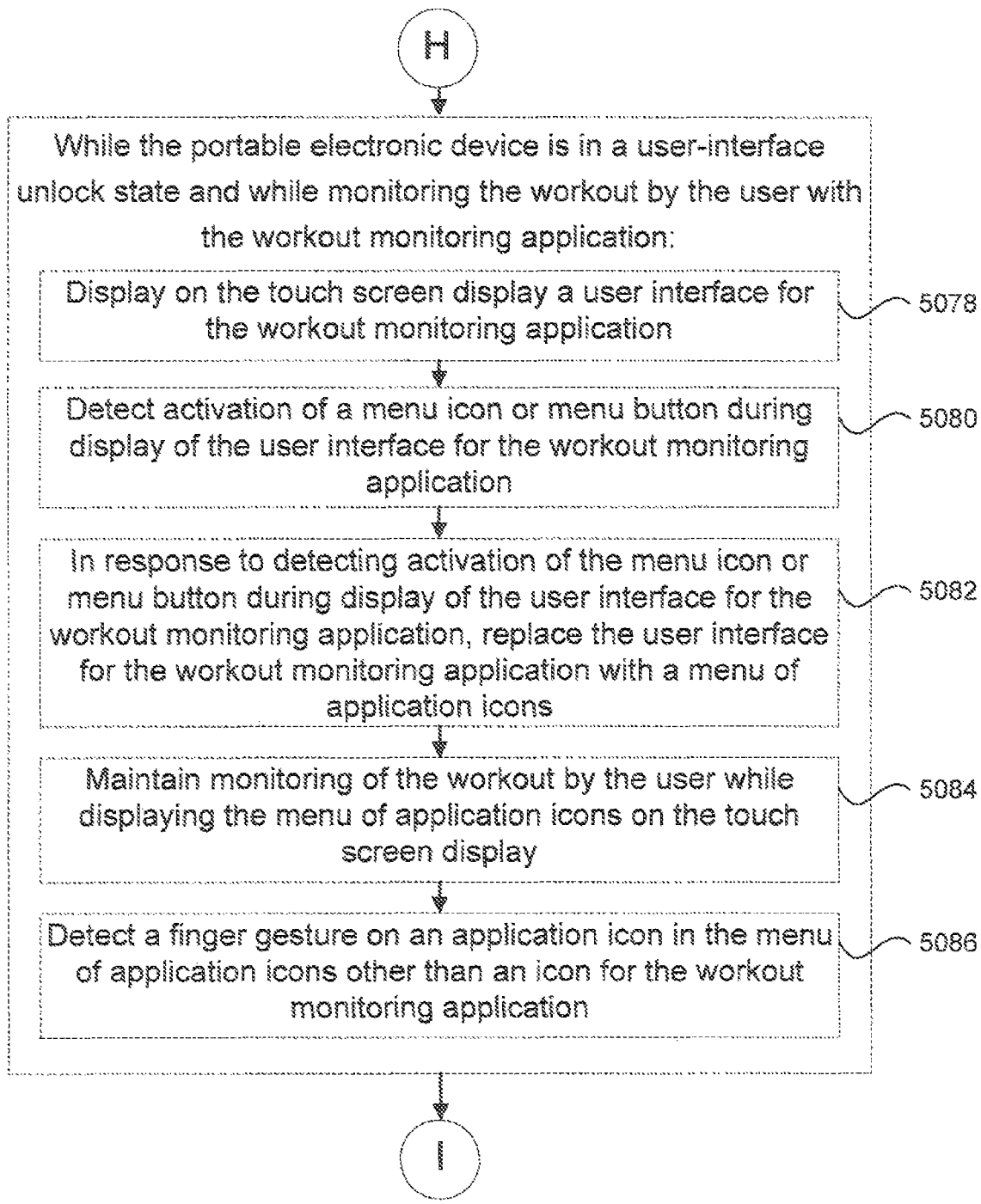

The device displays (6006) a workout progress bar on the touch screen display (e.g., progress bar 4235, FIG. 4W). The workout progress bar 4235 indicates a portion of the predetermined workout goal fulfilled by the user.

The device updates (6008) the workout progress bar 4235 to display the portion of the predetermined workout goal fulfilled by the user until the predetermined workout goal is met.

In some embodiments, the device detects (6010) fulfillment of the predetermined workout goal. In response to detecting fulfillment of the predetermined workout goal, the device displays (6012) an indicator that the predetermined workout goal has been reached (e.g., indicator 4290, FIG. 4DD). In some embodiments, the indicator 4290 that the predetermined workout goal has been reached is overlaid (6014) on the workout progress bar. In some embodiments, the indicator 4290 that the predetermined workout goal has been reached is overlaid (6016) on the post-workout-goal activity bar. In some embodiments, the indicator 4290 that the predetermined workout goal has been reached is a checkmark (6018).

The device displays (6020) a post-workout-goal activity bar on the touch screen display (e.g., bar 4295, FIG. 4DD). The post-workout-goal activity bar 4295 indicates activity by the user beyond the predetermined workout goal. In some embodiments, the post-workout-goal activity bar 4295 indicates (6022) time beyond the predetermined time for the workout (e.g., bar 4295, FIG. 4DD), distance beyond the predetermined distance to be traveled in the workout, or calories beyond the predetermined number of calories to be burned in the workout. In some embodiments, the post-workout-goal activity bar 4295 is displayed (6024) on the touch screen display in response to determining that the workout by the user has continued beyond the predetermined workout goal.

In some embodiments, the post-workout-goal activity bar 4295 is overlaid (6026) on the workout progress bar 4235. In some embodiments, the post-workout-goal activity bar 4295 replaces (6028) the workout progress bar 4235 on the touch screen display. In same embodiments, the post-workout-goal activity bar 4295 is adjacent (6030) to the workout progress bar 4235 on the touch screen display (not shown).

The device updates (6032) the post-workout-goal activity bar 4295 while the user continues to workout after reaching the predetermined workout goal.

In accordance with some embodiments, a graphical user interface on a portable electronic device 100 with a touch screen display 112 includes: a workout progress bar 4235 on the touch screen display that indicates a portion of a predetermined workout goal fulfilled by the user, and a post-workout-goal activity bar 4295 that indicates activity by the user beyond the predetermined workout goal. A workout by a user is monitored with a workout monitoring application 142. The workout progress bar 4235 is updated to display the portion of the predetermined workout goal fulfilled by the user until the predetermined workout goal is met. The post-workout-goal activity bar 4295 is updated while the user continues to workout after reaching the predetermined workout goal.

FIG. 7 is a flow diagram illustrating a method of initiating play of a powersong in accordance with some embodiments. The method 7000 is performed on a portable electronic device having a touch screen display (e.g., portable multifunction device 100).

Operations 7002 and 7004 are performed while the portable electronic device 100 is in a user-interface locked mode of a workout monitoring application with the touch screen display turned on. Typically, other applications on the device are also locked when the device is in this mode.

The device detects (7002) a finger gesture on a powersong initiation icon 4285 displayed on the touch screen display (e.g., tap gesture 404, FIG. 4BB) In response to detecting the finger gesture on the powersong initiation icon, the device initiates (7004) playing of an audio file previously selected by the user as the user's powersong.

Thus, with method 7000, the user can use a simple finger gesture (e.g., gesture 404, FIG. 4BB) on an enlarged icon while exercising to play a powersong while the workout support application and the device remain locked, without needing to see the touch screen display or make precise contacts with the display.

In accordance with some embodiments, a graphical user interface on a portable electronic device with a touch screen display includes a powersong initiation icon on the touch screen display (e.g., UI 400BB, FIG. 4BB with powersong initiation icon 4285). While the portable electronic device is in a user-interface locked mode of a workout monitoring application with the touch screen display turned on: a finger gesture is detected on the powersong initiation icon (e.g., tap gesture 404, FIG. 4BB); and, in response to detecting the finger gesture on the powersong initiation icon 4285, play is initiated of an audio file previously selected by the user as the user's powersong.

FIG. 8 is a flow diagram illustrating a method of initiating play of a next or previous audio file from a playlist is accordance with some embodiments. The method 8000 is performed on a portable electronic device having a touch screen display (e.g., portable multifunction device 100).

Operations 8002-8012 are performed while the portable electronic device 100 is in a user-interface locked mode of a workout monitoring application with the touch screen display turned on. Typically, other applications on the device are also locked when the device is in this mode.

The device monitors (8002) the workout by the user with the workout monitoring application 142. The device plays (8004) an audio file from a playlist with a plurality of audio files. The device detects (8006) a finger swipe gesture on the touch screen display. The device determines (8008) whether the detected finger swipe gesture is in a first predefined direction or a second predefined direction on the touch screen display, the second predefined direction being opposite the first predefined direction. For example, the device determines whether the swipe gesture is from right to left on the touch screen display (e.g. gesture 406, FIG. 4Z) or from left to right on the touch screen display (e.g., gesture 408, FIG. 4Z). As another example, the device determines whether the swipe gesture is vertically downward on the touch screen display (e.g., gesture 410, FIG. 4Z) or vertically upward on the touch screen display (e.g., gesture 412, FIG. 4Z). In some embodiments, the direction determination is independent of the location of the swipe gesture on the touch screen display. In response to determining that the finger swipe gesture is in the first predefined direction, the device terminates play of the audio file and initiates play of a next audio file from the playlist (8010). In response to determining that the finger swipe gesture is in the second predefined direction, the device terminates play of the audio file and initiates play of a previous audio file from the playlist (8012).

FIG. 9 is a flow diagram illustrating a method of initiating play of a next or previous audio file from a playlist in accordance with some embodiments. The method 9000 is performed on a portable electronic device having a touch screen display (e.g., portable multifunction device 100).

Operations 9002-9008 are performed while the portable electronic device 100 is in a user-interface locked mode of a workout monitoring application with the touch screen display turned on. Typically, other applications on the device are also locked when the device is in this mode.

The device monitors (9002) the workout by the user with the workout monitoring application 142. The device plays (9004) an audio file from a playlist with a plurality of audio files. The device detects (9006) a finger swipe gesture on the touch screen display. In response to detecting the finger swipe gesture, the device: terminates play of the audio file and initiates play of a next audio file from the playlist if the detected finger gesture is in a first horizontal or substantially horizontal direction (e.g., swipe gesture 406, FIG. 4Z, moving from right to left across the touch screen display within a predetermined angle of the horizontal axis of the touch screen display) across the touch screen display; terminates play of the audio file and initiates play of the next audio file from the playlist if the detected finger gesture is in a first vertical or substantially vertical direction (e.g., swipe gesture 410, FIG. 4Z, moving from top to bottom across the touch screen display within a predetermined angle of the vertical axis of the touch screen display) across the touch screen display; terminates play of the audio file and initiates play of a previous audio file from the playlist if the detected finger gesture is in a second horizontal or substantially horizontal direction (e.g., swipe gesture 408, FIG. 4Z, moving from left to right across the touch screen display within a predetermined angle of the horizontal axis of the touch screen display) across the touch screen display, the second horizontal direction being opposite the first horizontal direction; and terminates play of the audio file and initiates play of the previous audio file from the playlist if the detected finger gesture is in a second vertical or substantially vertical direction (e.g., swipe gesture 412, FIG. 4Z, moving from bottom to top across the touch screen display within a predetermined angle of the vertical axis of the touch screen display) across the touch screen display, the second vertical direction being opposite the first vertical direction (9008).

Thus, with methods 8000 and 9000, the user can use simple finger swipe gestures (e.g., gestures 406, 408, 410, and/or 412, FIG. 4Z) while exercising to play a next track or a previous track while the workout support application and the device remain locked, without needing to see the touch screen display or make precise contacts with the display.

FIG. 10 is a flow diagram illustrating a method of controlling an application with finger gestures while the application is in a user-interface locked mode of operation in accordance with some embodiments. The method 1000 is performed on a portable electronic device having a touch screen display (e.g., portable multifunction device 100).

Operations 1002-1016 are performed while the portable electronic device 100 is in a user-interface locked mode of an application with the touch screen display turned on. Typically, other applications on the device are also locked when the device is in this mode.

The device displays (1002) a locked-mode user interface for the application. In some embodiments, the displayed locked-mode user interface for the application comprises an unlock screen for the application (e.g., UI 400Z, FIG. 4Z, for workout support application 142) (1004). In some embodiments, the displayed locked-mode user interface for the application comprises an unlock image (1006). The unlock image is a graphical user interface object with which the user interacts in order to change the application to a user-interface unlocked mode (e.g., unlock image 4260, FIG. 4Z), as described above.

In some embodiments, the application is an application that provides audio output (1008). In some embodiments, the application is a workout support application 142 (1010). In some embodiments, the application is a music player application 146 (1012).

The device detects (1014) a finger gesture on the touch screen display (e.g., swipe gesture 406, FIG. 4Z). In response to detecting the finger gesture on the touch screen display, the device performs (1016) a control operation in the application while maintaining display of the same locked-mode user interface for the application. For example, in response to detecting swipe gesture 406 on the touch screen display, the device terminates play of as audio file and initiates play of a next audio file from a playlist while maintaining display of the same locked-mode user interface UI 400Z for the workout support application 142.

In some embodiments, after performing the control operation in the application, the device turns off the touch screen display after a predetermined time (e.g., 30 seconds, 1 minute, or a user-specified time) without detecting additional user input in order to conserve power.

Thus, with method 1000, the user can use a simple finger gestures (e.g., swipe gestures 406, 408, 410, and 412, FIG. 4Z to control an application while the application is in a user-interface locked mode of operation, without needing to see the touch screen display or make precise contacts with the display.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled is the art to best utilize the invention and various embodiments with various modifications as are suited to the particular use contemplated.

What is claimed is:
1. A computer-implemented method, comprising:
 at a portable electronic device with a touch screen display:
  while the portable electronic device is in a user-interface locked mode of a workout monitoring application with the touch screen display turned off:
   monitoring a workout by a user with the workout monitoring application;
   detecting an interaction by the user with a first physical button on the portable electronic device;
   determining whether the detected interaction by the user with the first physical button corresponds to a first predefined action;
   in response to determining that the interaction by the user with the first physical button corresponds to the first predefined action:
    turning on the touch screen display;
    displaying a workout pause icon on the touch screen display; and
    displaying an unlock image on the touch screen display, wherein the unlock image is a graphical user interface object with which the user interacts in order to change the workout monitoring application to a user-interface unlocked mode; and while the portable electronic device is in the user-interface locked mode of the workout monitoring application with the touch screen display turned on:
   monitoring the workout by the user with the workout monitoring application;
   playing an audio file from a playlist with a plurality of audio files;
   detecting a finger swipe gesture on the touch screen display;
   in response to detecting the finger swipe gesture:
     terminating play of the audio file and initiating play of a next audio file from the playlist if the detected finger gesture is in a first horizontal direction, relative to the device, across the touch screen display;
     terminating play of the audio file and initiating play of the next audio file from the playlist if the detected finger gesture is in a first vertical direction, relative to the device, across the touch screen display;
     terminating play of the audio file and initiating play of a previous audio file from the playlist if the detected finger gesture is in a second horizontal direction, relative to the device, across the touch screen display, the second horizontal direction being opposite the first horizontal direction; and
     terminating play of the audio file and initiating play of the previous audio file from the playlist if the detected finger gesture is in a second vertical direction, relative to the device, across the touch screen display, the second vertical direction being opposite the first vertical direction.

2. The computer-implemented method of claim 1, including:
   providing an audio status report of the workout by the user in response to determining that the interaction by the user with the first physical button corresponds to the first predefined action.

3. The computer-implemented method of claim 1, including:
   determining whether the detected interaction by the user with the first physical button corresponds to a second predefined action, the second predefined action being different from the first predefined action;
   in response to determining that the interaction by the user with the first physical button corresponds to the second predefined action:
     turning on the touch screen display;
     displaying a powersong initiation icon on the touch screen display; and
     displaying the unlock image on the touch screen display.

4. The computer-implemented method of claim 3, including:
   providing an audio status report of the workout by the user in response to determining that the interaction by the user with the first physical button corresponds to the second predefined action.

5. The computer-implemented method of claim 3, wherein the second predefined action is a double activation of the first physical button in a predefined time period.

6. The computer-implemented method of claim 3, including:
   while the portable electronic device is in the user-interface locked mode of the workout monitoring application with the touch screen display turned on:
     detecting a finger gesture on the powersong initiation icon displayed on the touch screen display; and
     in response to detecting the finger gesture on the powersong initiation icon, initiating playing of an audio file previously selected by the user as the user's powersong.

7. The computer-implemented method of claim 1, wherein monitoring the workout includes receiving data from a sensor that is separate from the portable electronic device.

8. The computer-implemented method of claim 1, including, while the portable electronic device is in the user-interface locked mode of the workout monitoring application with the touch screen display turned off, playing an audio file from a playlist with a plurality of audio files.

9. The computer-implemented method of claim 1, wherein the first predefined action is a single activation of the first physical button in a predefined time period.

10. The computer-implemented method of claim 1, including:
   detecting activation of the first physical button while an audio status report is being provided; and
   in response to detecting activation of the first physical button while the audio status report is being provided, ceasing to provide the audio status report.

11. The computer-implemented method of claim 1, including:
   while the portable electronic device is in the user-interface locked mode of the workout monitoring application with the touch screen display turned off:
     detecting activation of a second physical button on the portable electronic device, wherein the second physical button is different from the first physical button;
     in response to detecting activation of a second physical button:
       turning on the touch screen display without providing an audio status report of the workout by the user;
       displaying the workout pause icon on the touch screen display; and
       displaying the unlock image on the touch screen display.

12. The computer-implemented method of claim 1, including:
   while the portable electronic device is in the user-interface locked mode of the workout monitoring application with the touch screen display turned on:
     detecting a finger gesture on the workout pause icon; and
     in response to detecting the finger gesture on the workout pause icon, pausing monitoring of the workout by the workout monitoring application.

13. The computer-implemented method of claim 1, wherein the portable electronic device contains one or more accelerometers, including:
   detecting with the one or more accelerometers a first movement of the portable electronic device;
   determining whether the first movement is due to a first predetermined type of user gesture exerted on the portable electronic device; and
   initiating play of a powersong audio file of the user if the movement is due to the first predetermined type of user gesture.

14. The computer-implemented method of claim 1, wherein the portable electronic device contains one or more accelerometers, including:
   detecting with the one or more accelerometers a movement of the portable electronic device;
   determining whether the movement is due to a second predetermined type of user gesture exerted on the portable electronic device; and toggling between monitoring the workout and pausing monitoring of the workout if the movement is due to the second predetermined type of user gesture.

15. The computer-implemented method of claim 1, including:
while the portable electronic device is in the user-interface locked mode of the workout monitoring application with the touch screen display turned on:
detecting a finger contact with the unlock image and subsequent movement of the finger contact on the touch screen display;
moving the unlock image on the touch screen display in accordance with the detected movement of the finger contact;
transitioning the workout monitoring application to a user-interface unlocked mode and displaying a user interface in the workout monitoring application if the detected movement of the finger contact corresponds to a predefined gesture; and
maintaining the device in the user-interface locked mode of the workout monitoring application if the detected movement of the finger contact does not correspond to the predefined gesture.

16. The computer-implemented method of claim 1, including:
while the portable electronic device is in a user-interface unlocked mode and while monitoring the workout by the user with the workout monitoring application:
displaying on the touch screen display a user interface for the workout monitoring application;
detecting activation of a menu icon or menu button during display of the user interface for the workout monitoring application;
in response to detecting activation of the menu icon or menu button during display of the user interface for the workout monitoring application, replacing the user interface for the workout monitoring application with a menu of application icons;
maintaining monitoring of the workout by the user while displaying the menu of application icons on the touch screen display;
detecting a finger gesture on an application icon in the menu of application icons other than an icon for the workout monitoring application;
in response to detecting a finger gesture on the application icon in the menu of application icons other than the icon for the workout monitoring application, displaying a user interface for a corresponding application on the touch screen display while continuing to maintain monitoring of the workout by the user, wherein the user interface for the corresponding application includes a return-to-workout-monitoring-application icon that is not displayed in the user interface for the corresponding application when there is no ongoing monitoring of the workout by the user;
detecting a finger gesture on the return-to-workout-monitoring-application icon; and
in response to detecting the finger gesture on the return-to-workout-monitoring-application icon, replacing display of the user interface for the corresponding application with a respective user interface for the workout monitoring application while continuing to monitor the workout by the user.

17. The computer-implemented method of claim 1, including transitioning the portable electronic device to a user-interface locked mode of the workout monitoring application upon expiration of a pre-determined time period without detecting user input to the device.

18. A portable electronic device, comprising:
a touch screen display;
one or more processors;
memory; and
one or more programs, wherein the one or more programs are stored in the memory and configured to be executed by the one or more processors, the one or more programs including instructions for:
while the portable electronic device is in a user-interface locked mode of a workout monitoring application with the touch screen display turned off:
monitoring a workout by a user with the workout monitoring application;
detecting an interaction by the user with a first physical button on the portable electronic device;
determining whether the detected interaction by the user with the first physical button corresponds to a first predefined action;
in response to determining that the interaction by the user with the first physical button corresponds to the first predefined action:
turning on the touch screen display;
displaying a workout pause icon on the touch screen display; and
displaying an unlock image on the touch screen display, wherein the unlock image is a graphical user interface object with which the user interacts in order to change the workout monitoring application to a user-interface unlocked mode; and
while the portable electronic device is in the user-interface locked mode of the workout monitoring application with the touch screen display turned on:
monitoring the workout by the user with the workout monitoring application;
playing an audio file from a playlist with a plurality of audio files;
detecting a finger swipe gesture on the touch screen display;
in response to detecting the finger swipe gesture:
terminating play of the audio file and initiating play of a next audio file from the playlist if the detected finger gesture is in a first horizontal direction, relative to the device, across the touch screen display;
terminating play of the audio file and initiating play of the next audio file from the playlist if the detected finger gesture is in a first vertical direction, relative to the device, across the touch screen display;
terminating play of the audio file and initiating play of a previous audio file from the playlist if the detected finger gesture is in a second horizontal direction, relative to the device, across the touch screen display, the second horizontal direction being opposite the first horizontal direction; and
terminating play of the audio file and initiating play of the previous audio file from the playlist if the detected finger gesture is in a second vertical direction, relative to the device, across the touch screen display, the second vertical direction being opposite the first vertical direction.

19. The device of claim 18, including instructions for:
providing an audio status report of the workout by the user in response to determining that the interaction by the user with the first physical button corresponds to the first predefined action.

20. The device of claim 18, including instructions for:
  determining whether the detected interaction by the user with the first physical button corresponds to a second predefined action, the second predefined action being different from the first predefined action;
  in response to determining that the interaction by the user with the first physical button corresponds to the second predefined action:
    turning on the touch screen display;
    displaying a powersong initiation icon on the touch screen display; and
    displaying the unlock image on the touch screen display.

21. The device of claim 20, including instructions for:
  providing an audio status report of the workout by the user in response to determining that the interaction by the user with the first physical button corresponds to the second predefined action.

22. The device of claim 20, including instructions for, wherein the second predefined action is a double activation of the first physical button in a predefined time period.

23. The device of claim 20, including instructions for:
  while the portable electronic device is in the user-interface locked mode of the workout monitoring application with the touch screen display turned on:
    detecting a finger gesture on the powersong initiation icon displayed on the touch screen display; and
    in response to detecting the finger gesture on the powersong initiation icon, initiating playing of an audio file previously selected by the user as the user's powersong.

24. The device of claim 18, wherein monitoring the workout includes receiving data from a sensor that is separate from the portable electronic device.

25. The device of claim 18, including instructions for, while the portable electronic device is in the user-interface locked mode of the workout monitoring application with the touch screen display turned off, playing an audio file from a playlist with a plurality of audio files.

26. The device of claim 18, wherein the first predefined action is a single activation of the first physical button in a predefined time period.

27. The device of claim 18, including instructions for:
  detecting activation of the first physical button while an audio status report is being provided; and
  in response to detecting activation of the first physical button while the audio status report is being provided, ceasing to provide the audio status report.

28. The device of claim 18, including instructions for:
  while the portable electronic device is in the user-interface locked mode of the workout monitoring application with the touch screen display turned off:
    detecting activation of a second physical button on the portable electronic device, wherein the second physical button is different from the first physical button;
    in response to detecting activation of a second physical button:
      turning on the touch screen display without providing an audio status report of the workout by the user;
      displaying the workout pause icon on the touch screen display; and
      displaying the unlock image on the touch screen display.

29. The device of claim 18, including instructions for:
  while the portable electronic device is in the user-interface locked mode of the workout monitoring application with the touch screen display turned on:
    detecting a finger gesture on the workout pause icon; and
    in response to detecting the finger gesture on the workout pause icon, pausing monitoring of the workout by the workout monitoring application.

30. The device of claim 18, wherein the portable electronic device contains one or more accelerometers, including instructions for:
  detecting with the one or more accelerometers a first movement of the portable electronic device;
  determining whether the first movement is due to a first predetermined type of user gesture exerted on the portable electronic device; and
  initiating play of a powersong audio file of the user if the movement is due to the first predetermined type of user gesture.

31. The device of claim 18, wherein the portable electronic device contains one or more accelerometers, including instructions for:
  detecting with the one or more accelerometers a movement of the portable electronic device;
  determining whether the movement is due to a second predetermined type of user gesture exerted on the portable electronic device; and
  toggling between monitoring the workout and pausing monitoring of the workout if the movement is due to the second predetermined type of user gesture.

32. The device of claim 18, including instructions for:
  while the portable electronic device is in the user-interface locked mode of the workout monitoring application with the touch screen display turned on:
    detecting a finger contact with the unlock image and subsequent movement of the finger contact on the touch screen display;
    moving the unlock image on the touch screen display in accordance with the detected movement of the finger contact;
    transitioning the workout monitoring application to a user-interface unlocked mode and displaying a user interface in the workout monitoring application if the detected movement of the finger contact corresponds to a predefined gesture; and
    maintaining the device in the user-interface locked mode of the workout monitoring application if the detected movement of the finger contact does not correspond to the predefined gesture.

33. The device of claim 18, including instructions for:
  while the portable electronic device is in a user-interface unlocked mode and while monitoring the workout by the user with the workout monitoring application:
    displaying on the touch screen display a user interface for the workout monitoring application;
    detecting activation of a menu icon or menu button during display of the user interface for the workout monitoring application;
    in response to detecting activation of the menu icon or menu button during display of the user interface for the workout monitoring application, replacing the user interface for the workout monitoring application with a menu of application icons;
    maintaining monitoring of the workout by the user while displaying the menu of application icons on the touch screen display;
    detecting a finger gesture on an application icon in the menu of application icons other than an icon for the workout monitoring application;
    in response to detecting a finger gesture on the application icon in the menu of application icons other than the icon for the workout monitoring application, displaying a user interface for a corresponding application on the touch screen display while continuing to maintain monitoring of the workout by the user, wherein the user interface for the corresponding application includes a return-to-workout-monitoring-application icon that is not displayed in the user interface for the corresponding application when there is no ongoing monitoring of the workout by the user;

detecting a finger gesture on the return-to-workout-monitoring-application icon; and in response to detecting the finger gesture on the return-to-workout-monitoring-application icon, replacing display of the user interface for the corresponding application with a respective user interface for the workout monitoring application while continuing to monitor the workout by the user.

34. The device of claim 18, including instructions for transitioning the portable electronic device to a user-interface locked mode of the workout monitoring application upon expiration of a pre-determined time period without detecting user input to the device.

35. A non-transitory computer readable storage medium having stored therein instructions, which when executed by a portable electronic device with a touch screen display, cause the device to:

while the portable electronic device is in a user-interface locked mode of a workout monitoring application with the touch screen display turned off:

monitor a workout by a user with the workout monitoring application;

detect an interaction by the user with a first physical button on the portable electronic device;

determine whether the detected interaction by the user with the first physical button corresponds to a first predefined action;

in response to determining that the interaction by the user with the first physical button corresponds to the first predefined action:

turn on the touch screen display;

display a workout pause icon on the touch screen display; and display an unlock image on the touch screen display, wherein the unlock image is a graphical user interface object with which the user interacts in order to change the workout monitoring application to a user-interface unlocked mode; and while the portable electronic device is in the user-interface locked mode of the workout monitoring application with the touch screen display turned on:

monitor the workout by the user with the workout monitoring application;

play an audio file from a playlist with a plurality of audio files;

detect a finger swipe gesture on the touch screen display;

in response to detecting the finger swipe gesture:

terminate play of the audio file and initiating play of a next audio file from the playlist if the detected finger gesture is in a first horizontal direction, relative to the device, across the touch screen display;

terminate play of the audio file and initiating play of the next audio file from the playlist if the detected finger gesture is in a first vertical direction, relative to the device, across the touch screen display;

terminate play of the audio file and initiating play of a previous audio file from the playlist if the detected finger gesture is in a second horizontal direction, relative to the device, across the touch screen display, the second horizontal direction being opposite the first horizontal direction; and terminate play of the audio file and initiating play of the previous audio file from the playlist if the detected finger gesture is in a second vertical direction, relative to the device, across the touch screen display, the second vertical direction being opposite the first vertical direction.

36. The computer readable storage medium of claim 35, including instructions which cause the device to:

provide an audio status report of the workout by the user in response to determining that the interaction by the user with the first physical button corresponds to the first predefined action.

37. The computer readable storage medium of claim 35, including instructions which cause the device to:

determine whether the detected interaction by the user with the first physical button corresponds to a second predefined action, the second predefined action being different from the first predefined action;

in response to determining that the interaction by the user with the first physical button corresponds to the second predefined action:

turn on the touch screen display;

display a powersong initiation icon on the touch screen display; and display the unlock image on the touch screen display.

38. The computer readable storage medium of claim 37, including instructions which cause the device to:

provide an audio status report of the workout by the user in response to determining that the interaction by the user with the first physical button corresponds to the second predefined action.

39. The computer readable storage medium of claim 37, wherein the second predefined action is a double activation of the first physical button in a predefined time period.

40. The computer readable storage medium of claim 37, including instructions which cause the device to:

while the portable electronic device is in the user-interface locked mode of the workout monitoring application with the touch screen display turned on:

detect a finger gesture on the powersong initiation icon displayed on the touch screen display; and in response to detecting the finger gesture on the powersong initiation icon, initiate playing of an audio file previously selected by the user as the user's powersong.

41. The computer readable storage medium of claim 35, wherein monitoring the workout includes receiving data from a sensor that is separate from the portable electronic device.

42. The computer readable storage medium of claim 35, including instructions which cause the device to, while the portable electronic device is in the user-interface locked mode of the workout monitoring application with the touch screen display turned off, play an audio file from a playlist with a plurality of audio files.

43. The computer readable storage medium of claim 35, wherein the first predefined action is a single activation of the first physical button in a predefined time period.

44. The computer readable storage medium of claim 35, including instructions which cause the device to:

detect activation of the first physical button while an audio status report is being provided; and in response to detecting activation of the first physical button while the audio status report is being provided, cease to provide the audio status report.

45. The computer readable storage medium of claim 35, including instructions which cause the device to:
  while the portable electronic device is in the user-interface locked mode of the workout monitoring application with the touch screen display turned off:
    detect activation of a second physical button on the portable electronic device, wherein the second physical button is different from the first physical button;
    in response to detecting activation of a second physical button:
      turn on the touch screen display without providing an audio status report of the workout by the user;
      display the workout pause icon on the touch screen display; and
      display the unlock image on the touch screen display.

46. The computer readable storage medium of claim 35, including instructions which cause the device to:
  while the portable electronic device is in the user-interface locked mode of the workout monitoring application with the touch screen display turned on:
    detect a finger gesture on the workout pause icon; and
    in response to detecting the finger gesture on the workout pause icon, pause monitoring of the workout by the workout monitoring application.

47. The computer readable storage medium of claim 35, wherein the portable electronic device contains one or more accelerometers, including instructions which cause the device to:
  detect with the one or more accelerometers a first movement of the portable electronic device;
  determine whether the first movement is due to a first predetermined type of user gesture exerted on the portable electronic device; and
  initiate play of a powersong audio file of the user if the movement is due to the first predetermined type of user gesture.

48. The computer readable storage medium of claim 35, wherein the portable electronic device contains one or more accelerometers, including instructions which cause the device to:
  detect with the one or more accelerometers a movement of the portable electronic device;
  determine whether the movement is due to a second predetermined type of user gesture exerted on the portable electronic device; and
  toggle between monitoring the workout and pausing monitoring of the workout if the movement is due to the second predetermined type of user gesture.

49. The computer readable storage medium of claim 35, including instructions which cause the device to:
  while the portable electronic device is in the user-interface locked mode of the workout monitoring application with the touch screen display turned on:
    detect a finger contact with the unlock image and subsequent movement of the finger contact on the touch screen display;
    move the unlock image on the touch screen display in accordance with the detected movement of the finger contact;
    transition the workout monitoring application to a user-interface unlocked mode and displaying a user interface in the workout monitoring application if the detected movement of the finger contact corresponds to a predefined gesture; and
    maintain the device in the user-interface locked mode of the workout monitoring application if the detected movement of the finger contact does not correspond to the predefined gesture.

50. The computer readable storage medium of claim 35, including instructions which cause the device to:
  while the portable electronic device is in a user-interface unlocked mode and while monitoring the workout by the user with the workout monitoring application:
    display on the touch screen display a user interface for the workout monitoring application;
    detect activation of a menu icon or menu button during display of the user interface for the workout monitoring application;
    in response to detecting activation of the menu icon or menu button during display of the user interface for the workout monitoring application, replace the user interface for the workout monitoring application with a menu of application icons;
    maintain monitoring of the workout by the user while displaying the menu of application icons on the touch screen display;
    detect a finger gesture on an application icon in the menu of application icons other than an icon for the workout monitoring application;
    in response to detecting a finger gesture on the application icon in the menu of application icons other than the icon for the workout monitoring application, display a user interface for a corresponding application on the touch screen display while continuing to maintain monitoring of the workout by the user, wherein the user interface for the corresponding application includes a return-to-workout-monitoring-application icon that is not displayed in the user interface for the corresponding application when there is no ongoing monitoring of the workout by the user;
    detect a finger gesture on the return-to-workout-monitoring-application icon; and
    in response to detecting the finger gesture on the return-to-workout-monitoring-application icon, replace display of the user interface for the corresponding application with a respective user interface for the workout monitoring application while continuing to monitor the workout by the user.

51. The computer readable storage medium of claim 35, including instructions which cause the device to transition the portable electronic device to a user-interface locked mode of the workout monitoring application upon expiration of a predetermined time period without detecting user input to the device.

52. A graphical user interface on a portable electronic device with a touch screen display, a memory, and one or more processors to execute one or more programs stored in the memory, the graphical user interface comprising:
  a workout pause icon on the touch screen display; and
  an unlock image on the touch screen display, wherein the unlock image is a graphical user interface object with which the user interacts in order to change a workout monitoring application to a user-interface unlocked mode;
  wherein, while the portable electronic device is in a user-interface locked mode of a workout monitoring application with the touch screen display turned off:
    a workout by a user is monitored with the workout monitoring application;
    an interaction by the user with a first physical button on the portable electronic device is detected;

whether the detected interaction by the user with the first physical button corresponds to a first predefined action is determined;
in response to determining that the interaction by the user with the first physical button corresponds to the first predefined action:
the touch screen display is turned on;
the workout pause icon is displayed on the touch screen display; and
the unlock image is displayed on the touch screen display; and
while the portable electronic device is in the user-interface locked mode of the workout monitoring application with the touch screen display turned on:
monitoring the workout by the user with the workout monitoring application;
playing an audio file from a playlist with a plurality of audio files;
detecting a finger swipe gesture on the touch screen display;
in response to detecting the finger swipe gesture:
play of the audio file is terminated and play of a next audio file from the playlist is initiated if the detected finger gesture is in a first horizontal direction, relative to the device, across the touch screen display;
play of the audio file is terminated and play of the next audio file from the playlist is initiated if the detected finger gesture is in a first vertical direction, relative to the device, across the touch screen display;
play of the audio file is terminated and play of a previous audio file from the playlist is initiated if the detected finger gesture is in a second horizontal direction, relative to the device, across the touch screen display, the second horizontal direction being opposite the first horizontal direction; and
play of the audio file is terminated and play of the previous audio file from the playlist is initiated if the detected finger gesture is in a second vertical direction, relative to the device, across the touch screen display, the second vertical direction being opposite the first vertical direction.

53. A computer-implemented method, comprising:
at a portable electronic device with a touch screen display:
while the portable electronic device is in a user-interface locked mode of a workout monitoring application with the touch screen display turned on:
monitoring a workout by a user with the workout monitoring application;
playing an audio file from a playlist with a plurality of audio files;
detecting a finger swipe gesture on the touch screen display;
in response to detecting the finger swipe gesture:
terminating play of the audio file and initiating play of a next audio file from the playlist if the detected finger gesture is in a first horizontal direction, relative to the device, across the touch screen display;
terminating play of the audio file and initiating play of the next audio file from the playlist if the detected finger gesture is in a first vertical direction, relative to the device, across the touch screen display;
terminating play of the audio file and initiating play of a previous audio file from the playlist if the detected finger gesture is in a second horizontal direction, relative to the device, across the touch screen display, the second horizontal direction being opposite the first horizontal direction; and
terminating play of the audio file and initiating play of the previous audio file from the playlist if the detected finger gesture is in a second vertical direction, relative to the device, across the touch screen display, the second vertical direction being opposite the first vertical direction.

54. A portable electronic device, comprising:
a touch screen display;
one or more processors;
memory; and
one or more programs, wherein the one or more programs are stored in the memory and configured to be executed by the one or more processors, the one or more programs including instructions for:
while the portable electronic device is in a user-interface locked mode of a workout monitoring application with the touch screen display turned on:
monitoring a workout by a user with the workout monitoring application;
playing an audio file from a playlist with a plurality of audio files;
detecting a finger swipe gesture on the touch screen display;
in response to detecting the finger swipe gesture:
terminating play of the audio file and initiating play of a next audio file from the playlist if the detected finger gesture is in a first horizontal direction, relative to the device, across the touch screen display;
terminating play of the audio file and initiating play of the next audio file from the playlist if the detected finger gesture is in a first vertical direction, relative to the device, across the touch screen display;
terminating play of the audio file and initiating play of a previous audio file from the playlist if the detected finger gesture is in a second horizontal direction, relative to the device, across the touch screen display, the second horizontal direction being opposite the first horizontal direction; and
terminating play of the audio file and initiating play of the previous audio file from the playlist if the detected finger gesture is in a second vertical direction, relative to the device, across the touch screen display, the second vertical direction being opposite the first vertical direction.

55. A non-transitory computer readable storage medium having stored therein instructions, which when executed by a portable electronic device with a touch screen display, cause the device to:
while the portable electronic device is in a user-interface locked mode of a workout monitoring application with the touch screen display turned on:
monitor a workout by a user with the workout monitoring application;
play an audio file from a playlist with a plurality of audio files;
detect a finger swipe gesture on the touch screen display;
in response to detecting the finger swipe gesture:
terminate play of the audio file and initiate play of a next audio file from the playlist if the detected finger gesture is in a first horizontal direction, relative to the device, across the touch screen display;
terminate play of the audio file and initiate play of the next audio file from the playlist if the detected finger gesture is in a first vertical direction, relative to the device, across the touch screen display;

terminate play of the audio file and initiate play of a previous audio file from the playlist if the detected finger gesture is in a second horizontal direction, relative to the device, across the touch screen display, the second horizontal direction being opposite the first horizontal direction; and terminate play of the audio file and initiate play of the previous audio file from the playlist if the detected finger gesture is in a second vertical direction, relative to the device, across the touch screen display, the second vertical direction being opposite the first vertical direction.

* * * * *